(12) United States Patent
Schwartz et al.

(10) Patent No.: US 7,871,440 B2
(45) Date of Patent: Jan. 18, 2011

(54) UNITARY SURGICAL DEVICE AND METHOD

(75) Inventors: Herbert E. Schwartz, Ft. Wayne, IN (US); Prasanna Malaviya, Ft. Wayne, IN (US); Amit K. Singla, Louisville, KY (US); Pamela Lynn Plouhar, South Bend, IN (US); Mark Joseph Pelo, Macy, IN (US)

(73) Assignee: Depuy Products, Inc., Warsaw, IN (US)

( * ) Notice: Subject to any disclaimer, the term of this patent is extended or adjusted under 35 U.S.C. 154(b) by 574 days.

(21) Appl. No.: 11/609,114

(22) Filed: Dec. 11, 2006

(65) Prior Publication Data
US 2008/0140094 A1 Jun. 12, 2008

(51) Int. Cl.
*A61F 2/08* (2006.01)
(52) U.S. Cl. .................. 623/14.12; 623/23.76
(58) Field of Classification Search .............. 623/23.76, 623/14.12, 23.75; 606/151, 215
See application file for complete search history.

(56) References Cited

U.S. PATENT DOCUMENTS

| | | | |
|---|---|---|---|
| 3,272,204 A | 9/1966 | Artandi et al. | |
| 3,562,820 A | 2/1971 | Braun | |
| 3,867,728 A | 2/1975 | Stubstad et al. | |
| 4,105,034 A | 8/1978 | Shalaby et al. | |
| 4,130,639 A | 12/1978 | Shalaby et al. | |
| 4,140,678 A | 2/1979 | Shalaby et al. | |
| 4,141,087 A | 2/1979 | Shalaby et al. | |
| 4,190,040 A | 2/1980 | Schulte | |

(Continued)

FOREIGN PATENT DOCUMENTS

EP 0 446 105 A2 1/1992

(Continued)

OTHER PUBLICATIONS

Hiles et al., "Mechanical properties of xenogeneic small-intestinal submucosa when used as an aortic graft in the dog", Journal of Biomedical Materials Research, vol. 29, 883-891, (1995).

(Continued)

*Primary Examiner*—Bruce E Snow

(57) ABSTRACT

Unitary surgical devices (10) are disclosed. One group of the illustrated devices has a pair of biocompatible, bioresorbable anchors (16,18) connected to fixed lengths suture. The anchors (16,18) and fixed length of suture are connected to each other prior to surgery. Another group of unitary surgical devices has a pair of fixating mechanisms (15,17) connected to a base (21) prior to surgery. The second group of illustrated devices generally includes extracellular matrix material either as part of the base (21) or supported on the base (21). The extracellular matrix material serves as tissue regenerating material. In the second group of unitary surgical devices, the fixating mechanisms illustrated generally comprise suture, anchors or pre-formed holes in the base. All of the illustrated unitary surgical devices are useful in repairing a damaged meniscus. The first group of unitary surgical devices can be used to approximate inner surfaces of a tear in the meniscus. The second group of devices can be used either as an insert to be placed between and approximated to the inner surfaces of the tear or as an insert to replace a void in the meniscus left after a meniscectomy.

9 Claims, 19 Drawing Sheets

U.S. PATENT DOCUMENTS

| | | | |
|---|---|---|---|
| 4,205,399 A | 6/1980 | Shalaby et al. |
| 4,208,511 A | 6/1980 | Shalaby et al. |
| 4,349,921 A | 9/1982 | Kuntz |
| 4,352,463 A | 10/1982 | Baker |
| 4,400,833 A | 8/1983 | Kurland |
| 4,418,691 A | 12/1983 | Yannas et al. |
| 4,428,082 A | 1/1984 | Naficy |
| 4,585,458 A | 4/1986 | Kurland |
| 4,610,397 A | 9/1986 | Fischer et al. |
| 4,642,120 A | 2/1987 | Nevo et al. |
| 4,669,473 A | 6/1987 | Richards et al. |
| 4,703,108 A | 10/1987 | Silver et al. |
| 4,705,040 A | 11/1987 | Mueller et al. |
| 4,741,330 A | 5/1988 | Hayhurst |
| 4,750,492 A | 6/1988 | Jacobs |
| 4,772,284 A | 9/1988 | Jefferies et al. |
| 4,775,361 A | 10/1988 | Jacques et al. |
| 4,820,302 A | 4/1989 | Woodroof |
| 4,823,815 A | 4/1989 | Watson et al. |
| 4,846,835 A | 7/1989 | Grande |
| 4,873,976 A | 10/1989 | Schreiber |
| 4,880,429 A | 11/1989 | Stone |
| 4,902,508 A | 2/1990 | Badylak et al. |
| 4,919,667 A | 4/1990 | Richmond |
| 4,956,178 A | 9/1990 | Badylak et al. |
| 4,956,179 A | 9/1990 | Bamberg et al. |
| 4,976,715 A | 12/1990 | Bays et al. |
| 5,007,934 A | 4/1991 | Stone |
| 5,013,323 A | 5/1991 | Kobayashi et al. |
| 5,061,286 A | 10/1991 | Lyle |
| 5,102,421 A | 4/1992 | Anspach, Jr. |
| 5,108,438 A | 4/1992 | Stone |
| 5,116,374 A | 5/1992 | Stone |
| 5,128,326 A | 7/1992 | Balazs et al. |
| RE34,021 E | 8/1992 | Mueller et al. |
| 5,171,280 A | 12/1992 | Baumgartner |
| 5,197,882 A | 3/1993 | Jernberg |
| 5,227,627 A | 7/1993 | Gamarnik et al. |
| 5,236,431 A | 8/1993 | Gogolewski et al. |
| 5,236,454 A | 8/1993 | Miller |
| 5,246,441 A | 9/1993 | Ross et al. |
| 5,258,015 A | 11/1993 | Li et al. |
| 5,269,809 A | 12/1993 | Hayhurst et al. |
| 5,275,826 A | 1/1994 | Badylak et al. |
| 5,281,422 A | 1/1994 | Badylak et al. |
| 5,306,307 A | 4/1994 | Senter et al. |
| 5,306,311 A | 4/1994 | Stone et al. |
| 5,320,633 A | 6/1994 | Allen et al. |
| 5,329,846 A | 7/1994 | Bonutti |
| 5,341,292 A | 8/1994 | Zamenhof |
| 5,350,583 A | 9/1994 | Yoshizato et al. |
| 5,352,463 A | 10/1994 | Badylak et al. |
| 5,368,051 A | 11/1994 | Dunn et al. |
| 5,372,821 A | 12/1994 | Badylak et al. |
| 5,374,268 A | 12/1994 | Sander |
| 5,376,117 A | 12/1994 | Pinchuk et al. |
| 5,376,118 A | 12/1994 | Kaplan et al. |
| 5,380,334 A | 1/1995 | Torrie et al. |
| 5,445,833 A | 8/1995 | Badylak et al. |
| 5,447,940 A | 9/1995 | Harvey et al. |
| 5,460,962 A | 10/1995 | Kemp |
| 5,464,929 A | 11/1995 | Bezwada et al. |
| 5,479,033 A | 12/1995 | Baca et al. |
| 5,514,181 A | 5/1996 | Light et al. |
| 5,516,533 A | 5/1996 | Badylak et al. |
| 5,520,691 A | 5/1996 | Branch |
| 5,545,178 A | 8/1996 | Kensey et al. |
| 5,554,389 A | 9/1996 | Badylak et al. |
| 5,569,252 A | 10/1996 | Justin et al. |
| 5,571,189 A | 11/1996 | Kuslich |
| 5,573,784 A | 11/1996 | Badylak et al. |
| 5,591,234 A | 1/1997 | Kirsch |
| 5,593,441 A | 1/1997 | Lichtenstein et al. |
| 5,595,621 A | 1/1997 | Light et al. |
| 5,595,751 A | 1/1997 | Bezwada et al. |
| 5,597,579 A | 1/1997 | Bezwada et al. |
| 5,601,558 A | 2/1997 | Torrie et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,626,614 A | 5/1997 | Hart |
| 5,630,824 A | 5/1997 | Hart |
| 5,632,745 A | 5/1997 | Schwartz |
| 5,641,518 A | 6/1997 | Badylak et al. |
| 5,645,850 A | 7/1997 | Bezwada et al. |
| 5,645,860 A | 7/1997 | Knapp, Jr. et al. |
| 5,648,088 A | 7/1997 | Bezwada et al. |
| 5,660,225 A | 8/1997 | Saffran |
| 5,668,288 A | 9/1997 | Storey et al. |
| 5,669,912 A | 9/1997 | Spetzler |
| 5,677,355 A | 10/1997 | Shalaby et al. |
| 5,681,353 A | 10/1997 | Li et al. |
| 5,693,085 A | 12/1997 | Buirge et al. |
| 5,695,998 A | 12/1997 | Badylak et al. |
| 5,698,213 A | 12/1997 | Jamiolkowski et al. |
| 5,700,583 A | 12/1997 | Jamiolkowski et al. |
| 5,702,462 A | 12/1997 | Oberlander |
| 5,709,934 A | 1/1998 | Bell et al. |
| 5,711,960 A | 1/1998 | Shikinami |
| 5,711,969 A | 1/1998 | Patel et al. |
| 5,725,556 A | 3/1998 | Moser et al. |
| 5,730,933 A | 3/1998 | Peterson |
| 5,733,337 A | 3/1998 | Carr, Jr. et al. |
| 5,733,868 A | 3/1998 | Peterson et al. |
| 5,735,897 A | 4/1998 | Buirge |
| 5,735,903 A | 4/1998 | Li et al. |
| 5,736,372 A | 4/1998 | Vacanti et al. |
| 5,753,267 A | 5/1998 | Badylak et al. |
| 5,755,791 A | 5/1998 | Whitson et al. |
| 5,759,190 A | 6/1998 | Vibe-Hansen et al. |
| 5,759,205 A | 6/1998 | Valentini |
| 5,759,208 A | 6/1998 | Valentini |
| 5,762,600 A | 6/1998 | Bruchman et al. |
| 5,762,966 A | 6/1998 | Knap et al. |
| 5,769,899 A | 6/1998 | Schwartz et al. |
| 5,773,577 A | 6/1998 | Cappello |
| 5,788,625 A | 8/1998 | Plouhar et al. |
| 5,795,353 A | 8/1998 | Felt |
| 5,800,537 A | 9/1998 | Bell |
| 5,830,708 A | 11/1998 | Naughton |
| 5,834,232 A | 11/1998 | Bishop |
| 5,842,477 A | 12/1998 | Naughton et al. |
| 5,847,012 A | 12/1998 | Shalaby et al. |
| 5,855,610 A | 1/1999 | Vacanti et al. |
| 5,855,613 A | 1/1999 | Antanavich et al. |
| 5,855,619 A | 1/1999 | Caplan et al. |
| 5,859,150 A | 1/1999 | Jamiolkowski et al. |
| 5,861,004 A | 1/1999 | Kensey et al. |
| 5,863,551 A | 1/1999 | Woerly |
| 5,865,849 A | 2/1999 | Stone |
| 5,866,165 A | 2/1999 | Liu et al. |
| 5,866,414 A | 2/1999 | Badylak et al. |
| 5,885,619 A | 3/1999 | Patel et al. |
| 5,891,558 A | 4/1999 | Bell et al. |
| 5,899,939 A | 5/1999 | Boyce et al. |
| 5,906,997 A | 5/1999 | Schwartz et al. |
| 5,916,265 A | 6/1999 | Hu |
| 5,922,024 A | 7/1999 | Janzen et al. |
| 5,922,028 A | 7/1999 | Plouhar et al. |
| 5,922,815 A | 7/1999 | Aycock et al. |
| 5,939,323 A | 8/1999 | Valentini et al. |
| 5,948,429 A | 9/1999 | Bell et al. |
| 5,954,723 A | 9/1999 | Spetzler |
| 5,954,747 A | 9/1999 | Clark |

| | | | | | | |
|---|---|---|---|---|---|---|
| 5,955,100 | A | 9/1999 | Bosslet et al. | 6,319,271 | B1 | 11/2001 | Schwartz et al. |
| 5,958,874 | A | 9/1999 | Clark et al. | 6,326,025 | B1 | 12/2001 | Sigler et al. |
| 5,968,096 | A | 10/1999 | Whitson et al. | 6,333,029 | B1 | 12/2001 | Vyakamam et al. |
| 5,969,020 | A | 10/1999 | Shalaby et al. | 6,334,872 | B1 | 1/2002 | Termin et al. |
| 5,971,987 | A | 10/1999 | Huxel et al. | 6,355,699 | B1 | 3/2002 | Vyakarnam et al. |
| 5,980,524 | A | 11/1999 | Justin et al. | 6,358,284 | B1 | 3/2002 | Fearnot et al. |
| 5,981,825 | A | 11/1999 | Brekke | 6,364,884 | B1 | 4/2002 | Bowman et al. |
| 5,989,269 | A | 11/1999 | Vibe-Hansen et al. | 6,371,958 | B1 | 4/2002 | Overaker |
| 5,989,280 | A | 11/1999 | Euteneuer et al. | 6,373,221 | B1 | 4/2002 | Koike et al. |
| 5,993,475 | A | 11/1999 | Lin et al. | 6,379,367 | B1 | 4/2002 | Vibe-Hansen et al. |
| 5,993,844 | A | 11/1999 | Abraham et al. | 6,379,710 | B1 | 4/2002 | Badylak |
| 5,997,575 | A | 12/1999 | Whitson et al. | 6,383,221 | B1 | 5/2002 | Scarborough et al. |
| 6,010,525 | A | 1/2000 | Bonutti et al. | 6,387,693 | B2 | 5/2002 | Rieser et al. |
| 6,017,301 | A | 1/2000 | Schwartz et al. | 6,402,766 | B2 | 6/2002 | Bowman et al. |
| 6,017,348 | A | 1/2000 | Hart et al. | 6,409,764 | B1 | 6/2002 | White et al. |
| 6,027,744 | A | 2/2000 | Vacanti et al. | 6,423,073 | B2 | 7/2002 | Bowman |
| 6,034,140 | A | 3/2000 | Schwartz et al. | 6,436,110 | B2 | 8/2002 | Bowman et al. |
| 6,042,610 | A | 3/2000 | Li et al. | 6,440,444 | B2 | 8/2002 | Boyce et al. |
| 6,051,750 | A | 4/2000 | Bell | 6,447,517 | B1 | 9/2002 | Bowman |
| 6,056,752 | A | 5/2000 | Roger | 6,451,032 | B1 | 9/2002 | Ory et al. |
| 6,056,777 | A | 5/2000 | McDowell | 6,458,158 | B1 | 10/2002 | Anderson et al. |
| 6,056,778 | A | 5/2000 | Grafton et al. | 6,458,383 | B2 | 10/2002 | Chen et al. |
| 6,060,640 | A | 5/2000 | Pauley et al. | 6,464,729 | B1 | 10/2002 | Kandel |
| 6,066,160 | A | 5/2000 | Colvin et al. | 6,497,650 | B1 | 12/2002 | Nicolo |
| 6,068,648 | A | 5/2000 | Cole et al. | 6,497,707 | B1 | 12/2002 | Bowman et al. |
| 6,077,989 | A | 6/2000 | Kandel et al. | 6,508,821 | B1 | 1/2003 | Schwartz et al. |
| 6,080,194 | A | 6/2000 | Pachence et al. | 6,517,564 | B1 | 2/2003 | Grafton et al. |
| 6,093,201 | A | 7/2000 | Cooper et al. | 6,566,345 | B2 | 5/2003 | Miller et al. |
| 6,098,347 | A | 8/2000 | Jaeger et al. | 6,572,650 | B1 | 6/2003 | Abraham et al. |
| 6,099,567 | A | 8/2000 | Badylak et al. | 6,592,623 | B1 | 7/2003 | Bowlin et al. |
| 6,110,212 | A | 8/2000 | Gregory | 6,596,296 | B1 | 7/2003 | Nelson et al. |
| 6,126,686 | A | 10/2000 | Badylak et al. | 6,602,291 | B1 | 8/2003 | Ray et al. |
| 6,132,465 | A | 10/2000 | Ray et al. | 6,629,997 | B2 * | 10/2003 | Mansmann ............... 623/14.12 |
| 6,133,325 | A | 10/2000 | Schwartz et al. | 6,638,312 | B2 | 10/2003 | Plouhar et al. |
| 6,146,385 | A | 11/2000 | Torrie et al. | 6,652,872 | B2 | 11/2003 | Nevo et al. |
| 6,152,935 | A | 11/2000 | Kammerer et al. | 6,666,892 | B2 | 12/2003 | Hiles et al. |
| 6,153,292 | A | 11/2000 | Bell et al. | 6,692,499 | B2 | 2/2004 | Tormala et al. |
| 6,156,044 | A | 12/2000 | Kammerer et al. | 6,743,255 | B2 | 6/2004 | Ferree |
| 6,165,225 | A | 12/2000 | Antanavich et al. | 6,808,194 | B2 | 10/2004 | Martin |
| 6,171,344 | B1 | 1/2001 | Atala | 6,812,221 | B2 | 11/2004 | McKeehan et al. |
| 6,176,880 | B1 | 1/2001 | Plouhar et al. | 6,840,962 | B1 | 1/2005 | Vacanti et al. |
| 6,179,840 | B1 | 1/2001 | Bowman | 6,869,938 | B1 | 3/2005 | Schwartz et al. |
| 6,179,872 | B1 | 1/2001 | Bell et al. | 6,989,034 | B2 | 1/2006 | Hammer et al. |
| 6,187,039 | B1 | 2/2001 | Hiles et al. | 7,001,385 | B2 * | 2/2006 | Bonutti ....................... 606/60 |
| 6,190,414 | B1 | 2/2001 | Young et al. | 2001/0002446 | A1 | 5/2001 | Plouhar et al. |
| 6,197,296 | B1 | 3/2001 | Davies et al. | 2001/0023373 | A1 | 9/2001 | Plouhar et al. |
| 6,206,931 | B1 | 3/2001 | Cook et al. | 2001/0024658 | A1 | 9/2001 | Chen et al. |
| 6,214,047 | B1 | 4/2001 | Melvin | 2001/0043943 | A1 | 11/2001 | Coffey |
| 6,214,048 | B1 | 4/2001 | Ito et al. | 2002/0019649 | A1 | 2/2002 | Sikora et al. |
| 6,214,049 | B1 | 4/2001 | Gayer et al. | 2002/0031551 | A1 | 3/2002 | Peterson et al. |
| 6,224,892 | B1 | 5/2001 | Searle | 2002/0034533 | A1 | 3/2002 | Peterson et al. |
| 6,235,057 | B1 | 5/2001 | Roger et al. | 2002/0038151 | A1 | 3/2002 | Plouhar et al. |
| 6,242,247 | B1 | 6/2001 | Rieser et al. | 2002/0048595 | A1 | 4/2002 | Geistlich et al. |
| 6,251,143 | B1 | 6/2001 | Schwartz et al. | 2002/0052628 | A1 | 5/2002 | Bowman |
| 6,251,876 | B1 | 6/2001 | Bellini et al. | 2002/0090725 | A1 | 7/2002 | Simpson et al. |
| 6,258,124 | B1 | 7/2001 | Darois et al. | 2002/0091444 | A1 | 7/2002 | Yang |
| 6,264,702 | B1 | 7/2001 | Ory et al. | 2002/0095157 | A1 | 7/2002 | Bowman |
| 6,265,333 | B1 | 7/2001 | Dzenis et al. | 2002/0099448 | A1 | 7/2002 | Hiles |
| 6,267,957 | B1 | 7/2001 | Green et al. | 2002/0131989 | A1 | 9/2002 | Brown et al. |
| 6,270,530 | B1 | 8/2001 | Eldridge et al. | 2002/0147497 | A1 | 10/2002 | Belef et al. |
| 6,273,893 | B1 | 8/2001 | McAllen, III et al. | 2002/0156400 | A1 | 10/2002 | Babaev |
| 6,280,473 | B1 | 8/2001 | Lemperle et al. | 2002/0165611 | A1 | 11/2002 | Enzerink et al. |
| 6,280,474 | B1 | 8/2001 | Cassidy et al. | 2002/0169465 | A1 | 11/2002 | Bowman et al. |
| 6,283,980 | B1 | 9/2001 | Vibe-Hansen et al. | 2002/0173806 | A1 | 11/2002 | Giannetti et al. |
| 6,288,043 | B1 | 9/2001 | Spiro et al. | 2002/0190136 | A1 | 12/2002 | Babaev |
| 6,290,711 | B1 | 9/2001 | Caspari et al. | 2003/0014126 | A1 | 1/2003 | Patel et al. |
| 6,293,961 | B2 | 9/2001 | Schwartz et al. | 2003/0021827 | A1 | 1/2003 | Malaviya et al. |
| 6,294,041 | B1 | 9/2001 | Boyce et al. | 2003/0023316 | A1 | 1/2003 | Brown et al. |
| 6,299,905 | B1 | 10/2001 | Peterson et al. | 2003/0032961 | A1 | 2/2003 | Pelo et al. |
| 6,306,156 | B1 | 10/2001 | Clark | 2003/0033021 | A1 | 2/2003 | Plouhar et al. |
| 6,306,159 | B1 | 10/2001 | Schwartz et al. | 2003/0033022 | A1 | 2/2003 | Plouhar et al. |
| 6,306,177 | B1 | 10/2001 | Felt et al. | 2003/0036797 | A1 | 2/2003 | Malaviya et al. |
| 6,319,258 | B1 | 11/2001 | McAllen, III et al. | 2003/0036801 | A1 | 2/2003 | Schwartz et al. |

| | | | |
|---|---|---|---|
| 2003/0044444 | A1 | 3/2003 | Malaviya et al. |
| 2003/0049299 | A1 | 3/2003 | Malaviya et al. |
| 2003/0078617 | A1 | 4/2003 | Schwartz et al. |
| 2003/0212447 | A1 | 11/2003 | Euteneuer et al. |
| 2004/0059431 | A1 | 3/2004 | Plouhar et al. |
| 2004/0143344 | A1 | 7/2004 | Malaviya et al. |
| 2004/0166169 | A1 | 8/2004 | Malaviya et al. |
| 2004/0220574 | A1 | 11/2004 | Pelo et al. |
| 2005/0027307 | A1 | 2/2005 | Schwartz et al. |
| 2005/0112248 | A1 | 5/2005 | Galloway |
| 2005/0249771 | A1 | 11/2005 | Malaviya et al. |
| 2005/0249772 | A1 | 11/2005 | Malaviya et al. |

FOREIGN PATENT DOCUMENTS

| | | |
|---|---|---|
| EP | 0 591 991 A2 | 4/1994 |
| EP | 0 632 999 A1 | 11/1995 |
| EP | 0 734 736 A1 | 10/1996 |
| EP | 1070487 B1 | 1/2001 |
| EP | 1 593 400 A1 | 11/2005 |
| FR | 2 422 386 | 4/1978 |
| GB | 606427 | 8/1948 |
| GB | 805843 | 12/1958 |
| GB | 968840 | 9/1964 |
| GB | 2215209 A | 9/1989 |
| JP | 11319068 A | 11/1999 |
| WO | WO 90/09769 | 9/1990 |
| WO | 94/03584 A1 | 2/1994 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | WO 95/32623 | 12/1995 |
| WO | 96/24304 A1 | 8/1996 |
| WO | 96/25961 A1 | 8/1996 |
| WO | WO 96/24661 | 8/1996 |
| WO | WO 97/05193 | 2/1997 |
| WO | 97/30662 A1 | 8/1997 |
| WO | WO 97/37613 | 10/1997 |
| WO | WO 98/06445 | 2/1998 |
| WO | 98/22154 A1 | 5/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 98/40111 | 9/1998 |
| WO | WO 99/03979 | 1/1999 |
| WO | 99/19005 A1 | 4/1999 |
| WO | WO 99/43786 | 9/1999 |
| WO | WO 99/47188 | 9/1999 |
| WO | 00/15153 A1 | 3/2000 |
| WO | WO 00/15765 | 3/2000 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | 00/62439 A2 | 10/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 01/70293 | 9/2001 |
| WO | WO 01/70293 A1 | 9/2001 |
| WO | WO 02/22184 | 3/2002 |
| WO | WO 03/007784 | 1/2003 |
| WO | WO 03/007788 | 1/2003 |
| WO | WO 03/007790 | 1/2003 |
| WO | WO 03/097694 | 11/2003 |
| WO | WO 03/097694 A1 | 11/2003 |

OTHER PUBLICATIONS

Sandusky, et al., "Healing Comparison of Small Intestine Submucosa and ePTFE Grafts in the Canine Carotid Artery", J. Surg.Res., 58:415-420, (1995).

Knapp, et al., "Biocompatibility of Small-Intestine Submucosa in Urinary Tract as Augmentation Cystoplasty Graft and Injectable Suspension", J Endourology, 8:125-130, (1994).

Kropp et al., "Regenerative Bladder Augmentation: A Review of the Initial Preclinical Studies with Porcine Small Intestinal Submucosa", Muscle, Matrix, and Bladder Function. Plenum Press, New York, (1995).

Kropp et al., "Experimental Assessment of Small Intestinal Submucosa as a Bladder Wall Substitute", Urology 446:396-400, (1995).

Vaught et al., "Detrusor Regeneration in the Rat Using Porcine Small Intestinal Submucosa Grafts: Functional Innervation and Receptor Expression", J. Urol., 155:374-378, (1996).

Kropp et al, Characterization of Small Intestinal Submucosa Regenerated Canine Detrusor: Assessment of Reinnervation, In Vitro Compliance and contractility, J. of Urol,156:599-607, (1996).

Kropp et al., "Regenerative Urinary Bladder Augmentation Using Small Intestinal Submucosa: Urodynamic and Histopathologic Assessment in Long-Term Canine Bladder Augmentations", Journal of Urology.

Aiken et al., "Small Intestinal Submucosa as an Intra-Articular Ligamentous Graft Material: A Pilot Study in Dogs", Vet Comp Orthopedics Traumatology, 7:124-128, (1994).

Badylak et al., "The Use of Xenogeneic Small Intestinal Submucosa as a Biomaterial for Achille's Tendon Repair in a dog model", J Biomed Materials, 29:977-985, (1995).

Hodde et al., "The Effect of Range of Motion Upon Remodeling of Small Intestinal Submucosa (SIS) when used as an Achilles Tendon Repair Material in the Rabbit", Tissue Engineering 3, 1:27-37, (1997).

Ferrand et al., "Directional Porosity of Porcine Small-Intestinal Submucosa", J Biomed Materials Res, 27:1235-1241, (1993).

Hiles et al., "Porosity of Porcine Small-Intestinal Submucosa for use as a Vascular Graft", J Biomed Materials Res, 27: 139-144, (1993).

Hodde et al., "Glycosaminoglycan Content of Small Intestinal Submucosa: A Bioscaffold for Tissue Replacement", Tissue Engineering, 2:3, 209-217, (1996).

Prevel et al., "Small Intestinal Submucosa: Utilization for Repair of Rodent Abdominal Wall Defects", Ann Plast Surg, 35:374-380, (1995).

Clarke et al., "Intestine Submucosa and Polypropylene Mesh for Abdominal Wall Repair in Dogs", J Surg Res, 60:107-114, (1996).

Prevel et al., "Small Intestinal Submucosa: Utilization as a Wound Dressing in Full-Thickness Rodent Wounds", Ann Plast Surg. 35:381-388, (1995).

Cobb et al., "Histology after Dural Grafting with Small Intestinal Submucosa", Surgical Neurology, 46: 389-394, (1996).

Cobb et al., "Porcine Small Intestinal Submucosa as a Dural Substitute", Surgical Neurology, 51:99-104, (1999).

Voytik-Harbin et al., "Application and Evaluation of the AlamarBlue Assay for Cell Growth and Survival of Fibroblasts", Journal of Immunological Methods, In Vitro Cell Bio-Animal, 34: 2399-246, (1998).

Suckow, M.A., "Enhanced Bone Regeneration Using Porcine Small Intestinal Submucosa", J. Invest Surg, 12: 277, (1999).

Badylak, S., et al., "Naturally Occurring Extracellular Matrix as a Scaffold for Musculoskeletal Repair", Clin Orthop, 3675:S333-S3433, (1999).

Cook, J.L. et al., "Induction of Meniscal Regeneration in Dogs Using a Novel Biomaterial", Am J Sports Med, 27: 658, (1999).

Dejardin, L.M. et al., "Use of small intestinal submucosal implants for regeneration of large fascial defects: an experimental study in dogs", J Biomed Mater Res, 46:203-211, (1999).

Sacks, M.S., et al., "Quantification of the fiber architecture and biaxial mechanical behavior of porcine intestinal submucosa", J Biomed Mater Res, 46:1-10, (1999).

Cook® News Releases, "Cook® Introduces Innovative Surgisis™ Soft Tissue Repair Biomaterial", (May 21, 2000).

Cook® News Releases, "Cook® Oasis™ Wound Dressing Biomaterial From Cook® Remodels Partial Thickness Skin Injuries", (Dec. 23, 1999).

Cook® News Releases, "Cook Incorporated Forms Dedicated Tissue Engineered Products Group", (Feb. 16, 2000).

Cook® News Releases, "FDA Clears Oasis™ Wound Dressing Biomaterial From Cook® For Full-Thickness Skin Injuries", (Jan. 24, 2000).

Klootwyk, et al., "The Use of Xenographic SIS as a Biomaterial for Achilles Tendon Repair in Dogs," First SIS Symposium, Dec. 1996, USA.

Lenz, et al., "SIS as an ACL Replacement in Dogs and Goats," First Symposium, Dec. 1996, USA.

Cook, et al., "Comparison of SIS Cancellous Bone as Substrates for Three-Dimensional Culture of Canine Articular Chondrocytes," First SIS Symposium, Dec. 1996, USA.

Badylak, et al., "Different Configurations of Small Intestinal Submucosa as a Biomaterial for Achilles Tendon Repair in a Dog Model," First SIS Symposium, Dec. 1996, USA.

Voytik-Harbin & Badylak, "Induction of Osteogenic Activity By Small Intestinal Submucosa in Rat Calvaria Non-union Defects," First SIS Symposium, Dec. 1996, USA.

Kandel, et al., "SIS and Reconstituted Cartilage and Its Use in Joint Resurfacing of Focal Defects in Rabbits," First SIS Symposium, Dec. 1996, USA.

Tullius, et al., "Differential Permeabilty of SIS," First SIS Symposium, Dec. 1996, USA.

Obermiller, et al., "Suture Retention Strength of SIS," First SIS Symposium, Dec. 1996, USA.

Shelton, et al., "Repair of the Canine Medial Meniscus using SIS: A Feasibility Study," Second SIS Symposium, Dec. 1998, USA.

Cook, et al., "Meniscal Regeneration in dogs Using Grafts of SIS," Second SIS Symposium, Dec. 1998, USA.

Welch, et al., "Healing of Canine Meniscal Defect with Small Intestinal Submucosa Implants," Dec. 1998, USA.

Solchaga, et al., "SIS as Delivery Vehicle for Mesenchymal Progenitor Cells," Dec. 1998, USA.

Paulino, et al., "The Use of an SIS-PGA Composite Graft for Repair of Cartilage Defect," Dec. 1998, USA.

Toombs and May, "Clinical Follow-Up of Three Canine ACL Reconstructions Using an SIS ACL Device," Dec. 1998, USA.

Tomasek and Gifford, "Small Intestinal Submucosa Matrix Regulates the Differentiation of Myofibroblasts," Third SIS Symposium, Nov. 2000, USA.

Cook, et al., "Tissue Engineering for Meniscal Repair Using SIS," Third SIS Symposium, Nov. 2000, USA.

Lifrak, et al., "Enhanced Repair of Goat Meniscal Defects Using Porcine Small Intestinal Submucosa (SIS)," Third SIS Symposium, Nov. 2000, USA.

Hoffman, "SIS Disc Replacement for the Temporomandibular Joint," Third SIS Symposium, Nov., 2000, USA.

Kaeding, "Use of SIS in the Surgical Treatment of Chronic Symptomatic Patella Tendinosis," Third SIS Symposium, Nov. 2000, USA.

Tomczak and Kaeding, "Use of SIS in the Surgical Treatment of Tendinosis About the Foot and Ankle," Third SIS Symposium, Nov. 2000, USA.

Moore, et al., "Bridging Segmental Defects in Long Bones With Intramedullary Tubes and Periosteal Sleeves Made From Small Intestinal Submucosa (SIS)," Third SIS Symposium, Nov. 2000, USA.

Wang, et al., "Small Intestinal Submucosa Enhances Healing of Medical Collateral Ligament in a Rabbit Model," Third SIS Symposium, Nov. 2000, USA.

Ojha, et al., "PGA-Plla Versus Small Intestinal Submucosa (SIS): A Comparison of Neo-Cartilage Grown From Two Scaffold Materials," Third SIS Symposium, Nov. 2000, USA.

Wiklerson, "Use of the Porcine Small Intestine Submucosal Tissue Graft and Repair of Rotator Cuff Tears," Third SIS Symposium, Nov. 2000, USA.

Small Intestinal Submucosa, Third SIS Symposium, Nov. 2000, USA.

Current Clinical Applications of SIS, Third SIS Symposium, Nov. 2000, USA.

Hodde, et al., "Glycosaminoglycan Content of Small Intestinal Submucosa: a Potential for GAG-Growth Interactions in SIS-Mediated Healing", First Symposium, Dec. 1996, USA.

Friess, "Collagen in drug delivery and tissue engineering", Advanced Drug Delivery Reviews, vol. 55, No. 12, 2003, pp. 1529-1530.

Olsen et al., "Recombinant collagen and gelatin for drug delivery", Advanced Drug Delivery Reviews, vol. 55, No. 12, 2003, pp. 1547-1567.

Aigner et al., "Collagens-major component of the physiological cartilage matrix, major target of cartilage degeneration, major tool in cartilage repair", Advanced Drug Delivery Reviews, vol. 55, No. 12, 2003, pp. 1569-1593.

Geiger et al., "Collagen sponges for bone regeneration with rhBMP-2", Advanced Drug Delivery Reviews, vol. 55, No. 12, 2003, pp. 1613-1629.

Ruszczak et al., "Collagen as a carrier for on-site delivery of antibacterial drugs", Advanced Drug Delivery Reviews, vol. 55, No. 12, 2003, pp. 1679-1698.

O'Grady et al., "Global regulatory registration requirements for collagen-based combination products: points to consider", Advanced Drug Delivery Reviews, vol. 55, No. 12, 2003, pp. 1699-1721.

Matthews et al., "Electrospinning of Collagen Type II: A Feasibility Study", Journal of Bioactive and Compatible Polymers, vol. 18, Mar. 2003, pp. 125-134.

Biscarini et al., "Growth of High Vacuum Sublimed Oligomer Thin Films", ACS Polymer Preprints, vol. 37, No. 2, 1996, pp. 618-619.

Biscarini et al., "Morphology and roughness of high-vacuum sublimed oligomer thin films", Thin Solid Films, vol. 439-443, 1996, pp. 284-285.

Biscarini et al., "Scaling Behavior of Anisotropic Organic Thin Films Grown in High-Vacuum", Physical Review Letters, vol. 78, No. 12, Mar. 24, 1997, pp. 2389-2392.

Voytik-Harbin et al., "Identification of Extractable Growth Factors from Small Intestinal Submucosa", Journal of Cellular Biochemistry, vol. 67, 1997, pp. 478-491.

McPherson, Ph.D. et al., "Characterization of Fibronectin Derived from Porcine Small Intestinal Submucosa", Tissue Engineering, vol. 4, No. 1, 1998, pp. 75-83.

Hodde, et al., "Vascular Endothelial Growth Factor in Porcine-Derived Extracellular Matrix", Endothelium, vol. 8(1), 2001, pp. 11-24.

Hodde et al., "Wounds: a Compendium of Clinical Research and Practice", Website: http:www.hmpcommunications.com/WNDS, Printed: Jul. 12, 2005, 7 pgs.

Hurst et al., "Mapping of the distribution of significant proteins and proteoglycans in small intestinal submucosa by fluorescence microscopy", J. Biomater. Sci. Polymer Edn., vol. 12, No. 11, 2001, pp. 1267-1279.

Hodde et al., "Fibronectin peptides mediate HMEC adhesion to porcine-derived extracellular matrix", Biomaterials, vol. 23, 2002, pp. 1841-1848.

Hodde, "Naturally Occurring Scaffolds for Soft Tissue Repair and Regeneration", Tissue Engineering, vol. 8, No. 2, 2002, pp. 295-308.

Allman et al., Xenogeneic Extracellular Matrix Grafts Elicit a Th2-Restricted Immune Response, Transplantation, vol. 71, No. 11, Jun. 15, 2001, pp. 1631-1640.

Krcma, "Nonwoven Textiles", Textile Trade Press, Manchester, England, 1962, 6 pgs.

Answers.com definition of "freeze-dry" accessed May 12, 2005. 6 pages.

Ma and Zhang, 2001, "Microtubular Architecture of Biodegradable Polymer Scaffolds," J Biomed Mater Res, 56(4), pp. 469-477.

Ma and Choi, 2001 "Biodegradable Polymer Scaffolds with Well-Defined Interconnnected Spherical Pore Network," Tissue Eng, 7(1), pp. 23-33.

Klawitter et al., 1976, "An Evaluation of Bone Growth into Porous High Density Polyethylene," J Biomed Mater Res, 10(2), pp. 311-323.

White and Shors, 1986, "Biomaterial Aspects of Interpore-200 Porous Hydroxyapatite," Dent Clin North Am, 30, pp. 49-67.

Shors, 1999, "Coralline Bone Graft Substitutes," Orthop Clin North Am, 30(4), pp. 599-613.

Wang, 1990, "Experimental Study of Osteogenic Activity of Sintered Hydroxyapatite -On the Relationship of Sintering Temperature and Pore Size," Nippon Seikeigeka Gakki Zasshi, 64(9), pp. 847-859.

Nehrer et al., 1997, "Matrix collagen type and pore size influence behaviour of seeded canine chondrocytes," Biomaterials, 18(11), pp. 769-776.

Salem et al., 2002, "Interactions of 3T3 fibroblasts and endothelial cells with defined pore features," J. Biomed Mater Res, 61(2):212-217.

Definitions of "intertwine" and "twine", American Heritage Dictionary of the English Language Online, Accessed Sep. 29, 2005, 2 pgs.

How to Cut Meat Products 2001, Urschel Corp., Assessed online at fr.urschel.com/literature/HTCMeat.pdf on Oct. 3, 2005, 8 pgs.

Definitions of "comminute" and "slurry", Dictionary.com; Accessed Sep. 20, 2005, 2 pgs.

P. K. Chu et al., "Plasma-surface modification of biomaterials", Materials Science and Engineering, Reports: A Review Journal, vol. 36, No. 5-6, Mar. 29, 2002, pp. 143-206.

Arnoczky et al., The microvasculature of the meniscus and its response to injury—An experimental study in the dog, Am. J. Sports Med., 1983, 11(3); pp. 131-141.

Fox et al., Trephination of incomplete meniscal tears, Arthroscopy, 1993, 9(4); pp. 451-455.

Arnoczky et al., Meniscal repair using an exogenous fibrin clot—An experimental study of dogs, J. Bone Joint Surg. Am., 1988, 70(8), pp. 1209-1216.

Rodeo, "Arthroscopic meniscal repair with use of the outside-in technique", Instr. Course Lect., 2000, 49, pp. 195-206.

Stollsteimer et al., "Meniscal allograft transplantation: a 1- to 5-year follow-up of 22 patients", Arhroscopy, 2000, 16(4), pp. 343-347.

Rodeo, "Meniscal allografts—where do we stand?", Am. J. Sports Med., 2001, 29(2), pp. 246-261.

Sweigart et al., "Toward tissue engineering of the knee meniscus", Tissue Eng., 2001, 7(2), pp. 111-129.

Boss et al., "Technical innovative: creation of a peripheral vascularized trough to enhance healing in cryopreserved meniscal allograft reconstruction", Knee Surg Sports Traumatol Arthrosc., 2000, 8(3), pp. 159-162.

Siegel et al., "Meniscal allografts", Clin Sports Med., 1993, 12(1), pp. 59-80.

Klompmaker et al., "Meniscal replacement using a porous polymer prosthesis: a preliminary study in the dog.", Biomaterials, 1996, 17(12), pp. 1169-1175.

de Groot et al., "Use of porous polyurethanes for meniscal reconstruction and meniscal protheses", Biomaterials, 1996, 17(2), pp. 163-173.

Spaans et al., "Solvent-free fabrication of micro-porous polyurethane amide and polyurethane-urea scaffolds for repair and replacement of the knee-joint meniscus", Biomaterials, 2000, 21(23), pp. 2453-2460.

Stone et al., "Regeneration of meniscal cartilage with use of a collagen scaffold—Analysis of Preliminary data", J. Bone Joint Surg. Am., 1997, 79(12), pp. 1770-1777.

Rodkey et al., "A clinical study of collagen meniscus implants to restore the injured meniscus", Clin. Orthop., 1999, 49(367 Suppl.), pp. S281-S292.

Merriam-Webster Online Dictionary definitions of "suspension", "suspend", "cohesive", "cohesion", "comminute", "pulverize", "submucosa", and "tissue". Accessed Mar. 30, 2006, 9 pgs.

Resin Technology Group, LLC, "Viscosity chart", http://www.resintechgroup.com/tables/viscosity.html, accessed online Mar. 30, 2006, 1pg.

Definitions from Onelook.com for "trimethylen" and "trimethylene".

J.S. Pieper et al "Preparation and characterization of porous crosslinked collagenous matrices containing bioavailable chondroitin suplhate" Biomaterials 1999, 20: 847-858.

P.B. van Wachem et al. "In vivo biocompatability of carbodiimide-crosslinked collagen matrices: Effects of crosslink density, heparin immobilization, and bFGF loading" J. Biomed. Mater. Res. 2001, 55 (3): 368-378.

Kyumin Whang "A biodegradable polymer scaffold for delivery of osteotropic factors" Biomaterials 2000, 21 (24): 2545-2551.

J.S. Pieper et al. Attachment of glycosaminoglycans to collangenous matrices modulates the tissue response in rats, Biomaterials 2000, 21 (16): 1689-1699.

Kristen Billiar et al. "Effects of carbodiimide crosslinking conditions on the physical properties of laminated intestinal submucosa", J. Biomed. Mater. Res. 2001, 51(1): 101-108.

Toshimitsu Momose et al. "Surface modification of extrasynovial tendon by chemically modified hyaluronic acid coating" J. Biomed. Mater. Res. 2002, 59: 219-224.

Handbook of Biodegradable Polymers Hardwood Press 1997 (251-272).

Cohn et al., "Biodegradable PEO/PLA block copolymers," Journal of Biomedical Materials Research, 1988, 22 (993-1009).

"Polymer Preprints" (ACS Division of Polymer Chemistry), 1989. 30 (1): 498.

The Encyclopedia of Polymer Science, 1988 (13) 31-41.

"Handbook of Biodegradable Polymers" Hardwood Press 1997 (161-182).

"Handbook of Biodegradable Polymers" Hardwood Press 1997 (99-118).

Disilvestro et al., "Effects of Cross-Linking on the Mechanical Properties of a Porous Foam Scaffold of Small Intestine Submucosa", Society for Biomaterials 29th Annual Meeting Transactions, 2003, pp. 88.

Allman et al., "The Th2-Restricted Immune Response to Xenogeneic Small Intestinal Submucosa Does Not Influence Systemic Protective Immunity to Viral and Bacterial Pathogens", Tissue Engineering, vol. 8, No. 1, 2002, pp. 53-62.

Ide et al., "Collagen Hybridization with Poly(I-Lactic Acid) Braid Promotes Ligament Cell Migration", Mater. Sci. Eng. C, 17(1-2), 95-99 (2001).

Bercovy et al., "Carbon-PGLA Prosthesis for Ligament Reconstruction Experimental Basis and Short Term Results in Man", Clin. Orthop. Relat. Res., (196), 159-68 (1985).

Zhu et al, "Immobilization of Biomacromolecules onto Aminolyzed Poly(L-lactic acid) toward Acceleration of Endothelium Regeneration", Tissue Engineering, v 10, pp: 53-61, 2004.

Cheng & Teoh, "Surface modification of ultra thin poly (ÿ caprolactone) films using acrylic acid and collagen", Biomaterials, v25(11), pp: 1991-2001, 2004.

Wan et al., "Cell adhesion on gaseous plasma modified poly-(L-lactide) surface under shear stress field", Biomaterials, v24(21), pp: 3757-3764, 2003.

Yang et al., "Effect of surface treatment on the biocompatibility of microbial polyhydroxyalkanoates", Biomaterials, v 23 (5), pp: 1391-1397, 2002.

Croll et al., "Controllable surface modification of Poly(lactic-co-glycolic acid) (PLGA) by hydrolysis or aminolysis I: physical, chemical, and theoretical aspects", Biomacromolecules, Mar.-Apr. 2004, 5(2): 463-473.

Kwon et al., "Fibroblast culture on surface-modified poly (glycolide-co-ÿ-caprolactone) scaffold for soft tissue regeneration", J. Biomater Sci Polym ed. 2001, 12(10) 1147-60.

Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, Feb; 17(2).

Tan W, Krishnaraj R, Desai TA "Evaluation of nanostructured composite collagen-chitosan matrices for tissue engineering", Tissue Eng Apr; 7(2): 203-210, 2001.

Arnoczky SP "Building a meniscus", Biological considerations, Clin Orthop Oct; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18 (11), pp. 33-39, 2003.

Zhang et al., Design of nanostructured biological materials through self-assembly of peptides and proteins, MIT Current Opinion in chemical Biology, 2002, 6:865-871.

Hodde and Hiles, "Bioactive FGF-2 in sterilized extracellular matrix", Wounds, 13(5): 195-201 (2001).

O'Meara, Patrick, "The basic science of meniscus repair," Orthopaedic review, Jun. 1993, pp. 681-686.

Clearfix screw advertisement, 1998, Innovasive devices, Inc.
Winters and Justin, "Clearfix meniscal screw", Innovasive devices, Inc. 1998.
Surgical dynamics, meniscal stapler advertisement, 1997.
Bionix implants, Meniscus arrow advertisement, 1996.
Instrument makar, inc., Meniscus mender II, 1989.
William G. Clancy, Jr., M.D., and Ben K. Graf, M.D., "Arthroscopic Meniscal Repair", ACUFEX Microsurigal Inc., advertisement, 1988.
Dix et al., "Myosin mRNA Accumulation and Myofibrillogenesis at the Myotendinous Junction of Stretched Muscle Fibers", The Journal of Cell Biology, vol. 111, Nov. 1990, pp. 1885-1894.
De Deyne, Ph.D., MPT et al., "The Adaptation of Perimuscular Connective Tissue During Distraction Osteogenesis", Clinical Orthopaedics and Related Research, No. 379, pp. 259-269.
Kannus et al., "The effect of immobilization on myotendinous junction: an ultrastructural, histochemical and immunohistochemical study", Acta Physical Scandinavica, vol. 144, pp. 387-394.
Tidball, Ph.D. et al., "Myotendinous Junction Injury in Relation to Junction Structure and Molecular Composition", Exercise & Sport Sciences Reviews, vol. 19, 1991, pp. 419-445.
Wikipedia online definition of "hyaluronic acid" at http://en.wikipedia.org/wiki/Hyaluronate.
Michael W. King, Ph.D, online article entitled "Extracellular Matrix (ECM)", at http://web.indstate.edu/thcme/mwking/extracellular matrix.html.
Owen, et al., "Calcification Potential of Small Intestinal Submucosa in a Rat Subcutaneous Model" Journal of Surgical Research 71, 179-186 (1997).
Fan et al., "A composite coating by electrolysis-induced collagen self-assembly and calcium phosphate mineralization", *Biomaterials, Elsevier Science Publishers BV*, XP004670973, vol. 26, No. 14, May 14, 2005, pp. 1623-1632.
Marino et al., "The effect of electric current on rat tail tendon collagen in solution", *Calcified Tissue Research*, XP009066270, vol. 4, No. 4, 1970, pp. 330-338.
Marino et al., "Piezoelectricity in collagen films", *Calcified Tissue International*, XP009066271, vol. 31, No. 3, 1980, pp. 257-259.
Miller et al., "Electric field-assisted assembly of type-I collagen for applications in biomedical micro-systems", *Proceedings of IMECE 2005, 2005 ASME Int'l Mech. Engr. Cong. and Expo.*, XP009065904, Nov. 2005, pp. 1-3.
Niyibizi et al., "Human Placenta Type V Collagens Evidence for the Existence of an Alpha-1-V-Alpha-2-V-Alpha-3-V Collagen Molecule ", *Journal of Biological Chemistry*, XP002380121, vol. 259, No. 22, 1984, pp. 14170-14174.
Ma et al., "Synthetic nano-scale fibrous extracellular matrix", *Journal Biomedical Matererials Research*, XP002380122, vol. 46, No. 1, 1999, pp. 60-72.
Sarikaya et al., "AntiMicrobial Activity Associated with Extracellular Matrices", *Tissue Engineering*, vol. 8, No. 1, 2002, pp. 63-71.

William G. Clancy, Jr., M.D., and Ben K. Graf, M.D., "Arthroscopic Meniscal Repair", ACUFEX Microsurgical, inc., advertisement, 1988.
Instrument maker, inc., Meniscus mender II, 1989.
Winters and Justin, "Clearfix meniscal screw", Innovative devices, Inc., 1998.
Arnoczky SP "Building a meniscus", Biological considerations, Clin Orthop Oc; 367 (suppl), S244-53, 1999.
Gastel Ja Muirhead Wr, Lifrak JT, Fadale PD, Hulstyn MJ, Labrador DP "Meniscal tissue regeneration using a collagenous biomaterial derived from porcine small intestine submucosa", Arthroscopy, Feb.; 17(2).
Rodkey et al., "A clinical study of collagen meniscus implants to restore the injured meniscus", Clin. Orthop., 1999, 49(367 Suppl.), pp. S281-S292.
Stone et al., "Regeneration of meniscal cartilage with use of a collagen scaffold—Analysis of Preoliminary data", J. Bone Joint Surg., Am., 1997, 79(12), pp. 1770-1777.
Spaans et al., "Solvent-free fabrication of micro-porous polyurethane amide and polyurethane-urea scaffolds for repair and replacement of the knee-joint meniscus", Biomaterials, 2000 21(23), pp. 2453-2460.
de Groot et al., "Use of porous polyurethanes for meniscal reconsutrction and meniscal prostheses", Biomaterials, 1996, 17(2), pp. 163-173.
Klompmaker et al., "Meniscal replacement using a porous polymer prosthesis: a preliminary study in the dog.", Biomaterials, 1996, 17(12), pp. 1169-1175.
Siegel et al., "Meniscal allografts", Clin Sports Med., 1993, 12(1), pp. 59-80.
Boss et al., "Technical innovative: creation of a peripheral vascularized trough to enhance healing in cryopreserved meniscal allograft reconstruction", Knee Surg Sports Traumatol Arthrosc., 2000, 8(3), pp. 159-162.
Sweigart et al., "Toward tissue engineering of the knee meniscus", Tissue Eng., 2001, 7(2), pp. 111-129.
Rodeo, "Meniscal allografts—where do we stand?", Am. J. Sports Med., 2001, 29(2), pp. 246-261.
Stollsteimer et a., "Meniscal allograft transplantation: a 1- to 5-year follow-up of 22 patients", Arthroscopy, 2000, 16(4), pp. 343-347.
Rodeo, "Arthroscopic meniscal repair with use of the outside-in technique", Instr. Course Lect., 2000, 49 pp. 195-206.
Nehrer et al., 1997, "Matrix collagen type and pore size influence behavior of seeded canine chondrocytes," Biomaterials, 18(11), pp. 769-776.
European Search Report From Corresponding EPO Application No. 02752331.5-1219, Dated Jul. 10, 2007, 10 Pages.
European Search Report From Corresponding EPO Application No. 02752290.3-1219, Dated Mar. 26, 2007, 13 Pages.

* cited by examiner

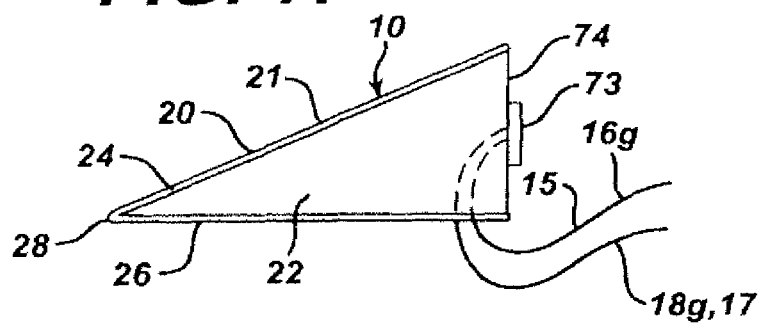
FIG. 11
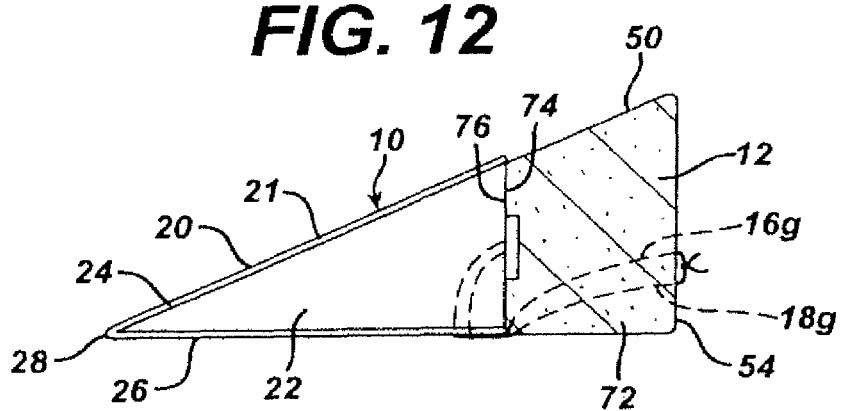
FIG. 12
FIG. 13
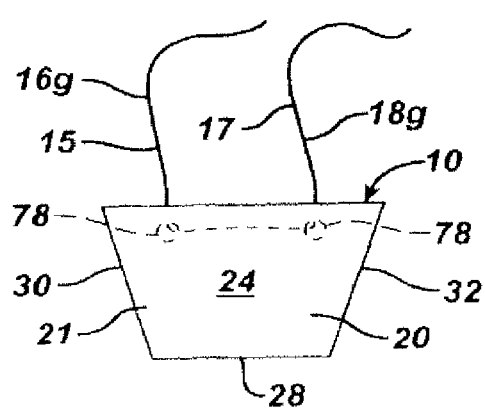
FIG. 14
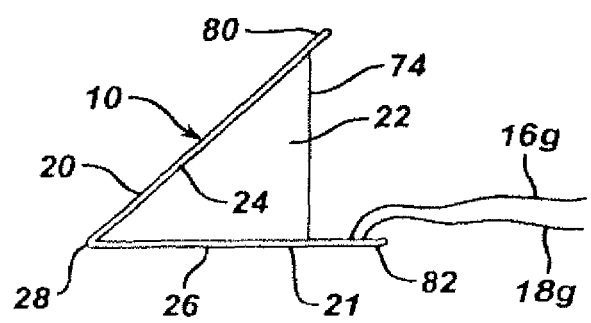

UNITARY SURGICAL DEVICE AND METHOD

This application claims the benefit of U.S. Provisional Application No. 60/305,786, filed on Jul. 16, 2001, U.S. Provisional Application No. 60/388,951, filed on Jun. 14, 2002, and U.S. application Ser. No. 10/195,344, filed on Jul. 15, 2002, all of which are incorporated by reference herein in their entireties.

CROSS REFERENCE

Cross reference is made to copending U.S. patent application Ser. No. 10/195,794 entitled "Meniscus Regeneration Device and Method"; Ser. No. 10/195,719 entitled "Devices from Naturally Occurring Biologically Derived Materials"; Ser. No. 10/195,347 entitled "Cartilage Repair Apparatus and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; and Ser. No. 10/195,633 entitled "Porous Delivery Scaffold and Method", each of which is assigned to the same assignee as the present application, each of which is filed concurrently herewith, and each of which is hereby incorporated by reference. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is hereby incorporated by reference.

FIELD OF THE INVENTION

The present invention relates generally to surgical devices for approximating, repairing or regenerating damaged or diseased fibrocartilage, and to surgical methods using such devices.

BACKGROUND OF THE INVENTION

Articular cartilage is a type of hyaline cartilage that lines the surfaces of the opposing bones in a diarthrodal joint (e.g. knee, hip, shoulder, etc.). Articular cartilage provides a near frictionless articulation between the bones, while also functioning to absorb and transmit the compressive and shear forces encountered in the joint. Further, since the tissue associated with articular cartilage is aneural, these load absorbing and transmitting functions occur in a painless fashion in a healthy joint.

Human joints also have another type of cartilage present: intra-articular fibrocartilage. Intra-articular fibrocartilage can be present in the form of a discus articularis, that is, as a plate or ring of fibrocartilage in the joint capsule separating the joint surfaces (articular cartilage) of the bones of the joint. Such fibrocartilage is present, for example, in the temporomandibular joint, between vertebrae, and in the knee joint. In the knee joint, the intra-articular fibrocartilage comprises the meniscus, a crescent-shaped or semi-lunar-shaped disc of tissue that is located between the femoral condyles and the tibial plateau. The meniscus primarily functions as a shock absorber, absorbing the shock of compressive and shear forces in the knee. The meniscus also provides a substantially frictionless surface for articulation of the knee joint.

When cartilage tissue is no longer healthy, there can be debilitating pain in the joint. Cartilage health can be adversely affected by disease, aging, or trauma. The adverse effects of disease, aging and trauma can be in the form of a tear in the cartilage or in the form of a breakdown of the cartilage matrix.

In the knee, the meniscus is frequently damaged in twisting injuries. It is also damaged with repetitive impact over time. Meniscus degeneration can also occur by aging; as a person ages, the meniscus can become soft in places, so that even common motions like squatting can cause meniscal tears.

Common surgical procedures for treating meniscal damage include tear repairs and meniscectomies. A tear repair is most commonly performed when the tear is a clean longitudinal vertical lesion in the vascular red zone of the meniscus. The basic strategy is to stabilize the tear by limiting or eliminating radial separation of the faces of the tear when the meniscus is load bearing. Many devices and surgical procedures exist for repairing meniscal tears by approximating the faces of the meniscus at the tear. Examples of such devices and procedures are disclosed in the following U.S. Pat. Nos. 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976.

Meniscectomies involve the surgical removal of part of the meniscus. Such procedures have generally been performed in cases of radial tears, horizontal tears, vertical longitudinal tears outside the vascular zone, complex tears, or defibrillation. Although meniscectomies provide immediate relief to the patient, in the long term the absence of part of the meniscus can cause cartilage wear on the condylar surface, eventually leading to arthritic conditions in the joint.

U.S. Pat. No. 6,042,610 assigned to ReGen Biologics, Inc., hereby incorporated by reference, discloses the use of a collagen scaffold device comprising a bioabsorbable material made at least in part from purified natural fibers. The purified natural fibers are cross-linked to form the device of that patent. The device produced can be used to provide augmentation for a damaged meniscus. Related U.S. Pat. Nos. 6,042,610; 5,735,903; 5,681,353; 5,306,311; 5,108,438; 5,007,934; 4,880,429 also disclose a meniscal augmentation device for establishing a scaffold adapted for ingrowth of meniscal fibrochondrocytes.

It is also known to use naturally occurring extracelluar matrices (ECMs) to provide a scaffold for tissue repair and regeneration. One such ECM is small intestine submucosa (SIS). SIS has been described as a natural biomaterial used to repair, support, and stabilize a wide variety of anatomical defects and traumatic injuries. See, for example, Cook® Online News Release provided by Cook Biotech Inc. at "www.cookgroup.com". The SIS material is derived from porcine small intestinal submucosa that models the qualities of its host when implanted in human soft tissues. Further, it is taught that the SIS material provides a natural matrix with a three-dimensional structure and biochemical composition that attracts host cells and supports tissue remodeling. SIS products, such as OASIS™ and SURGISIS™, are commercially available from Cook Biotech Inc., Bloomington, Ind.

Another SIS product, RESTORE® Orthobiologic Implant, is available from DePuy Orthopaedics, Inc. in Warsaw, Ind. The DePuy product is described for use during rotator cuff surgery, and is provided as a resorbable framework that allows the rotator cuff tendon to regenerate. The RESTORE Implant is derived from porcine small intestine submucosa, a naturally occurring ECM composed primarily of collagenous proteins, that has been cleaned, disinfected, and sterilized. Other biological molecules, such as growth factors, glycosaminoglycans, etc., have also been identified in SIS. See:

Hodde et al., Tissue Eng., 2(3): 209-217 (1996); Voytik-Harbin et al., J. Cell. Biochem., 67: 478-491 (1997); McPherson and Badylak, Tissue Eng., 4(1): 75-83 (1998); Hodde et al., Endothelium 8(1): 11-24; Hodde and Hiles, Wounds, 13(5): 195-201 (2001); Hurst and Bonner, J. Biomater. Sci. Polym. Ed., 12(11): 1267-1279 (2001); Hodde et al., Biomaterial, 23(8): 1841-1848 (2002); and Hodde, Tissue Eng., 8(2): 295-308 (2002). During seven years of preclinical testing in animals, there were no incidences of infection transmission from the implant to the host, and the SIS material has not adversely affected the systemic activity of the immune system. See: Allman et al., Transplant, 17(11): 1631-1640 (2001); Allman et al., Tissue Eng., 8(1):53-62 (2002).

While small intestine submucosa is available, other sources of ECM are known to be effective for tissue remodeling. These sources include, but are not limited to, stomach, bladder, alimentary, respiratory, and genital submucosa. In addition, liver basement membrane is known to be effective for tissue remodeling. See, e.g., U.S. Pat. Nos. 6,379,710, 6,171,344, 6,099,567, and 5,554,389, hereby incorporated by reference. Further, while ECM is most often porcine derived, it is known that these various ECM materials can be derived from non-porcine sources, including bovine and ovine sources. Additionally, the ECM material may also include partial layers of laminar muscularis mucosa, muscularis mucosa, lamina propria, stratum compactum layer and/or other such tissue materials depending upon other factors such as the source from which the ECM material was derived and the delamination procedure.

The following patents, hereby incorporated by reference, disclose the use of ECMs for the regeneration and repair of various tissues: U.S. Pat. Nos. 6,379,710; 6,187,039; 6,176,880; 6,126,686; 6,099,567; 6,096,347; 5,997,575; 5,993,844; 5,968,096; 5,955,110; 5,922,028; 5,885,619; 5,788,625; 5,733,337; 5,762,966; 5,755,791; 5,753,267; 5,711,969; 5,645,860; 5,641,518; 5,554,389; 5,516,533; 5,460,962; 5,445,833; 5,372,821; 5,352,463; 5,281,422; and 5,275,826.

SUMMARY OF THE INVENTION

The present invention is directed toward devices and surgical methods for the repair and regeneration of diseased or damaged intra-articular fibrocartilage such as the meniscus in the human knee joint.

In one aspect, the present invention provides a unitary surgical device for implantation in a patient for repairing a body tissue in the patient. The unitary surgical device comprises first and second biocompatible anchors and biocompatible tissue repair material extending between and connected to the first and second anchors. The anchors and tissue repair material are connected to each other prior to surgery. The first anchor includes at least one of the following: a bioresorbable barbed dart; a bioresorbable tack; a bioresorbable backstop; and a bioresorbable male locking member. The second anchor includes at least one of the following: a bioresorbable barbed dart; a bioresorbable tack; a bioresorbable backstop; and a bioresorbable female locking member. The biocompatible tissue repair material includes at least one of the following: a fixed length of suture; a sheet of collagen-containing material; laminar ECM material; formed ECM material; comminuted ECM material; ECM fibers; ECM foam material; a sheet of bioresorbable material; and a base connected to the first anchor and to the second anchor and a different material secured to the base, at least one of the base and the different material including ECM material.

In another aspect, the present invention provides a unitary surgical device for surgical implantation in a patient for regenerating intra-articular fibrocartilage tissue in the patient. The unitary surgical device comprises a first fixating mechanism, a second fixating mechanism and tissue repair material extending between and connected to the first and second fixating members prior to surgery. The first fixating mechanism includes at least one of the following: a length of suture; a bioresorbable barbed dart; a bioresorbable tack; a bioresorbable backstop; and a bioresorbable male locking member. The second fixating mechanism includes at least one of the following: a length of suture; a bioresorbable barbed dart; a bioresorbable tack; a bioresorbable backstop; and a bioresorbable female locking member. The tissue repair material includes at least one of the following: a sheet of ECM material connected to the first anchor and the second anchor; laminar ECM material connected to the first anchor and the second anchor; ECM foam; comminuted ECM; ECM fibers; cross-linked ECM material; formed ECM material; and a bioresorbable base connected to the first anchor and the second anchor and a different material on the base, where at least one of the base and the different material includes ECM.

In another aspect, the present invention provides a unitary surgical device for surgical implantation in a patient for regenerating intra-articular fibrocartilage tissue in the patient. The unitary surgical device comprises a base having at least two layers and a length of suture disposed or positioned between the layers of the base. At least part of the unitary surgical device is made from ECM material.

In another aspect, the present invention provides a unitary surgical device for surgical implantation in a patient for regenerating meniscal tissue in the patient. The unitary surgical device comprises a base having two panels. The two panels have a V-shaped configuration in cross-section, and meet along an apex portion. The two panels have end portions spaced distally from the apex portion. The end portions are spaced from each other to provide a gap. The unitary surgical device may also include tissue regeneration material between the two panels of the base. The unitary surgical device also includes opposing anchors on the end portions of the base panels. The opposing anchors are suitable for fixation to the native meniscus.

In another aspect, the present invention provides a unitary surgical device for surgical implantation in a patient for regenerating tissue in the patient. The unitary surgical device comprises a base made of a bioresorbable polymer and ECM material on the base. In addition, the unitary surgical device includes a first fixating member secured to the base prior to surgery. The first fixating member is suitable for fixation to the patient's tissue.

In another aspect, the present invention provides a unitary surgical device for surgical implantation in a patient for regenerating tissue in the patient. The unitary surgical device comprises a base made of ECM material and a first fixating member secured to the base prior to surgery. The first fixating member is suitable for fixation to the patient's tissue.

In another aspect, the present invention provides a unitary surgical device for surgical implantation in a patient for regenerating tissue in the patient. The unitary surgical device comprises a base having two opposing edges and a plurality of holes along one of the edges of the base. The unitary surgical devices includes ECM material.

In another aspect, the present invention provides a method of repairing a tear in the meniscus in the knee of a patient. The meniscus has an articulating surface and a non-articulating surface. The tear results in the meniscus having two inner surfaces. The method comprises the acts of providing a unitary surgical device having a pair of resorbable anchors and a fixed length of suture connected to the anchors. After the tear in the meniscus is located, the unitary surgical device is implanted to approximate the two inner surfaces of the meniscus at the tear, with suture extending across the articulating surface of the meniscus across the tear and the resorbable anchors being spaced from the tear.

In another aspect, the present invention provides a method of repairing a damaged meniscus in the knee of a patient. The meniscus has a non-articulating surface, a peripheral rim and an inner portion. The method comprises the acts of providing a wedge-shaped unitary surgical device including a fixating mechanism. A portion of the damaged meniscus inward of the peripheral rim of the meniscus is removed. The unitary surgical device is implanted with a portion inward of the peripheral rim. The unitary surgical device is fixated to the meniscus by fixating at least part of the base of the unitary surgical device to the meniscus with the fixating mechanism.

BRIEF DESCRIPTION OF THE DRAWINGS

The invention will be better understood by reference to the figures of the drawings wherein like numbers denote like parts throughout and wherein:

FIG. 11 is an elevation of a fifth embodiment of a unitary surgical device of the present invention;

FIG. 12 is a cross-section of a meniscus, after a partial meniscectomy, showing the unitary surgical device of FIG. 11 fixated to the meniscus and at least partially filling the void left by the partial meniscectomy;

FIG. 13 is a top plan view of a sixth embodiment of a unitary surgical device of the present invention;

FIG. 14 is an elevation of the unitary surgical device of FIG. 13;

DETAILED DESCRIPTION OF THE ILLUSTRATED EMBODIMENTS

Figure 1:
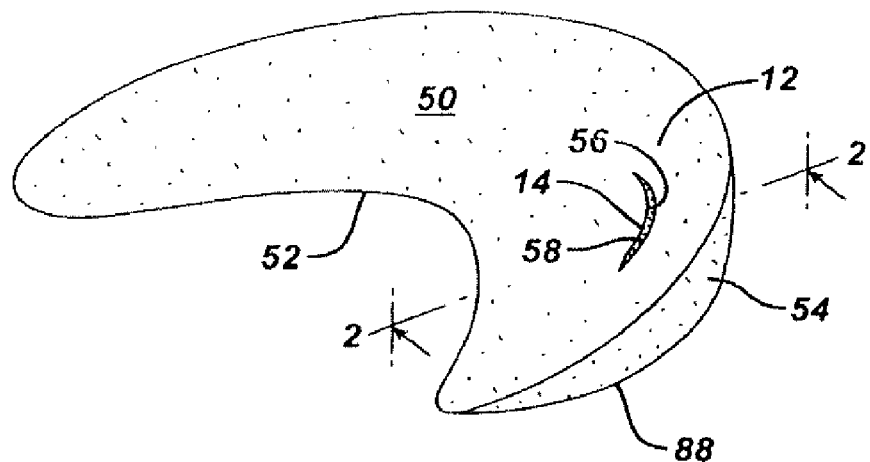
FIG. 1 is a diagrammatic perspective view of a meniscus with a tear.

A variety of unitary surgical devices 10 utilizing the principles of the present invention are illustrated in the accompanying drawings. The illustrated surgical devices 10 are for implantation in a patient for repairing a body tissue in the patient. The illustrated embodiments would most commonly be used in repairing intra-articular fibrocartilage, such as the meniscus of the knee, although the invention is not so limited unless expressly called for in the claims. A meniscus, or part of a meniscus, is diagrammatically illustrated at 12 in the accompanying drawings (FIGS. 1-2, 4, 6, 8, 10, 12, 15-17, 19, 21, 24-26, 29, 31, 33, 36, 38, 40, 46-49, 51 and 52). An example of a meniscal tear is shown at 14 in FIGS. 1-2, 4, 6, 8, 10, 46, 47 and 51. The invention is also expected to be useful in the treatment of damaged and diseased intra-articular fibrocartilage in other body parts as well.

As used herein "unitary" refers to the fact that the surgical devices 10 include at least one fixating element 15 and at least one tissue repair element 20, as an integral unit, prior to the time that the surgical devices are implanted in the patient. Preferably, each unitary surgical device 10 also includes a second fixating element 17. Thus, for example, suture may be incorporated into the device prior to the time the device is implanted in the patient. However, it should be understood that although at least one of each element is included in the device, the surgeon may choose to use additional material during surgery. For example, the surgeon may opt during surgery to use an additional fixating mechanism that was not an integral part of the original device, if the surgeon believes that additional stabilization is necessary or desirable.

As used herein, "tissue repair element" and "tissue repair material" are intended to include materials such as suture, whether of natural or synthetic origin, as well as tissue or cartilage regeneration material. Tissue or cartilage regeneration material encompasses naturally occurring extracellular matrix (ECM) materials that provide a collagen scaffold for tissue repair and regeneration. One such ECM material that may be used for the tissue or cartilage regeneration material is submucosa, and small intestine submucosa (SIS) in particular. Other bioremodelable collagenous tissue matrices, whatever the source, are intended to be included within "tissue regeneration material", including purified collagenous tissues. As used herein, "SIS" is intended to include small intestine submucosa unless otherwise limited. Moreover, as used herein, "ECM" is intended to include all SIS, as well as materials made from the other sources of submucosa identified above (e.g., bladder, stomach and liver tissue from bovine, ovine and porcine sources) and materials derived from liver basement membrane (from whatever source) unless otherwise limited. For the purposes of this invention, it is within the definition of a naturally occurring ECM to clean, delaminate, and/or comminute the ECM, to cross-link the collagen within the ECM, and to form a foam or other structure from the ECM. It is also within the definition of naturally occurring ECM to fully or partially remove one or more components or subcomponents of the naturally occurring matrix. However, it is not within the definition of a naturally occurring ECM to extract or separate and purify the natural components or subcomponents (e.g., collagen or growth factor) and reform a matrix material from these extracted and purified components or subcomponents. Also, while reference is made to SIS, it is understood that other naturally occurring ECMs such as stomach, bladder, alimentary, respiratory, and genital submucosa, and liver basement membrane, for example, whatever the source (e.g., bovine, porcine, ovine, etc.) are within the scope of this invention. Thus, in this application, the terms "naturally occurring extracellular matrix" or "naturally occurring ECM" are intended to refer to extracellular matrix material that has been cleaned, disinfected, sterilized, and optionally cross-linked. The terms "naturally occurring ECM" and "naturally occurring extracellular matrix" are also intended to include foam material made from naturally occurring ECM as described in copending U.S. patent application Ser. No. 10/195,354 entitled "Porous Extracellular Matrix Scaffold and Method", the toughened material made from naturally occurring ECM as described in U.S. patent application Ser. No. 10/195,794 entitled "Meniscus Regeneration Device and Method", and the hardened material made from naturally occurring ECM as described in U.S. patent application Ser. No. 10/195,719 entitled "Devices from Naturally Occurring Biologically Derived Materials", all filed concurrently herewith as U.S. Provisional Patent Applications and incorporated by reference below.

As used herein, bioresorbable, resorbable and bioabsorbable are intended to be interchangeable. All three terms are intended to mean materials that are naturally degradable in vivo over time. All are intended to include both natural and man-made materials, and to include new materials as they are developed, unless a specific material or type of material is identified in the claims.

As used herein, "intra-articular fibrocartilage" is intended to include the meniscus in the knee joint. It is also intended to include fibrocartilage separating the joint surfaces (articular cartilage) of the bones of other joints and separating the surfaces of adjacent vertebrae. "Intra-articular fibrocartilage" thus includes, for example, fibrocartilage in the temporomandibular joint and between vertebrae. Although the embodiments of the invention illustrated in FIGS. 11-23, 25-42, 44-47 and 53 are shaped for use in the meniscus, it should be understood that the principles of the present invention may be applied to surgical devices to be used in repairing and regenerating damaged or diseased intra-articular fibrocartilage in other joints in the body.

ECM material, and combinations of ECM material and synthetic materials, for use in the present invention can be prepared as described in the following United States patents, utility applications for United States patents, and provisional applications for United States patents, the disclosures of which are incorporated by reference herein: U.S. Pat. No. 4,902,508, entitled "Tissue Graft Composition"; U.S. Pat. No. 4,956,178, entitled "Tissue Graft Composition"; U.S. Pat. No. 5,281,422, entitled "Graft for Promoting Autogenous Tissue Growth"; U.S. Pat. No. 5,372,821, entitled "Graft for Promoting Autogenous Tissue Growth"; U.S. Pat. No. 5,445,833, entitled "Tendon or Ligament Graft for Promoting Autogenous Tissue Growth"; U.S. Pat. No. 5,733,337, entitled "Tissue Repair Fabric"; U.S. Pat. No. 5,788,625, entitled "Method of Making Reconstructive SIS Structure for Cartilaginous Elements In Situ"; U.S. Pat. No. 5,922,028, entitled "Multi-layered SIS Tissue Graft Construct for Replacement of Cartilaginous Elements In Situ"; U.S. Pat. No. 5,955,110, entitled "Multilayered Submucosal Graft Constructs and Method for Making the Same"; U.S. Pat. No. 5,993,844, entitled "Chemical Treatment, Without Detergents or Enzymes, of Tissue to Form an Acellular collagenous Matrix"; U.S. Pat. No. 6,176,880, entitled "Tissue Graft Construct for Replacement of Cartilaginous Structures"; Publication No. US-2002-0038151-A1, published Mar. 28, 2002, entitled "Reinforced Small Intestine Submucosa"; Publication No. US-2001-0002446-A1, published May 31, 2001, entitled "Tissue Graft Construct for Replacement of Cartilaginous Structures"; U.S. patent application Ser. No. 09/767, 346, filed Jan. 23, 2001, entitled "Tissue Graft Construct for Replacement of Cartilaginous Structures"; U.S. Provisional Application Ser. No. 60/305,786, entitled "Meniscus Regeneration Device and Method", filed on Jul. 16, 2001.

The "ECM" for use in the present invention can be disinfected as described in U.S. Pat. No. 6,206,931, entitled "Graft Prosthesis Materials" or U.S. Pat. No. 5,460,962, entitled "Peracetic Acid Sterilization of Collagen or collagenous Tissue," which are incorporated by reference herein in their entireties, or may be disinfected generally through the use of a disinfecting agent such as a 0.15% peracetic acid in 20% ethanol solution.

As described above, ECM material as used herein includes commercially available materials, unless otherwise expressly limited. Such commercially available materials include those available from DePuy Orthopaedics, Inc. of Warsaw, Ind. (e.g., RESTORE® Orthobiologic Implant), for example.

It should also be understood that "ECM" materials, including "SIS", as used herein, are not limited to the materials or processes described in the preceding paragraphs unless expressly indicated otherwise; the patents, provisional applications, utility applications and commercial products identified in the preceding paragraphs are identified for purposes of illustration only.

Referring now to the illustrated embodiments of the present invention, one group of unitary surgical devices 10 is illustrated in FIGS. 3-10 and 50-52. As illustrated in FIGS. 3, 5, 7, 9 and 50, each unitary surgical device 10 of this group includes two fixating elements 15, 17: a first anchor 16 and a second anchor 18. Each unitary surgical device also includes tissue repair material 20 extending between and connected to the first anchor 16 and second anchor 18. The tissue repair material 20 is connected to the two fixating members 15, 17 prior to surgery, and prior to terminal sterilization of the unitary surgical devices. In this group, the tissue repair material 20 comprises suture. A second group of unitary surgical devices 10 is illustrated in FIGS. 11-23, 25-40, 42 and 44-49. As illustrated in FIGS. 11, 13, 15, 18, 20, 22, 23, 27, 28, 30, 34, 35, 37, 39, 44, 45 and 50, each illustrated unitary surgical device 10 of this group also includes two fixating elements 15, 17 and tissue repair material 20 extending between and connected to the fixating members 15, 17. In this second group, the tissue repair material 20 includes a tissue regeneration material 22; the tissue repair material 20 may also include other elements such as suture or a base 21. In addition, in this second group, although the fixating elements 15, 17 may include anchors 16, 18, the fixating elements may also include suture, either alone or in combination with the anchors 16, 18. Thus, the fixating members 15, 17 may comprise: one or more anchors 16, 18; one or more anchors 16, 18 combined with suture 16g, 18g; or suture 16g, 18g alone. All of these elements in the second group are secured together prior to surgery and prior to terminal sterilization of the unitary surgical devices.

Figure 4:
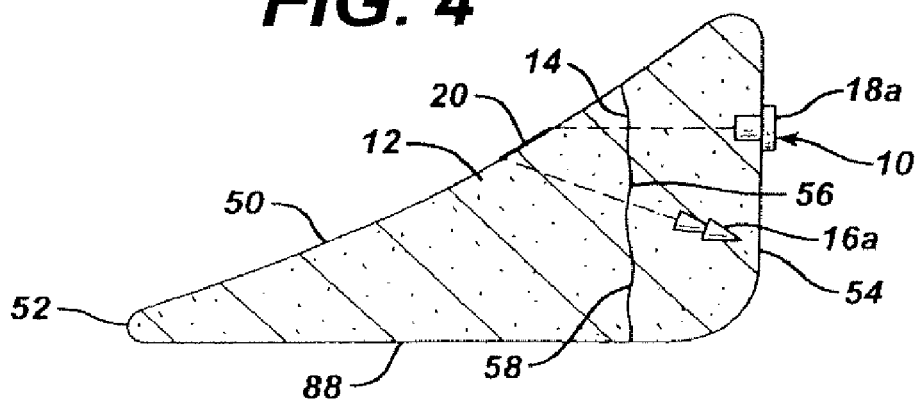
FIG. 4 is a cross-section of a torn meniscus showing the unitary surgical device of FIG. 3 fixated to the meniscus.
Figure 5:
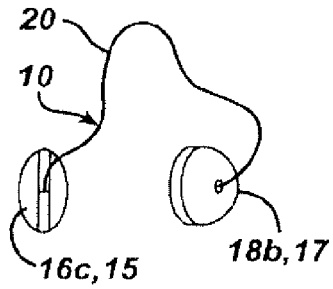
FIG. 5 is a perspective view of a second embodiment of a unitary surgical device of the present invention.
Figure 6:
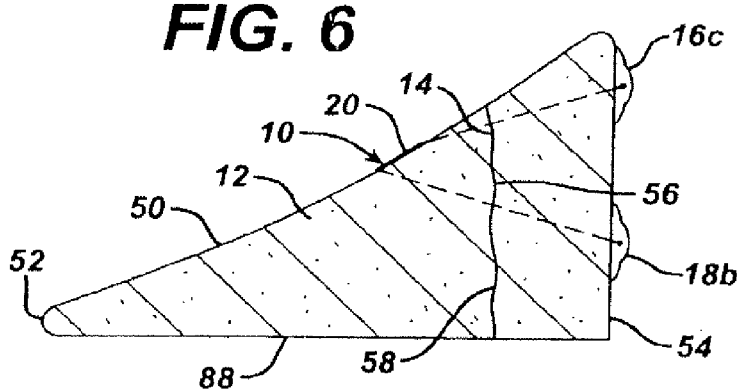
FIG. 6 is a cross-section of a torn meniscus showing the unitary surgical device of FIG. 5 fixated to the meniscus.
Figure 7:
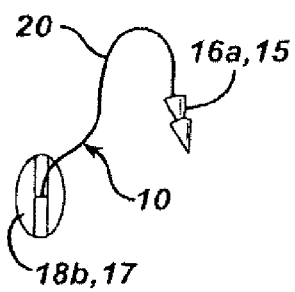
FIG. 7 is a perspective view of a third embodiment of a unitary surgical device of the present invention.
Figure 8:
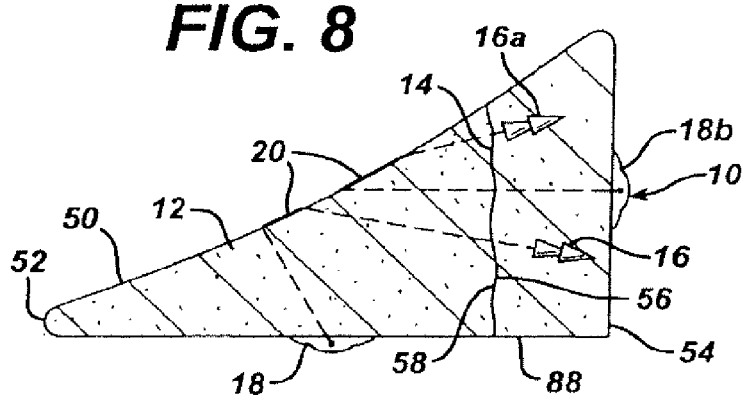
FIG. 8 is a cross-section of a torn meniscus showing the unitary surgical device of FIG. 7 fixated to the meniscus.
Figure 9:
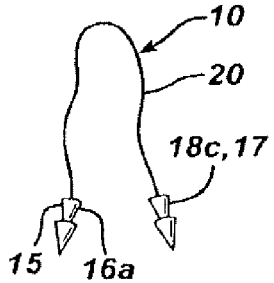
FIG. 9 is a perspective view of a fourth embodiment of a unitary surgical device of the present invention.
Figure 10:
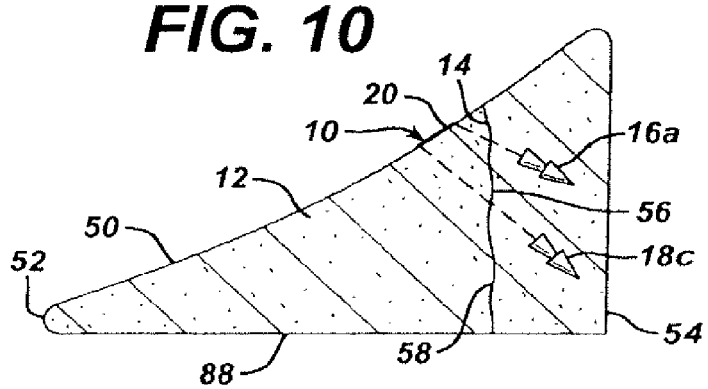
FIG. 10 is a cross-section of a torn meniscus showing the unitary surgical device of FIG. 9 fixated to the meniscus.
Figure 34:
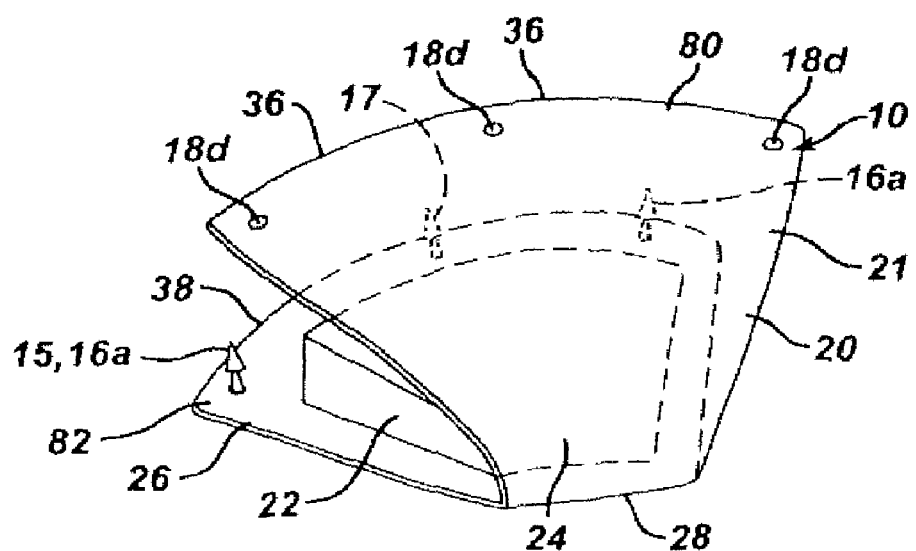
FIG. 34 is a perspective view of a fifteenth embodiment of a unitary surgical device incorporating the teachings of the present invention.
Figure 35:
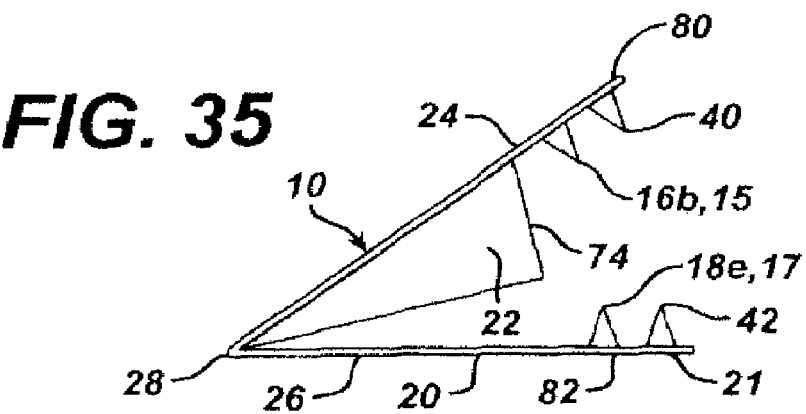
FIG. 35 is an elevation of a sixteenth embodiment of a unitary surgical device incorporating the teachings of the present invention.
Figure 36:
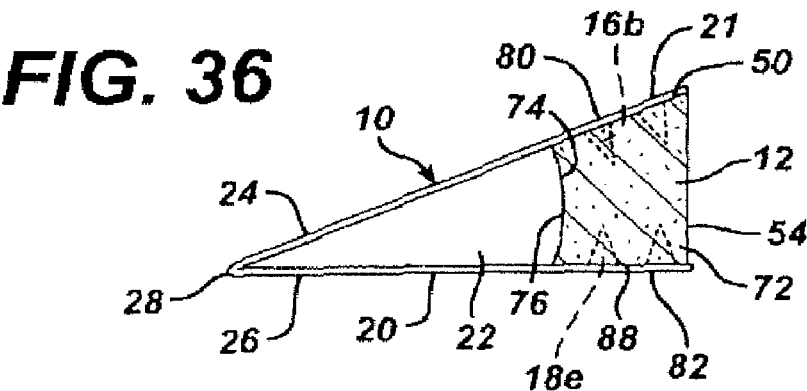
FIG. 36 is a cross-section of a meniscus, after a partial meniscectomy, showing the unitary surgical device of FIG. 35 fixated to the meniscus and at least partially filling the void left by the partial meniscectomy.
Figure 37:
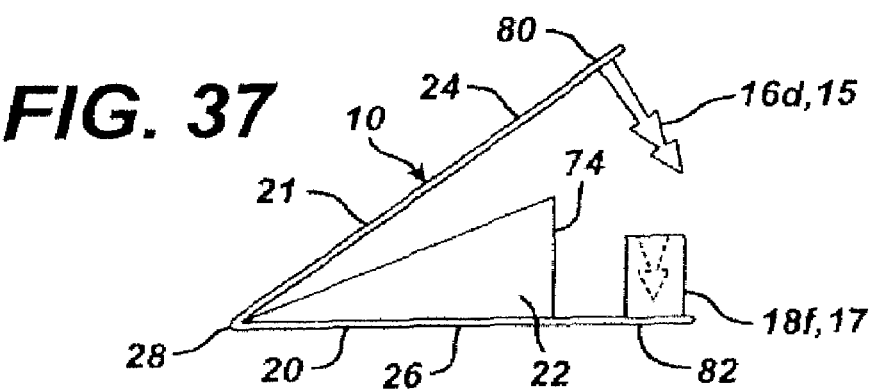
FIG. 37 is an elevation of a seventeenth embodiment of a unitary surgical device incorporating the teachings of the present invention.
Figure 38:
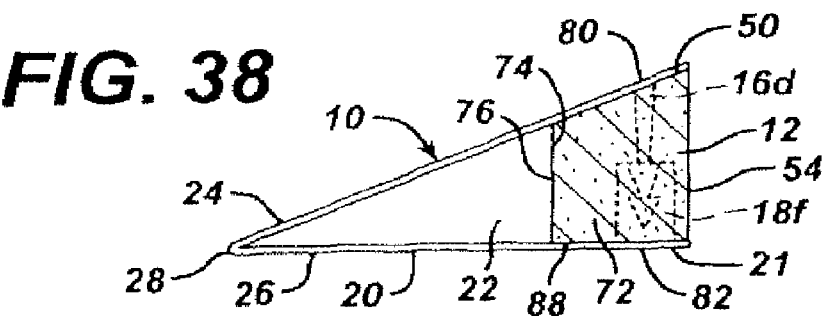
FIG. 38 is a cross-section of a meniscus, after a partial meniscectomy, showing the unitary surgical device of FIG. 37 fixated to the meniscus and at least partially filling the void left by the partial meniscectomy.
Figure 39:
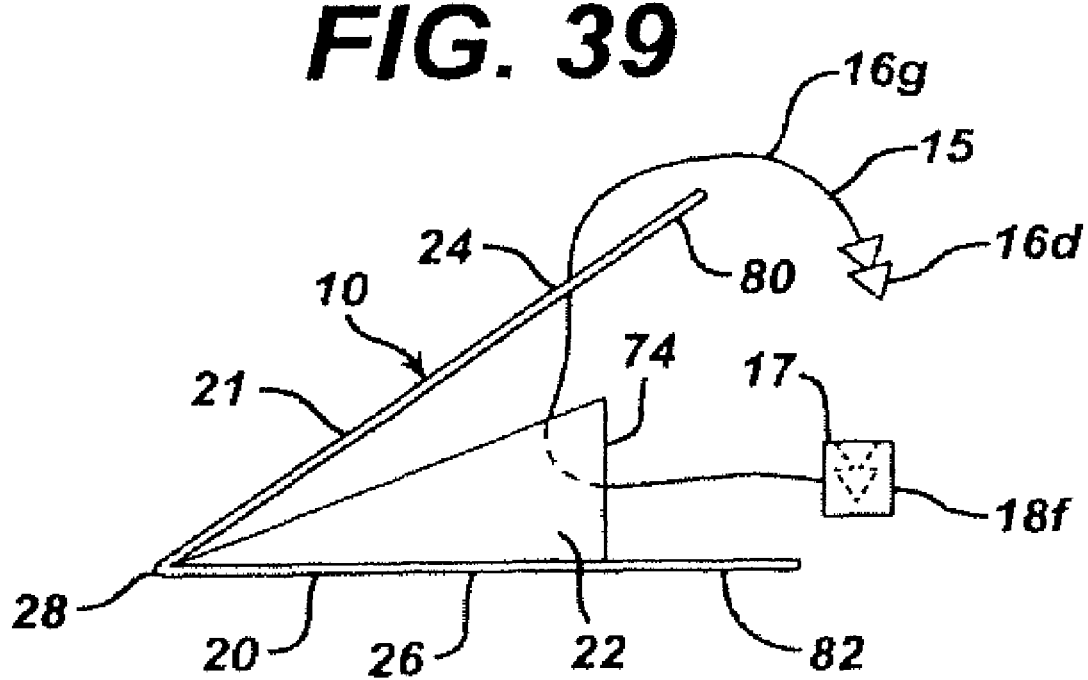
FIG. 39 is an elevation of an eighteenth embodiment of a unitary surgical device incorporating the teachings of the present invention.
Figure 40:
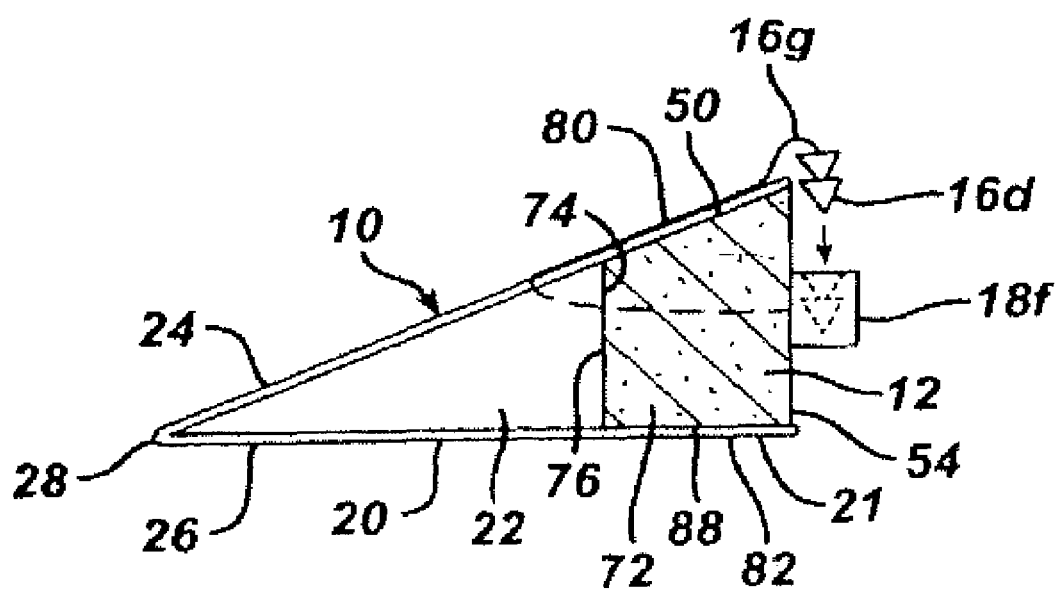
FIG. 40 is a cross-section of a meniscus, after a partial meniscectomy, showing the unitary surgical device of FIG. 39 fixated to the meniscus and at least partially filling the void left by the partial meniscectomy.

In both groups of devices, where at least one of the fixating members 15, 17 includes an anchor, the anchor 16 may comprise: a barbed dart, as illustrated at 16a in FIGS. 3-4, 7-8, 9-10, 30-34 and 50-52; a tack, as illustrated at 16b in FIGS. 35-36; a backstop, as illustrated at 16c in FIG. 5-6; a male locking member, as illustrated at 16d in FIGS. 37-40; or a pair of connected anchors such as the pair of barbed darts 16a connected by a length of suture. The first fixating member 15 may also comprise a length of suture, as shown at 16g in FIGS. 11-15, 17-23, 25-26, 28-29, 42 and 44. The first fixating member 15 may also comprise combinations of anchors and other materials, such as a combination of a barbed dart 16a as an anchor and a length of suture 16g, as shown in FIGS. 30-31 and 46-47, or a combination of a male locking member 16d and a length of suture 16g, as shown in FIGS. 39-40, for example. Whatever form of fixating member is selected, each material in the illustrated embodiments is a biocompatible and bioabsorbable one, that is, one that will eventually be broken down, assimilated, diminuted or excreted, or both assimilated and diminuted or excreted by the body of the patient. If a second fixating member 17 is used, it may include a second anchor 18. The second anchor 18 may comprise a top hat-shaped fixating member, as illustrated at 18*a* in FIGS. 3-4; a backstop, as illustrated at 18*b* in FIGS. 5-8; barbed dart, as illustrated at 18*c* in FIGS. 9-10, 27, 30-31 and 50-51; a receiving opening, as shown at 18*d* in FIG. 34; a tack, as illustrated at 18*e* in FIGS. 35-36; a female locking member, as illustrated at 18*f* in FIGS. 37-40. The second fixating member 17 may also comprise a length of suture, as shown at 18*g* in FIGS. 13-23, 25-26, 28-29, 42 and 44-45. The second fixating member 17 may also comprise combinations of materials, such as a combination of an anchor 18 such as a barbed dart 18*c* and a length of suture 18*g*, as shown in FIGS. 30-31 and 46-47, for example. As in the case of the first fixating member 15, whatever structure or form is selected for the second fixating member 17, each material in the illustrated embodiments is a biocompatible and bioabsorbable one.

Figure 3:
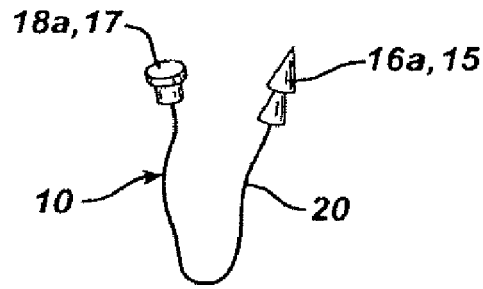
FIG. 3 is a perspective view of a first embodiment of a unitary surgical device of the present invention.

In unitary surgical devices 10 using two fixating members 15, 17, various combinations of the above-described anchors 16*a*-16*g*, 18*a*-18*g* can be used. For example, two anchors may be used of the same or different shape, such as: a barbed dart 16*a* with a top hat-shaped structure 18*a*, as shown in FIGS. 3-4; a barbed dart 16*a* with another barbed dart as shown at 16*a* and 18*c* in FIGS. 9-10; a barbed dart with a backstop, as shown at 16*a* and 18*b* in FIGS. 7-8; a tack 16*b* can be used with another tack 18*e*, as shown in FIGS. 35-36, or with some other structure. All of these combinations may be used with suture as the tissue repair material 20 in the first group of embodiments, and all of them may be used with the second group of embodiments as well. It should be understood that these combinations are identified for purposes of illustration only. The present invention is not limited to these combinations unless expressly set forth in the claims.

A variety of materials may be used for the first and second anchors 16, 18. For example, the anchors may be constructed of biocompatible polymers, bioremodelable collagenous matrices and combinations of such materials. Other materials, such as bioactive agents, other biologically derived agents, biocompatible inorganic materials, cells, and biological lubricants can also be included as part of the anchors.

As used herein, "biocompatible polymer" and "biocompatible polymers" is intended to include both synthetic polymers and biopolymers (e.g., collagen). Examples of biocompatible polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, copolymer or mixture of polymers or co-polymers that are utilized in the construction of prosthetic implants. If other such polymers have therapeutic value in the orthopaedic field, it is anticipated that at least some of them will have use in the present invention, and at least some of them should be included in "biocompatible polymers." In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

"Bioremodelable collagenous tissue matrix" and "naturally occurring bioremodelable collagenous tissue matrix" are intended to include matrices derived from native tissue selected from the group comprising skin, artery, vein, pericardium, heart valve, dura mater, ligament, bone, cartilage, bladder, liver, stomach, fascia and intestine, whatever the source. Although "naturally occurring bioremodelable collagenous tissue matrix" is intended to refer to matrix material that has been cleaned, processed, sterilized, and optionally crosslinked, it is not within the definition of a naturally occurring bioremodelable collagenous tissue matrix to extract and purify the natural components or subcomponents (e.g., collagen) and reform or reconstitute a matrix material from purified natural components or subcomponents.

It is understood and intended that there is substantial overlap between "bioremodelable collagenous tissue matrices" and "extracellular matrices"; the different expressions are used in this specification and claims to ensure complete coverage of the invention. It is believed that the teachings of the present invention will be useful for materials falling with both definitions.

Some commercially available products may be used as the anchors 16, 18 in some of the illustrated embodiments. For example, the backstop elements shown at 16*c*, 18*b* and 19 in FIGS. 5-8, 45, 47 and 50-52 and top-hat-shaped element 18*a* shown in FIGS. 3-4 may be taken from the RAPIDLOC™ Meniscal Repair System available from the MITEK® Products division of ETHICON, INC. of Westwood, Mass.

In addition, the anchors 16*a*-16*f*, 18*a*-18*f* may be constructed from a naturally occurring material such as naturally occurring extracellular matrices (ECM), such as small intestine submucosa (SIS). In such a case, each anchor 16*a*-16*f*, 18*a*-18*f* may be configured as a monolithic structure formed from naturally occurring ECM which is cured to be rigid and hardened. As such, it should be appreciated that the ECM material from which the anchor is fabricated is cured to produce a structure that possesses the necessary hardness and toughness to be inserted into and through the native meniscus and to be retained in the native meniscus for at least a predetermined period of time.

ECM material with the necessary hardness and toughness for use as the anchors may be fabricated by compacting comminuted or shredded naturally occurring ECM material into bar or rod stock by compressing the material together and then curing the material such that it is very rigid and hardened. The curing may be accomplished by simple air drying or by heated air drying of the formed stock. The material may additionally be crosslinked to further improve its mechanical properties.

As a specific example, one or more of the anchors 16*a*-16*f*, 18*a*-18*f* may be constructed with a cured and hardened SIS. In this case, comminuted SIS material is placed in a container and allowed to air dry for a predetermined period of time (e.g., as long as several days) at room temperature. Over such a time, water evaporates from the SIS material thereby shrinking the material. The shrunk material is very tough and hard and, as a result, may be machined as described herein.

It should be appreciated that other process parameters may be established to facilitate the curing process. For example, a curing profile utilizing predetermined amounts of heat and/or pressure may be designed to facilitate the curing of the naturally occurring ECM material (e.g., SIS).

Once the ECM material (e.g., SIS) is cured to a desired hardness and toughness, it may be machined with conventional machining equipment to desired shapes such as in the shape of a barbed dart as illustrated in FIGS. 3-4, 7-10, 27, 30-33 and 46-47. For example, the anchor 16*a*-16*f*, 18*a*-18*f* may be turned on a lathe or similar equipment to produce the desired configuration of the anchor, such as the barbed darts. However, based on the specific design of the anchor, it should be appreciated that certain features of the anchor (e.g., the barbed darts) may be separately or additionally machined to produce a desired shape or geometry. For example, various barb configurations may be formed on part of the anchor, by, for example, use of a cutting machine.

In addition to conventional cutting machining techniques (e.g., lathing and cutting), contemporary techniques may also be utilized to form the cured naturally occurring ECM into the desired configuration of the anchor 16a-16f, 18a-18f. For example, a programmable laser cutting machine may be used to cut the raw stock of cured ECM. Specifically, the laser cutting machine may be programmed to cut the raw stock in a pattern which produces a desired configuration of the anchor. In addition to providing for cutting with precision tolerances, laser cutting also provides other benefits. Such laser cutting of the ECM can produce barbed darts having cut edges which are sealed and fused together to enhance the attachment capability of the barbed darts.

It should be understood that the material selected for the anchors 16a-16f, 18a-18f may also comprise mixtures or composites of the materials described above. For example, the anchors 16a-16f, 18a-18f could comprise both a biocompatible polymer and ECM material. With regard to the shape of the barbed darts 16a, 18c that may be used with the present invention, reference is made to barbed dart configuration shown in U.S. Pat. No. 5,702,463 as one example of a shape of barbed dart that may be useful. It should be understood that the shapes of the barbed darts 16a, 18c and other anchors 16b-16f, 18a-18b, 18d-18f shown in the accompanying drawings are provided for purposes of illustration only. The present invention is not limited to any particular shape of barbed dart or other anchor unless expressly set forth in the claims. It should also be understood that the sizes of the anchors in the drawings shown are provided for purposes of illustration only. The actual sizes of the anchors may be different from those illustrated, and may vary with the method used to implant them. For example, the commercially available backstop is inserted through a needle, as shown in the Mitek Products document "RAPIDLOC MENISCAL REPAIR SYSTEM, Surgical Technique for Repair of Meniscal Tears". If this technique and instrumentation is to be used to insert the anchors of the present invention, then the anchors should be sized accordingly. Typical barbed darts can be expected to be in the range of about 1 mm in maximum diameter and about 3 mm in length. It should be understood that these dimensions are provided for purposes of illustration only; the present invention is not limited to any particular size of anchor unless expressly set forth in the claims.

Where the fixating elements 15, 17 include or consist of suture 16g, 18g, such as in FIGS. 11-23, 25-31, 42 and 44, any suitable suture material may be used, such as commercially available suture. Acceptable suture may be obtained from the MITEK PRODUCTS division of ETHICON, INC. of Westwood, Mass.; examples include PANACRYL™ absorbable suture, ETHIBOND® EXCEL polyester suture, PDS® polydioxanone suture and PROLENE® polypropylene suture.

Whatever structure and material is chosen for the anchors 16, 18, the anchors are connected to a tissue repair material 20 in the illustrated unitary surgical devices 10. The tissue repair material 20 in the illustrated embodiments includes: suture; a base; tissue regenerating material; or combinations of these materials.

In the embodiments of FIGS. 3-10, the tissue repair material 20 comprises a fixed length of suture; the suture in the illustrated embodiment has a length of about 4-5 mm. A surgical kit could contain several unitary surgical devices 10, each with a pair of anchors 16, 18 separated by a variety of fixed lengths of suture 20 as the tissue repair material. The lengths for the sutures portions of the devices 10 in the kit could range, for example, from 2 mm to about 1 cm. Alternatively, several kits could be provided each with a plurality of unitary surgical devices of a particular length. It should be understood that these lengths are provided for purposes of illustration only; the present invention is not limited to tissue repair material of these or any particular lengths unless expressly called for in the claims. The suture used for the tissue repair material 20 in these embodiments may be standard commercially-available suture made of conventional materials. Acceptable suture may be obtained from the sources identified above. FIGS. 3-10 illustrate examples of such unitary surgical devices 10 wherein the tissue repair material 20 comprises suture.

Figure 41:
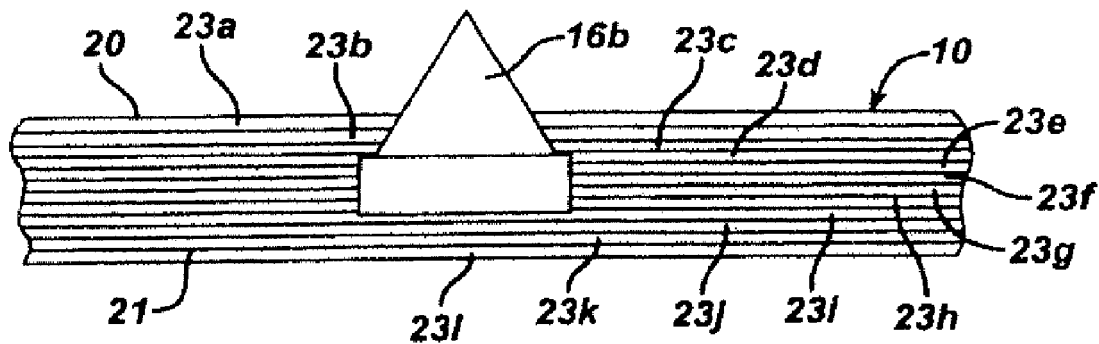
FIG. 41 is an enlarged cross-section through a part of a laminar base of a unitary surgical device, such as the device of FIG. 35, with an implanted tack used as one of the anchors of the device.
Figure 42:
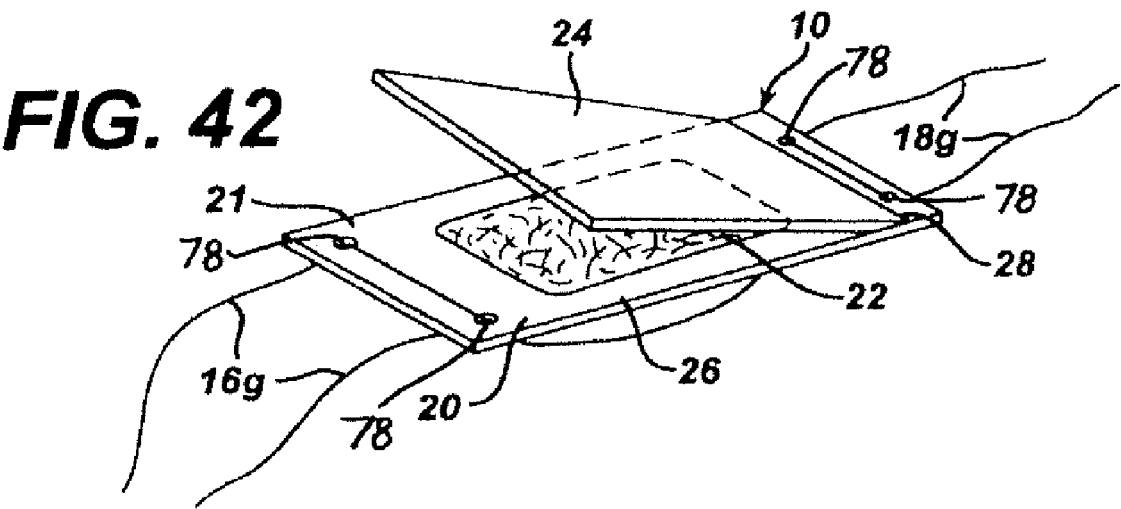
FIG. 42 is a perspective view of a nineteenth embodiment of a unitary surgical device incorporating the teachings of the present invention.
Figure 43:
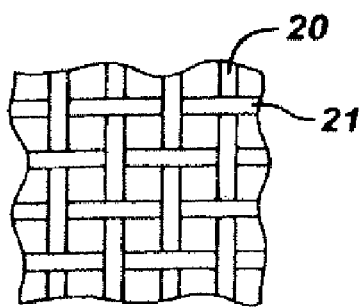
FIG. 43 is an enlarged plan view of a mesh used as the base of a unitary surgical device.

Embodiments of the invention utilizing a base 21 as part of the tissue repair material 20 are illustrated in FIGS. 11-23, 25-42, 44-47. The base component 21 of the tissue repair material may comprise a third fixating member, such as backstop element 19 shown in FIG. 50. In addition, the base 21 may provide structural support to the unitary surgical device 10. The base may comprise a sheet, as shown in FIGS. 11-23, 25-42, and 44-45, and may be a laminar sheet, as illustrated in FIG. 41. The base component may comprise a formed structure, as illustrated in FIG. 42. The formed structures could be laminar or could be formed in other manners as disclosed below. The base component 21 may also comprise one or more layers of mesh structures, for example, woven materials as illustrated in FIG. 43, non-woven materials, knitted materials, warp-knitted materials, braided materials, foamed materials and combinations of those materials; if more than one layer of a mesh structure is provided, the layers may be juxtaposed or spaced, with other material sandwiched between the layers, for example. The base material should have sufficient strength so that the connection to the anchors 16, 18 and the connection of the anchors 16, 18 to the patient's native tissue is maintained during implantation of the unitary surgical device 10 and for a suitable period of time after implantation. Generally, the base 21 should have sufficient strength for a sufficient time to allow the healing process to progress to the point where the structural stability provided by the base 21 is no longer needed. However, in the claims no particular strength should be implied the claims unless expressly recited.

The base 21 in any of the embodiments of FIGS. 11-23, 25-42, 44-47 could comprise a biocompatible polymer, a bioremodelable collagenous matrix, a naturally occurring ECM (and in particular SIS) or combinations of these materials. The tissue regeneration material 22 may be carried by the base 21 or may comprise the base 21. The base could also comprise these materials together with bioactive agents, other biologically derived agents, cells, a biological lubricant, or a biocompatible inorganic material. In the claims, no particular material or combination of materials should be implied for the base unless expressly recited.

For a base 21 made out of or including a biocompatible polymer, suitable polymers are defined above. These polymers can be provided in the form of, for example, meshes of woven or non-woven materials, laminar sheets, knitted materials, warp-knitted materials, braided materials, or one or more layers of foamed polymer. Reference is also made to the materials disclosed in copending U.S. Ser. No. 10/195,341 entitled "Hybrid Biologic/Synthetic Porous Extracellular Matrix Scaffolds", filed concurrently herewith, along with U.S. patent application Ser. No. 10/172,347 entitled "Hybrid Biologic-Synthetic Bioabsorbable Scaffolds" which was filed on Jun. 14, 2002, both of which are incorporated by reference herein in their entireties.

For a base 21 made out of or including ECM material, several options are available. The ECM could comprise material derived from a mammalian submucosa source, such as SIS. The ECM base could be formed as a laminate structure, as illustrated in FIG. 41. The layers may be laminated together and bonded by both mechanical compression and application of vacuum and/or heated air which accomplishes the bonding and also dries the product. Reference is made to U.S. Pat. No. 5,955,110, which is incorporated by reference herein in its entirety, for a description of a method of making layered SIS material. A suitable SIS base may also be formed as described in copending U.S. patent application Ser. No. 10/195,794 entitled "Meniscus Regeneration Device and Method", which is incorporated by reference herein in its entireties. A vacuum plate or platen with a cavity in a desired shape may be provided, with a vacuum pump connected to the cavity by a tube. The cavity may be provided with a plurality of openings leading to a manifold space within the platen which is connected to the pump. Several layers of naturally occurring ECM, such as SIS, are placed on the plate. These layers are preferably initially in a moist and flexible state. These moist, flexible layers are pulled down into the cavity by the vacuum to form a molded recess for receiving a mass of biological material. A flat vacuum plate or platen could also be used to form flat sheet forms of ECM material. These and other techniques may be employed to form the base into a desired shape, such as the wedge shape shown in FIGS. 11-23, 25-26 and 30-40.

Other sheet forms of ECM are expected to be useful to provide a base 21 or combination base 21 and tissue regeneration material 22. For example, it is anticipated that one could make a thick slurry of comminuted ECM fibers, dry the slurry into a sheet, pocket or other form, such as the form illustrated in FIG. 42, for example, and heat the material under combinations of pressure, vacuum and heat to bond and dry the product. In addition, one or more such sheets could be laminated together or with strips of ECM material. It is expected that other shapes and forms could also be formed of such materials. It is expected that other materials could be intermixed with the ECM material as well; for example, the thick slurry could include both ECM material and a biocompatible polymer as a structural reinforcement, or the slurry of ECM material could be supported on and fused with a supporting structure made of ECM or some biocompatible polymer.

In any of the above examples, the material for the base, such as ECM, can be crosslinked by known methods. For example, chemical or physical crosslinking can be used. Chemical crosslinking methods include the use of aldehydes, carbodiimides, glycation agents, enzymes or the like. Physical crosslinking methods include freeze-drying and fusion by physical means such as heat (thermal crosslinking), radiation (ultraviolet or gamma irradiation) or combinations such as by drying at elevated temperatures (dehydrothermal crosslinking). Crosslinking may also be used to impart to the base 21 biological lubricants such as hyaluronic acid (HA).

A portion or all of the base 21 may be perforated to allow easy chemical and cellular transfer. In addition, if desired, cells, bioactive agents, biologically derived agents, biological lubricants and biocompatible inorganic materials may be added to the base.

The base 21 may also include a foamed or hybrid structure, and may include other materials as disclosed in applications for United States patent filed concurrently herewith and previously filed, which are incorporated by reference herein in their entireties: U.S. patent application Ser. No. 10/172,347 entitled "Hybrid Biologic-Synthetic Bioabsorbable Scaffolds" which was filed on Jun. 14, 2002; Ser. No. 10/195,341 entitled "Hybrid Biologic/Synthetic Porous Extracellular Matrix Scaffolds" filed herewith; Ser. No. 10/195,606 entitled "Cartilage Repair and Regeneration Device and Method" filed herewith; and Ser. No. 10/195,354 entitled "Porous Extracellular Matrix Scaffold and Method" filed herewith.

Figure 27:
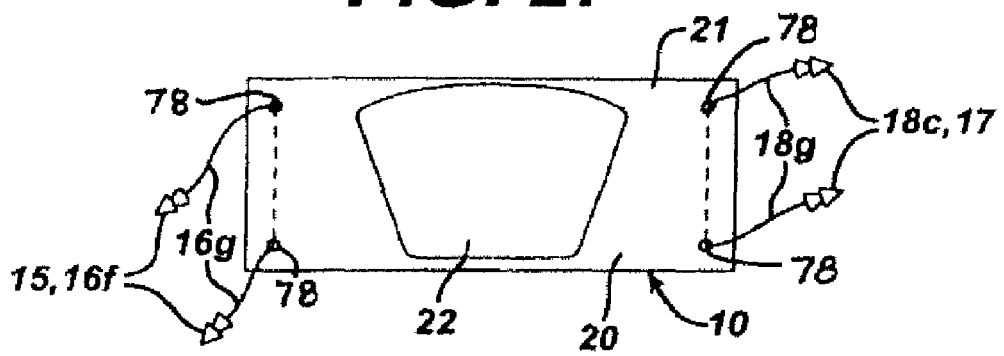
FIG. 27 is a top plan view of a tenth embodiment of a unitary surgical device incorporating the teachings of the present invention.
Figure 28:
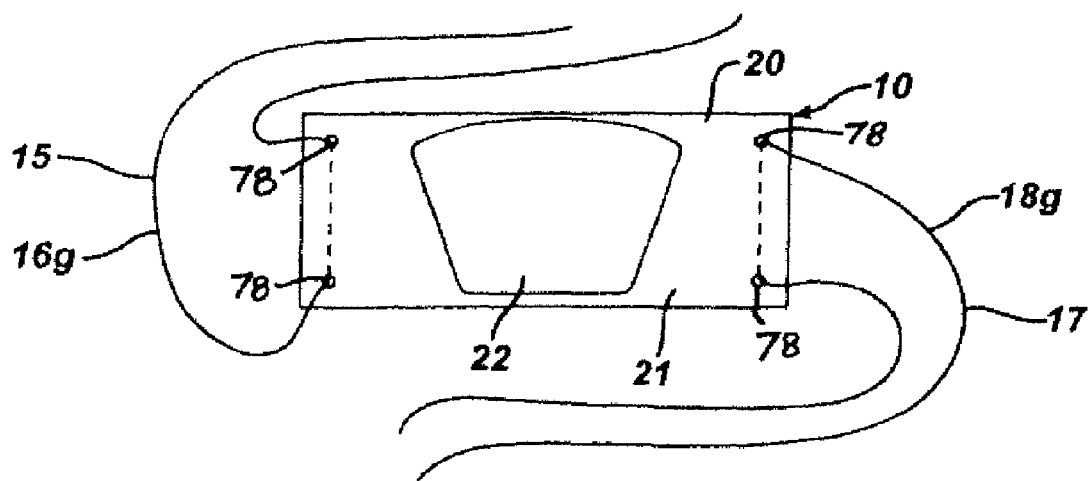
FIG. 28 is a bottom plan view of an eleventh embodiment of a unitary surgical device incorporating the teachings of the present invention.
Figure 29:
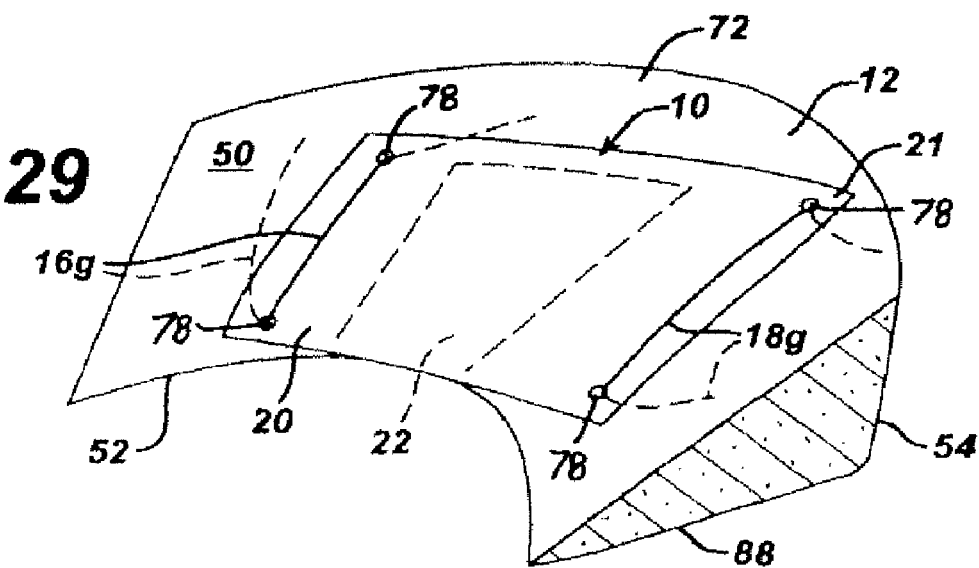
FIG. 29 is a perspective, partially cut-away view of a meniscus with the unitary surgical device of FIG. 27 fixated to the meniscus.

The base 21 may take any one of several shapes and configurations. For example, as illustrated in FIGS. 27-29, the base 21 may comprise a single substantially flat panel. As illustrated in FIGS. 10-23, 25-26 and 30-40, the base 21 may comprise two integral panels 24, 26 joined along a linear or curved apex 28; the two illustrated panels 24, 25 diverge outward from the apex 28 to define a wedge-shaped or V-shaped structure in cross-section. The side edges 30, 32 of each panel 24, 26 may also diverge outwardly from the apex 28, as shown in FIGS. 13, 18, 22-23 and 30. The base 21 may comprise a pillow-like structure, like a sac made of the base material, with a mass of tissue regeneration material held within the sac or pillow structure.

Figure 44:
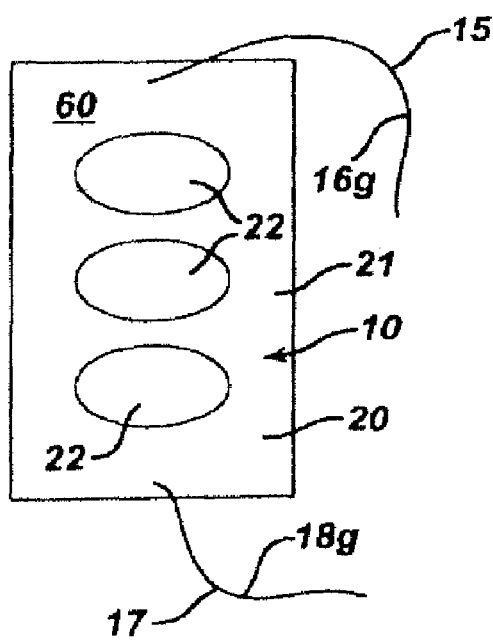
FIG. 44 is a top plan view of a twentieth embodiment of a unitary surgical device incorporating the teachings of the present invention.

In each of the embodiments of FIGS. 11-23, 25-40, 42 and 44-45, a mass of tissue regeneration material 22, such as ECM, is included as part of the tissue repair material 20. In each of these embodiments, the mass of tissue regeneration material 22 comprises a separate mass that is secured to the base 21. In the embodiment of FIG. 44, a plurality (three) of masses of tissue regeneration material 22 are fixed to the base 21. In the embodiments of FIGS. 11-23, 25-26 and 30-40, a single mass of tissue regeneration material 22 is positioned between the two panels 24, 26 near the apex 28; the masses of tissue regeneration material 22 in these illustrated embodiments are wedge-shaped or V-shaped in cross-section, although it should be understood that other shapes are within the scope of the invention. As illustrated in FIG. 42, the mass of tissue regeneration material could also comprise a loose pack of comminuted or shredded ECM material. As disclosed in U.S. Provisional Patent Application Ser. No. 60/305,786, the SIS material could comprise rolls of comminuted SIS. It should also be understood that, depending on the material used for the base 21, the unitary surgical device need not include any additional tissue regeneration material; for example, if the base 21 comprises one or more layers of ECM mesh or an ECM foam, then it may not be necessary to include a separate mass of tissue regeneration material.

If a separate mass of tissue regeneration material 22 is used, it may be secured to the base 21 by use of a compatible adhesive. Synthetic adhesives are commercially available, such as polycaprolactone (PCL. Biological adhesives are also available, such as commercially available materials containing transglutaminase or fibrin, for example. Other biological adhesives are also known, as described in U.S. Pat. No. 6,326,025 "Tissue Reactive Adhesive Compositions" and in published U.S. Pat. Apps. 200200344533 "Bioerodable Polymeric Adhesives for Tissue Repair" and 20020031551 "Bioerodable Polymeric Adhesives for Tissue Repair." The adhesive can be applied to the tissue regeneration material 22 and to the base 21. The tissue regeneration material 22 may be secured to a pillow or sac-like base by substantially enclosing the mass of tissue regeneration material within the base structure, such as by suturing three or four sides of the base structure around the mass of tissue regeneration material, by using a compatible adhesive around the perimeter of the base surrounding the mass of tissue regeneration material. The tissue regeneration material may also be secured to the base by positioning the tissue regeneration material in a formed receiving structure or pocket, as in the embodiment of FIG. 42. In addition, layers of SIS material could be laminated around all or part of the mass of tissue regeneration material. Chemical and physical cross-linking may also be used to secure the mass of tissue regeneration material 22 to the base 21. Chemical cross-linking methods of securing these materials 21, 22 together include the use of aldehydes, carbodiimides, glycation agents, enzymes (e.g., transglutaminase), biologics (e.g. fibrin) or the like. Physical cross-linking methods include freeze-drying and fusion by physical means such as heat (thermal cross-linking), radiation (ultraviolet or gamma irradiation) or combinations such as by drying at elevated temperatures (dehydrothermal cross-linking).

The mass or plug of tissue regeneration material 22 may comprise comminuted and/or lyophilized naturally occurring ECM (e.g., SIS) with the desired porosity and material density. The material density and/or porosity of the mass or plug may be varied to control cell migration and proliferation. Additional examples of materials that are usable for the mass of tissue regeneration material include ECM (e.g., SIS) powder, ECM (e.g., SIS) fibers, ECM (e.g., SIS) threads, ECM (e.g., SIS) mesh, ECM (e.g., SIS) wovens, ECM (e.g., SIS) non-wovens, ECM (e.g., SIS) braided materials, ECM (e.g., SIS) solutions, ECM (e.g., SIS) gel, ECM (e.g., SIS) paste, ECM (e.g., SIS) foam, and combinations of such materials. For the powder, solutions, gel and paste forms of SIS, the material may be prepared as described in U.S. Pat. No. 5,352,463, entitled "Tissue Graft for Surgical Reconstruction of a Collagenous Meniscus and Method Therefor", which is incorporated by reference herein in its entirety. It should be understood that separate reference in the above list to the forms of ECM should not be taken to imply that the listed references are exclusive; for example, ECM non-wovens, ECM threads and ECM foam may all include ECM fibers.

The mass or plug of tissue regeneration material 22, and the base 21, or the combination of the base and the tissue regeneration material may include materials described in U.S. Pat. No. 6,179,872 B1, entitled "Biopolymer Matt for Use in Tissue Repair and Reconstruction" and U.S. Pat. No. 6,153,292, entitled "Biopolymer Foams for Use in Tissue Repair and Reconstruction", which are both incorporated by reference herein in their entireties. The mass or plug of tissue regeneration material 22 and the base, or the combination of the base and the tissue regeneration material may include materials disclosed in the following copending and concurrently filed U.S. patent applications, which are incorporated by reference herein: Ser. No. 10/195,794 entitled "Meniscus Regeneration Device and Method"; Ser. No. 10/195,719 entitled "Devices from Naturally Occurring Biologically Derived Materials"; U.S. patent Ser. No. 10/195,347 entitled "Cartilage Repair Apparatus and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; and Ser. No. 10/195,633 entitled "Porous Delivery Scaffold and Method", along with U.S. patent application Ser. No. 10/172,347 entitled "Hybrid Biologic-Synthetic Bioabsorbable Scaffolds" which was filed on Jun. 14, 2002.

The mass of plug of tissue regeneration material 22 could also comprise other collagenous materials. For example, it is expected that a commercial product such as the Collagen Meniscus Implant made by ReGen Biologics, Inc. of Franklin Lakes, N.J. could be combined with other elements of the present invention to form a unitary surgical device. Other collagen scaffolds are described in the following U.S. Pat. Nos. 6,042,610; 5,735,903; 5,479,033; 5,306,311; 5,007,934; and 4,880,429.

Porous ECM (e.g., SIS) foam for the tissue regeneration material 22 may be fabricated by lyophilizing (i.e., freeze-drying) comminuted ECM (e.g., SIS) suspended in water. The material density and pore size of the resultant foam may be varied to fit the needs of the design by controlling, amongst other things, the rate of freezing of the comminuted ECM suspension and/or the amount of water in which the comminuted ECM is suspended at the on-set of the freezing process.

The following is a specific example of a process for fabricating an exemplary ECM foam. It should be understood that the present invention is not limited to the materials, devices, or process steps of the following example unless expressly called for in the claims. The first step in developing a foam with a desired pore size and density is the procurement of comminuted ECM. To do this, scissor-cut ECM runners (e.g., SIS runners about 6 inches long) are positioned in a 1700 series Comitrol™ machine which is commercially available from Urschel Laboratories of Valparaiso, Ind. The ECM material is processed and thereafter collected in a receptacle at the output of the machine. The material is then processed through the machine a second time under similar conditions. Water is introduced during the process, and the resultant material is a "slurry" of ECM fiber (thin, long fibers about 200 microns thick×1-5 mm long) suspended substantially uniformly in water. It should be understood that this size of ECM fiber is identified as an illustrative example only; the invention is not limited to a particular size of ECM fiber material unless the claims expressly call for a particular size.

Generally, the process parameters for the comminution process should be selected to produce ECM material that is capable of commingling, intermixing or intertwining, rather than producing a powder. Process parameters that can be varied using the above-identified 1700 series Comitrol™ machine include the choice of blade used, whether water is used, the amount of water used, the speed at which the blades turn and the number of times the material is passed through the machine. As an example, cutting head 140084-10 and a Vericut, sealed impeller from Urschel Laboratories may be used, with a flow of water of about two (2) gallons per minute, with the cutting head run at a constant speed of about 9300 rpm. A first pass through the machine at these parameters will produce fibrous ECM material of varying sizes, and a second pass will produce ECM fibers of more uniform size. To test the comminuted material to determine whether it is appropriate for the production of an ECM foam, the comminuted ECM suspension or slurry is then centrifuged, excess water is poured off and the remaining slurry is poured into a dish. By hand, a small amount of the comminuted ECM material in the dish is pinched between the thumb and index finger and gently lifted from the dish; if the comminuted SIS material is fibrous, at least a small amount of additional ECM, beyond the portion pinched between the thumb and index finger, will lift along with the material that has been pinched. This additional comminuted ECM material lifts with the material that is between the thumb and index finger because the individual pieces of comminuted ECM material are commingled or intertwined. Such material should be suitable for the production of a foam. It is expected that other shapes and sizes of ECM material, and mixtures of shapes and sizes of ECM material, may be useful in producing an ECM foam. For example, it is expected that one could comminute ECM to produce ECM flakes that can intermingle to form an appropriate slurry.

As used herein, unless the claims are otherwise expressly limited, the terms "cohesive ECM pieces" and "cohesive SIS pieces" are intended to include ECM and SIS material that has been comminuted or otherwise processed to produce ECM and SIS pieces that are capable of commingling or intertwining (in the wet or dry state) to form a cohesive mass of discrete elements, regardless of the shape or shapes of the individual ECM or SIS pieces. One method of demonstrating that the ECM material comprises cohesive pieces is the "pinch test" described above. Examination of the final ECM foam product produced may also provide evidence that the base material comprised cohesive ECM pieces.

As used herein, "pieces" is intended to include any fiber, strip, ribbon, sliver, filament, shred, bit, fragment, part, flake, slice, cut, chunk, or other portion of solid or solid-like material. "ECM fiber" and "SIS fiber" are also intended to include ECM and SIS material that has been comminuted or otherwise processed to produce a material wherein at least some of the individual pieces of ECM and SIS material have lengths greater than their widths and thicknesses. It should be understood that unless otherwise expressly limited by the claims, use of the terms "ECM pieces" and "SIS pieces" should be construed to mean that the material includes such pieces, but should not be considered to imply that the material consists of such pieces exclusively. Such terms should also not be construed to imply that any particular process has been used to produce the material.

After the suspension has been formed, the suspension of SIS fibers is dried. To do so, a lyophilization process (freeze drying) is used. In particular, the suspension of SIS fibers is frozen at a controlled temperature drop rate to control the size of the formed ice crystals. Without allowing the material to thaw, the process of lyophilization sublimes ice crystals directly to vapor under vacuum and low temperatures. This process leaves voids in the spaces previously occupied by ice crystals. These voids and the SIS fibrous material form a network of compartments with SIS material defining interconnected walls of the network compartments. One exemplary machine for performing such a freeze drying process is a Virtis Genesis™ Series lyophilizer which is commercially available from SP Industries, Inc. of Gardiner, N.Y.

The process parameters of the lyophilization process may be varied to produce foams of varying pore sizes and material densities. For example, to produce foams having a relatively small pore size and a relative high material density, the SIS fibrous material may be tightly compacted by removing the water in a substantially uniform manner so as to achieve a relatively high density. Thereafter, the SIS fibrous material is flash-frozen using liquid nitrogen prior to lyophilization of the SIS. To produce foams having a moderate pore size and a moderate material density, the SIS fibrous material is first tightly compacted by removing the water in a substantially uniform matter so as to achieve a relatively high density. Thereafter, the SIS is frozen at a relatively fast rate (e.g., $>-1°$ C./min.) to a temperature of about $-80°$ C. prior to lyophilization of the SIS.

As shown in the photomicrographs (FIGS. 1-3) in copending U.S. patent application Ser. No. 10/195,344 entitled "Porous Extracellular Matrix Scaffold and Method", filed by Prasanna Malaviya, Herbert Schwartz and Pamela Plouhar, the result of using the above-described process and materials is an ECM foam comprising a three-dimensional web of naturally occurring ECM defining a plurality of three-dimensional pores. The foam has three-dimensional pores throughout its height, width and thickness; the three-dimensional pores are interconnected to define a plurality of interconnected passageways. These interconnected passageways may be used for movement of cells such as chondrocytes in vivo. These interconnected passageways can also be used for the introduction of bioactive agents, biologically derived agents (e.g., stimulants), cells, biocompatible inorganic materials, biocompatible polymers and/or biological lubricants that may be combined with the foam as described below prior to implantation. The interconnected passageways defined by the three-dimensional pores also serve as passageways for materials used during the manufacturing process, such as compounds used for chemical cross-linking the foam.

The tissue regeneration material 22 may be chemically cross-linked with, for example, aldehydes, carbodiimides, glycation agents, enzymes (e.g., transglutaminase), biologics (e.g., fibrin) or the like. The tissue regeneration material 22 may also be physically cross-linked, by, for example: freeze-drying, heat fusion (thermal cross-linking), radiation fusion (ultraviolet or gamma irradiation) or combinations of fusion techniques such as by drying at elevated temperatures (dehydrothermal cross-linking).

The base 21 and/or the mass of tissue regeneration material 22 may also be impregnated with bioactive agents, biologically derived agents, cells, biocompatible polymers, biocompatible inorganic materials and biological lubricants. The materials could be crosslinked or otherwise affixed to the ECM base and/or mass. Alternatively, cells (e.g., fibrochondrocytes) may be cultured on the ECM base and/or mass, and as a result, subsequently be implanted as part of the unitary surgical device at the time of implantation. For the meniscus repair device, any such cells are preferably fibrochondrocytes or mesenchymal stem cells.

"Bioactive agents" include one or more of the following: chemotactic agents; therapeutic agents (e.g., antibiotics, steroidal and non-steroidal analgesics and anti-inflammatories, anti-rejection agents such as immunosuppressants and anti-cancer drugs); various proteins (e.g., short chain peptides, bone morphogenic proteins, glycoprotein and lipoprotein); cell attachment mediators; biologically active ligands; integrin binding sequence; ligands; various growth and/or differentiation agents (e.g., epidermal growth factor, IGF-I, IGF-II, TGF-$\beta$ I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; TGF$_\beta$ superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. If other such substances have therapeutic value in the orthopaedic field, it is anticipated that at least some of these substances will have use in the present invention, and such substances should be included in the meaning of "bioactive agent" and "bioactive agents" unless expressly limited otherwise. It should be understood that the above agents are identified by way of example only, and the present invention is not limited to any particular agent unless expressly called for in the claims.

"Biologically derived agents" include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin (autograft, allograft and xenograft); platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the present invention, and such substances should be included in the meaning of "biologically-derived agent" and "biologically-derived agents" unless expressly limited otherwise. It should be understood that the above agents are identified by way of example only, and the present invention is not limited to any particular agent unless expressly called for in the claims.

"Cells" include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. It should be understood that the above cells are identified by way of example only, and the present invention is not limited to any particular type of cell unless expressly called for in the claims.

"Biological lubricants" include: hyaluronic acid and its salts, such as sodium hyaluronate; glycosaminoglycans such as dermatan sulfate, heparan sulfate, chondroitin sulfate and keratan sulfate; synovial fluid and components of synovial fluid, including mucinous glycoproteins (e.g., lubricin), tribonectins, articular cartilage superficial zone proteins, surface-active phospholipids, lubricating glycoproteins I, II; vitronectin; and rooster comb hyaluronate. "Biological lubricant" is also intended to include commercial products such as ARTHREASE™ high molecular weight sodium hyaluronate, available in Europe from DePuy International, Ltd. of Leeds, England, and manufactured by Bio-Technology General (Israel) Ltd., of Rehovot, Israel; SYNVISC® Hylan G-F 20, manufactured by Biomatrix, Inc., of Ridgefield, N.J. and distributed by Wyeth-Ayerst Pharmaceuticals of Philadelphia, Pa.; HYLAGAN® sodium hyaluronate, available from Sanofi-Synthelabo, Inc., of New York, N.Y., manufactured by FIDIA S.p.A., of Padua, Italy; and HEALON® sodium hyaluronate, available from Pharmacia Corporation of Peapack, N.J. in concentrations of 1%, 1.4% and 2.3% (for ophthalmologic uses). If other such substances have therapeutic value in the orthopaedic field, it is anticipated that at least some of these substances will have use in the present invention, and such substances should be included in the meaning of "biological lubricant" and "biological lubricants" unless expressly limited otherwise. In addition, as new biological lubricants are identified or developed, it is expected that at least some of them will be useful materials for the present invention. It should be understood that the above materials are identified by way of example only, and the present invention is not limited to any particular material unless expressly called for in the claims.

"Biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphates, ceramic particles and combinations of such materials. If other such substances have therapeutic value in the orthopaedic field, it is anticipated that at least some of these substances will have use in the present invention, and such substances should be included in the meaning of "biocompatible inorganic material" and "biocompatible inorganic materials" unless expressly limited otherwise.

It is expected that various combinations of bioactive agents, biologically derived agents, cells, biological lubricants, biocompatible inorganic materials, biocompatible polymers can be used with the anchors, bases, and tissue repair material (including tissue regeneration material) of the present invention.

The unitary surgical devices 10 of FIGS. 11-23, 27-40 and 42 may be sized to fit the standard gap 70 left in the meniscus by a meniscectomy so that one unitary surgical device can be implanted to fill this gap 70. It may be desirable to make a plurality of sizes of such unitary surgical devices 10 to encompass the standard range of gaps 70 left by meniscectomies. In addition, it may be desirable to plan to be able to use more than one unitary surgical device 10 to fill the gap 70 left by the meniscectomy, so that a plurality of unitary surgical devices 10 may be implanted adjacent to or overlapping with one another to fill the gap 70 during the surgery.

To make a unitary surgical device 10 that includes two anchors 16, 18 connected by a length of suture as the tissue repair material 20, the anchors may be formed as described above. The anchors 16a-16g, 18a-18g may be formed to include, or machined to include an opening so that one end of each length of suture may be secured to one anchor. For example, the anchors 16, 18 could be tubular so that one end of suture can be threaded through each anchor and then knotted to secure them together. Or, the anchors could have a hole through which the suture end is threaded and then knotted.

Figure 30:
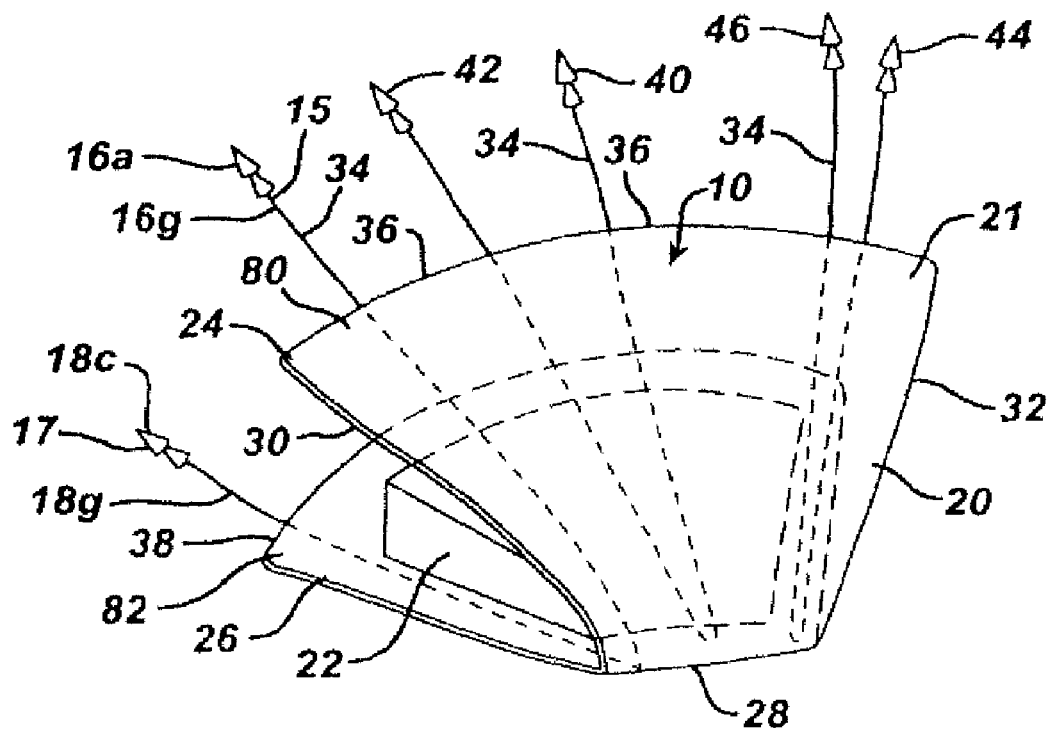
FIG. 30 is a perspective view of a thirteenth embodiment of a unitary surgical device incorporating the teachings of the present invention.
Figure 31:
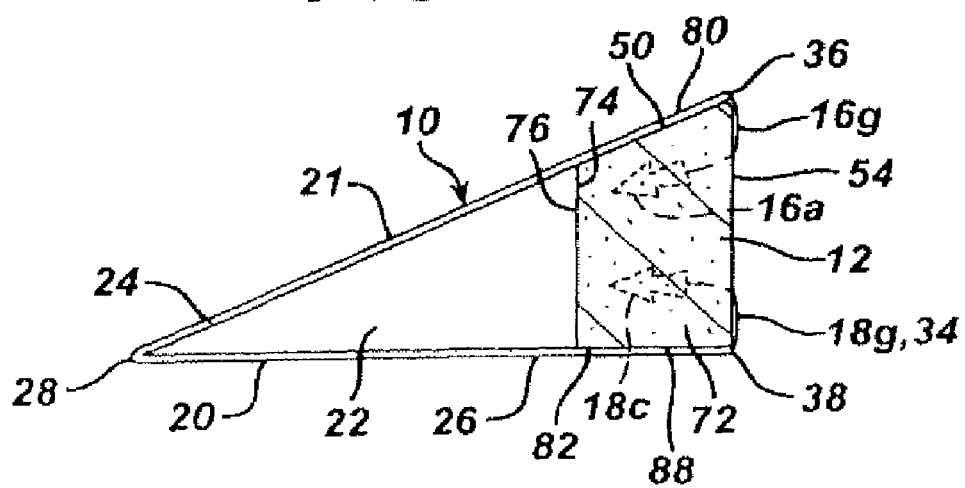
FIG. 31 is a is a cross-section of a meniscus, after a partial meniscectomy, showing the unitary surgical device of FIG. 30 fixated to the meniscus and at least partially filling the void left by the partial meniscectomy.

To make a unitary surgical device 10 that includes both a laminar base and suture, as in the embodiments of FIGS. 22-23, 25-26 and 30-31, threads of suture 34 may be placed between two layers of base material prior to completely forming the base so that the suture threads 34 become integral with the base 21 during the forming process. As illustrated, the lengths of the suture threads 34 should be great enough so that the suture ends extend substantially beyond the parallel end edges 36, 38 of the unitary surgical device to define the first fixating element 15 and second fixating element 17 at the opposite ends of the suture thread 34. As illustrated, a plurality of suture threads may be made integral with each base. In the embodiments of FIGS. 22-23 and 30-31, three long strands of suture 34 are used, so that the resulting unitary surgical device has a total of six fixating elements: the first fixating element 15, the second fixating element 17, a third fixating element 40, a fourth fixating element 42, a fifth fixating element 44, and a sixth fixating element 46. The three suture threads 34 for this embodiment may be aligned so that one length of suture is positioned along the longitudinal centerline of the base, and additional lengths of suture are positioned between the longitudinally-aligned thread and the long edges 30, 32 of the base 21, and aligned with the shape of the long edges 30, 32 of the base 21. The laminar base 21 may then be made as described in the provisional application with each suture thread 34 in place between two layers. The finished unitary surgical device 10 will include the suture affixed to the base. The base 21 of FIG. 22 may then be folded about axis 48 to form the wedge-shaped structure shown in FIG. 23, with the linear apex 28 at the axis 48. If desired, additional anchors such as barbs, tacks, or backstops, for example, could be secured to the free ends of the suture, as illustrated in the embodiment of FIGS. 30-31. It should be understood that fewer or more strands of suture may be used for the devices illustrated in FIGS. 22-23 and 30-31; for example, two strands of suture could be used, or four strands of suture could be used.

For non-laminar bases, the suture threads 34 could be positioned in or on the base material prior to final forming of the base. The base may then be formed as described above with the suture formed as an integral part of the base. In any case, suture could also be adhered to the base or could be sewn to the base.

To make the embodiments of FIGS. 34-38, an anchor such as a barb may be positioned on the surface of base laminates, as shown in FIG. 41, where anchor 16b is shown on layers 23i-23l of laminate. Then, additional layers, such as layers 23a-23h shown in FIG. 41, may be placed on the initial base laminate 23i-23l, surrounding part of the anchor 16b. The unitary surgical device may then be formed with the anchor 16b becoming secured to at least some of the layers of the base as the layers are dried, heated and compressed. Other forms of anchor can be positioned on the base during fabrication of the base so that completion of the base also secures the anchors to the base to form a unitary structure.

Any of the anchors could also be secured to the base after the base is formed by, for example, using an adhesive to secure the anchor to the base. Suitable adhesives for this purpose include commercially available materials such as those containing fibrin or transglutaminase. It should be understood that other methods for securing the anchors to the base are within the scope of this invention; the invention is not limited to any particular method of securing the elements together unless expressly called for in the claims.

All of the illustrated embodiments of the invention may be prepared for use in surgery by providing prepackaged unitary surgical devices or kits. Thus, for example, after making any of the illustrated embodiments of unitary surgical device, a single unitary surgical device can be packaged and terminally sterilized, so that the surgeon may simply open the package and implant the device. It may be desirable to prepackage a kit including several unitary surgical devices of different sizes. As discussed above, for the embodiments of FIGS. 3-10, a kit could include several unitary surgical devices 10, each with a pair of anchors 16, 18 separated by a variety of fixed lengths of suture 20 as the tissue repair material. For the embodiments of FIGS. 11-23, 25-40, 42 and 44-45, 53, each device could be made in a plurality of sizes, such as small, medium and large; a kit could comprise a group of unitary surgical devices of all sizes or a group of unitary surgical devices all of one size, for example. Conventional commercially available packaging materials and sterilization techniques can be used. For example, gamma irradiation or electron beam irradiation can be used for this terminal sterilization. It should be understood however, that the present invention is not limited to any particular packaging material or sterilization technique unless expressly called for in the claims.

If any of the embodiments are to be seeded with living cells such as chondrocytes, the terminally sterilized implant can subsequently be seeded with living cells and packaged in an appropriate medium for the cell type used. For example, a cell culture medium comprising Dulbecco's Modified Eagles Medium (DMEM) can be used with standard additives such as non-essential aminoacids, glucose, ascorbic acid, sodium pyrovate, fungicides, antibiotics, etc., in concentrations deemed appropriate for cell type, shipping conditions, etc.

Figure 2:
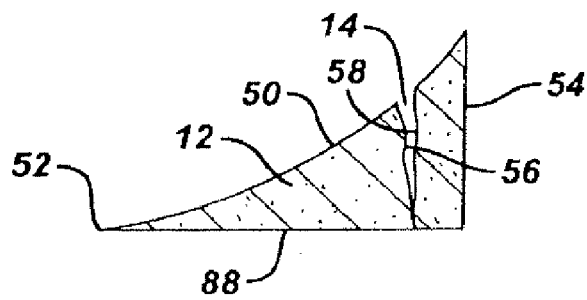
FIG. 2 is a cross-section taken along line 2-2 of the meniscus of FIG. 1.

Use of the illustrated embodiments of the invention is described below. All of the embodiments of the present invention may be used in surgical repair of a damaged meniscus 12, as illustrated in FIGS. 1-2, where the meniscal injury is illustrated as a meniscal tear 14 extending down from the top bearing surface 50 of the meniscus 12 between the inner arcuate edge 52 of the meniscus 12 and the back or outer arcuate surface 54 of the meniscus 12. It should be understood that the drawings show the meniscus 12 in simplified form for purposes of illustration only.

The first group of illustrated unitary surgical repair devices, illustrated in FIGS. 4-10, are useful for surgical meniscal repairs. With each of these devices, the objective is the same: to position the anchors 16, 18 beyond the tear 14, and to position the tissue repair material 20, comprising suture in the embodiments of FIGS. 4-10, across the tear 14. For each of these embodiments, a surgical kit would generally be provided with several unitary surgical devices 10, with varying lengths of suture, provided in the kit. The meniscal tear is evaluated and the meniscus is prepared in the standard manner. From the initial evaluation, the surgeon determines the length of device that is needed to extend across the meniscal injury for the particular patient, and then selects one of the devices from the surgical kit. Using the embodiments illustrated in FIGS. 4 and 8, at least one of the anchors, such as first anchor 16, is positioned within the meniscus 12, while the second anchor 18 is positioned on the back arcuate surface 54 of the meniscus, with the suture 20 connecting the anchors and extending across the tear 14. The first anchor 16 is pushed far enough into the meniscus to approximate the two inner surfaces 56, 58 of the meniscal tear 14. The shapes of the anchors 16, 18 hold their final position. Neither anchor is exposed on a bearing surface of the meniscus. For the embodiments of FIGS. 4 and 8, preferably the anchor 18 that bears against the back non-bearing surface 54 of the meniscus is positioned first, and then the anchor 16 that extends into the interior of the meniscus is positioned. A tubular needle such as that used with the RAPIDLOC™ Meniscal Repair System could be employed. Such a device could have a cable or similar structure running through the needle and connected to a trigger or similar device to selectively to implant one of the anchors. The surgeon could insert the needle through the top articular surface 50 of the meniscus, and push the needle through the body of the meniscus until reaching the back surface 54. The trigger may then be operated to release one of the anchors, such as anchor 18 in FIG. 4, against the back surface 54 of the meniscus. At this stage, a length of suture 20 extends out of the top surface 50 of the meniscus and extends to the other anchor 16. The surgeon may then use a pair of forceps of similar device and push the anchor 16 through the top surface 50 and into the body of the meniscus until the two surface 56, 58 at the tear are approximated. Both anchors 16, 18 should then stay in place, holding the meniscus as shown in FIG. 4 so that the meniscus can heal. Similar surgical procedures may be used to implant the embodiments of the unitary surgical devices 10 illustrated in FIGS. 6 and 10. It should be understood that this surgical technique is provided by way of example only, and that the present invention is not limited to any particular surgical technique unless expressly called for in the claims. Additional unitary surgical devices 10 can be implanted until all the tissue surfaces are adequately approximated and the tear is stabilized.

Figure 45:
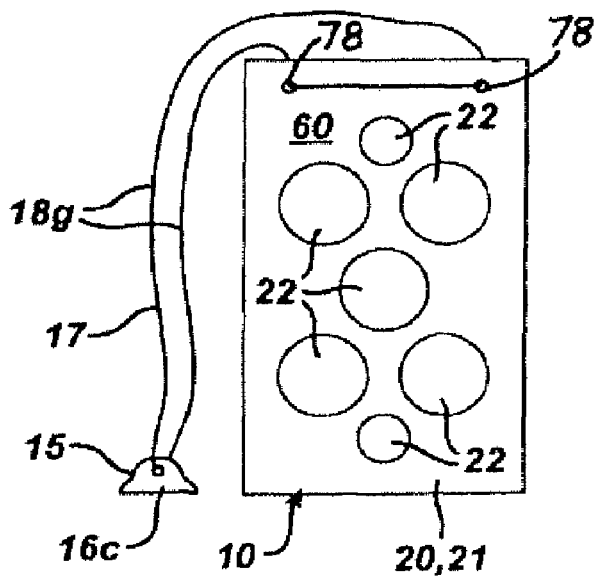
FIG. 45 is a top plan view of a twenty-first embodiment of a unitary surgical device incorporating the teachings of the present invention.
Figure 46:
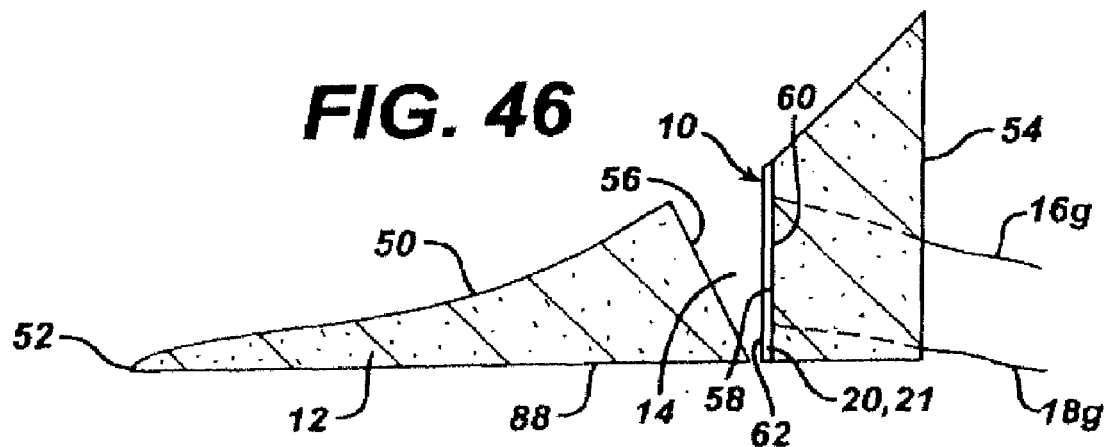
FIG. 46 is a cross-section through a torn meniscus, showing the unitary surgical device of FIG. 44 in place within the meniscal tear prior to approximation of the tissue.
Figure 47:
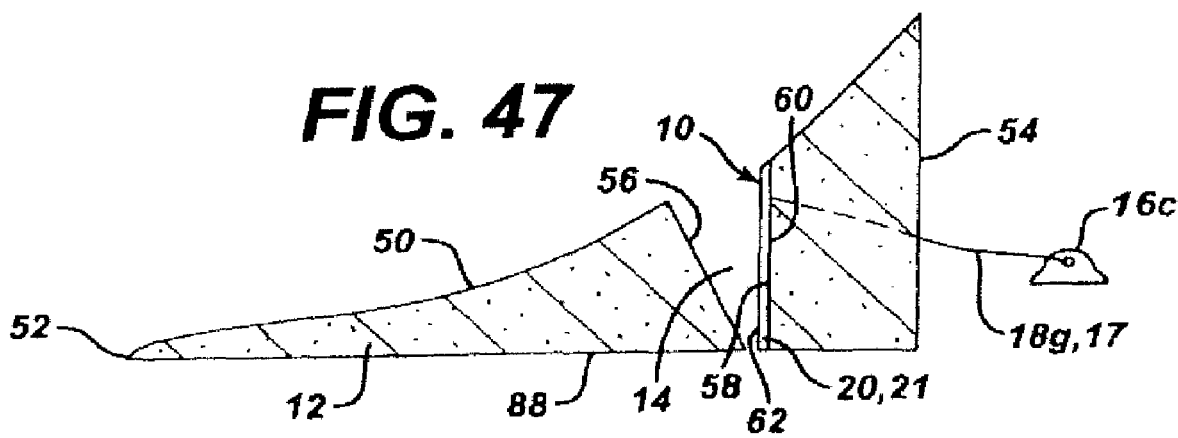
FIG. 47 is a cross-section through a torn meniscus, showing the unitary surgical device of FIG. 45 in place within the meniscal tear prior to approximation of the tissue.
Figure 48:
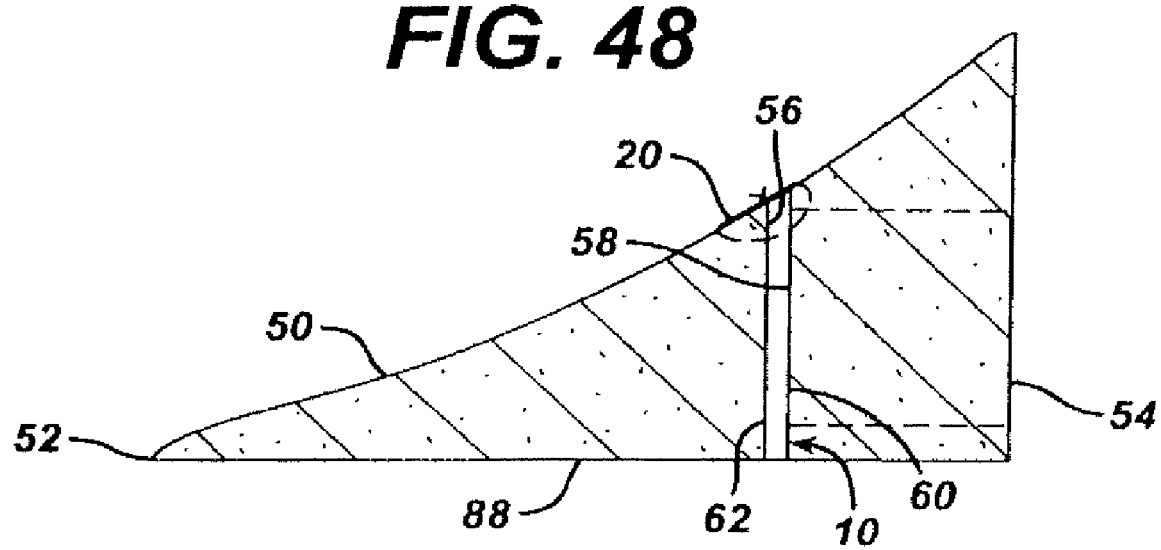
FIG. 48 is a cross-section through a torn meniscus, showing the unitary surgical device of FIGS. 44 and 47 in place within the meniscal tear after approximation of the meniscal tissue.
Figure 49:
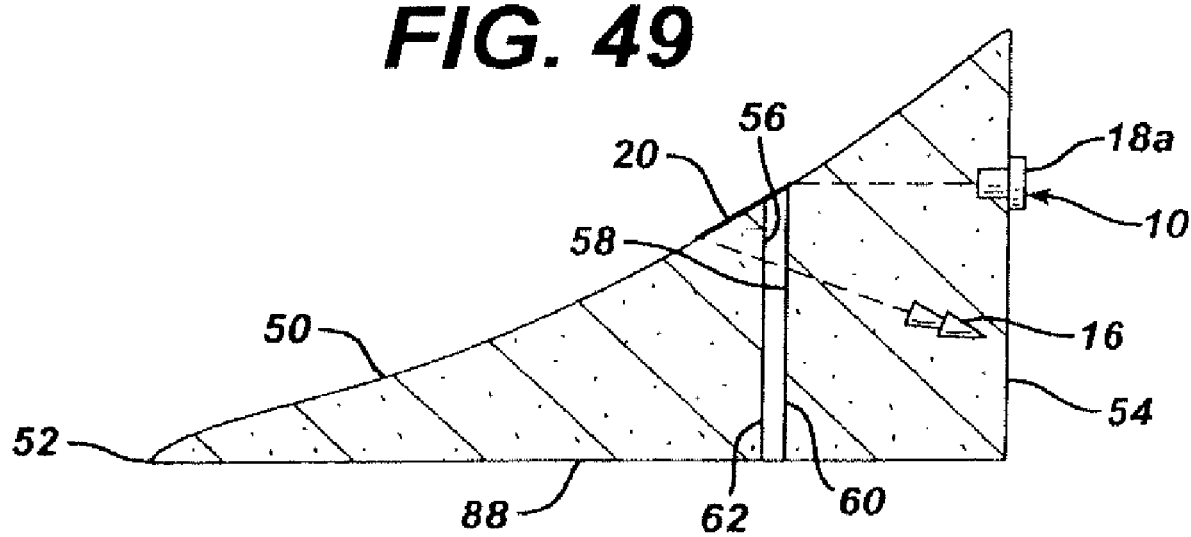
FIG. 49 is a cross-section through a torn meniscus, showing the unitary surgical device of FIGS. 45 and 48 in place within the meniscal tear after approximation of the meniscal tissue.

In some instances, it may be desirable to facilitate healing of the torn meniscus by using a unitary surgical device 10 of the type shown in FIGS. 44 and 45. With these embodiments of the invention, the base 21 and tissue regeneration material 22 are thin, and nearly planar in cross section. The anchoring devices 16, 18 are used for delivering the unitary surgical device to the proper location in the meniscal tear 14, between the two inner surfaces 54, 56 of the meniscal tear 14. With these devices, the first anchor 16, or first and second anchors 16, 18, are inserted on the end of one or two needles (not shown), and the needles are pushed through the inner surface 58 of the meniscal tear 14 and through the body of the meniscus and out through the back side 54 of the meniscus 12. The anchoring device or devices 16, 18 are moved through the back 54 of the meniscus until one of the faces 60 of the unitary surgical device 10 is juxtaposed with the inner surface 58 of the meniscal tear 14, as shown in FIGS. 46 and 47. The remaining suture at the back of the meniscus may be cut off, removed and discarded. Once the unitary surgical device 10 is in place in the meniscal tear 14 as shown in FIGS. 46-47, the surgeon may then approximate the meniscal inner surface 56 and the opposite face 62 of the base 21 of the unitary surgical device 10, and secure the parts in this position using suture or another unitary surgical device, such as one of the devices of FIGS. 4-10. FIGS. 48 and 49 illustrate the meniscus with the tear 14 approximated to the implanted unitary surgical device 10. In FIG. 48, the surfaces of the meniscus and the implanted unitary surgical device are secured together with suture, shown at 64, while in FIG. 49, the surfaces are secured together with another unitary surgical device 10 of the type shown in FIG. 4.

Instruments that may be used in delivering the unitary surgical devices of FIG. 45 may include a Meniscal Applier (REF 228000) available from the Mitek Products division of Ethicon, Inc., of Westwood, Mass. The Mitek Meniscal Applier may be modified to provide a greater curvature if desired. 90° mosquito forceps may also be used to implant the unitary surgical devices.

Figure 15:
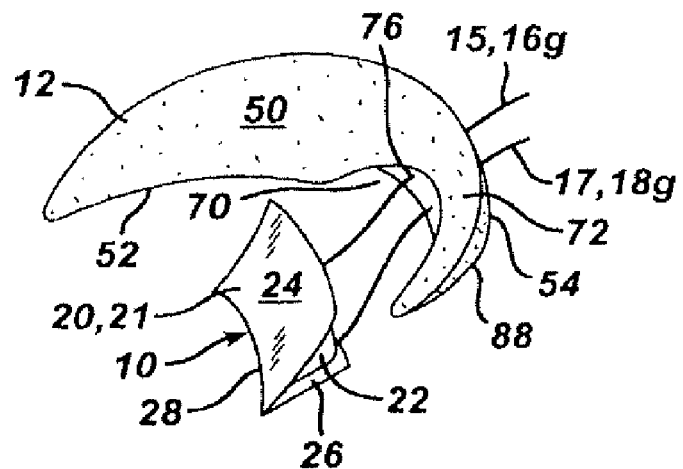
FIG. 15 is a perspective diagrammatic view of a meniscus, with a void left by a partial meniscectomy and with the unitary surgical device of FIGS. 13-14 in the process of being implanted.
Figure 24:
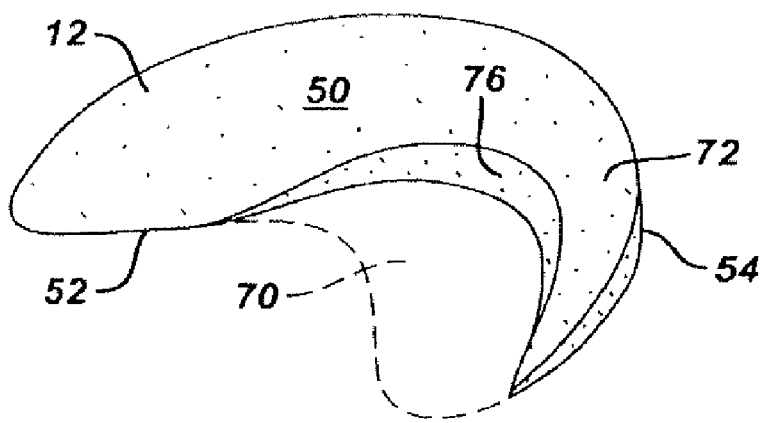
FIG. 24 is a perspective diagrammatic view of a meniscus, with a void left by a partial menisectomy.

If the injury or damage to the meniscus 12 is so severe that a meniscectomy or partial meniscectomy is necessary, the surgeon may remove a portion of the meniscus as illustrated in FIGS. 15 and 24. Generally, the surgeon will remove the damaged or diseased tissue, as shown in FIGS. 15 and 24, leaving a generally wedge-shaped void 70. It should be understood that the illustrations in FIGS. 15 and 24 are simplified for purposes of illustration; the actual area of removed tissue may look different from that illustrated. The portion of the meniscus that is removed is from the inner arcuate edge 52 of the meniscus to a position inward of the back arcuate surface 54 of the meniscus, so that an arcuate portion of the back 54 of the meniscus remains after the meniscectomy. This back portion to the meniscus, shown at 72 in FIGS. 15-17, 19, 21, 24-26, 29, 31, 33, 36, 38 and 40. Although the meniscectomy can extend to the highly vascularized red zone of the meniscus, the back portion 72 can include more than red zone tissue.

With part of the meniscus 12 removed, the surgeon may opt to use one of the embodiments of the unitary surgical device 10 illustrated in FIGS. 11-23, 25-40 and 42. Considering each embodiment in order, the unitary surgical device 10 of the FIG. 11 embodiment is wedge shaped in cross-section, and may be placed so that the tissue regeneration material and the base 21 fit within the void 70 left after part of the meniscus has been removed. The first and second anchors 16, 18 comprise two lengths of suture secured to a disc 73 of biocompatible and bioabsorbable material. The first and second anchoring sutures extend through a part of the tissue regeneration material 22, and out through the lower face of the base 21. These anchoring sutures 16, 18 may be pushed through the back portion 72 of the meniscus as shown in FIG. 12, and pulled tight until the back surface 74 of the device 10 is juxtaposed with the front surface 76 of the back portion 72 of the meniscus. The ends of the two anchoring sutures 16, 18 may then be tied against the back surface 54 of the meniscus 12 as shown in FIG. 12.

Figure 16:
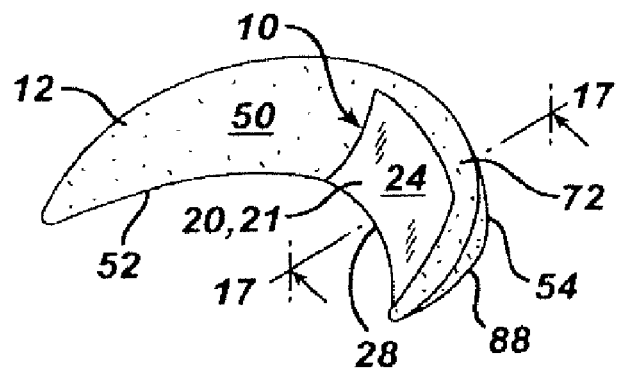
FIG. 16 is a perspective diagrammatic view of the meniscus of FIG. 15, shown with the unitary surgical device of FIGS. 13-15 fixated to the meniscus.
Figure 17:
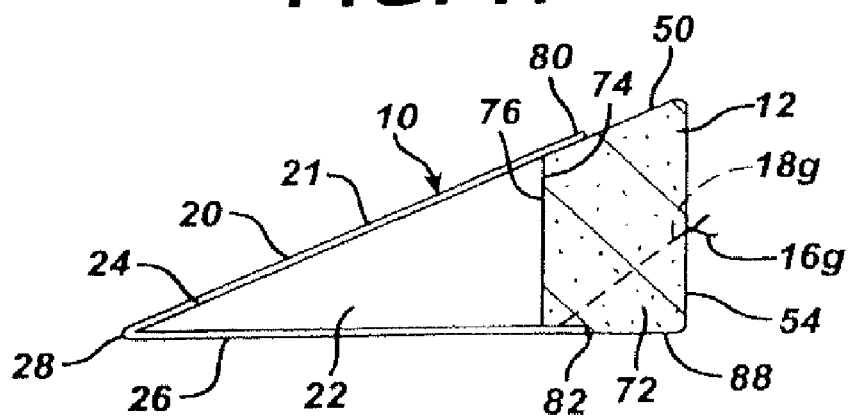
FIG. 17 is a cross-section of the meniscus and unitary surgical device of FIG. 16, taken along line 17-17 of FIG. 16.

In the embodiment of FIG. 13, the base 21 is somewhat larger than the wedge of tissue regeneration material 22, extending rearward of the back surface 74 of the tissue regeneration material 22 and forming upper and lower projections 80, 82 as shown in FIG. 14. In this embodiment, the first and second anchoring sutures 16, 18 comprise a length of suture extending substantially across one dimension of the base 21 at the back of the base, and out through holes 78 in the base 21. The two anchor sutures 16, 18 may be inserted with a needle or similar device (not shown) through the front surface 76 of the back red portion 72 of the meniscus, or through the bottom surface of the body of the meniscus. The two anchoring sutures 16, 18 may be pushed through the body of the meniscus and through the arcuate back surface 54, where they may be tied off, as shown in FIG. 17. As shown in FIGS. 16-17, the unitary surgical device substantially fills the void 70 left by the meniscectomy. As shown in FIG. 17, the front surface 76 of the vascularized portion 72 of the meniscus abuts the back surface 74 of the tissue regeneration material 22 so that the blood vessels may deliver cells and other materials to the tissue regeneration material 22 for the healing process.

Figure 18:
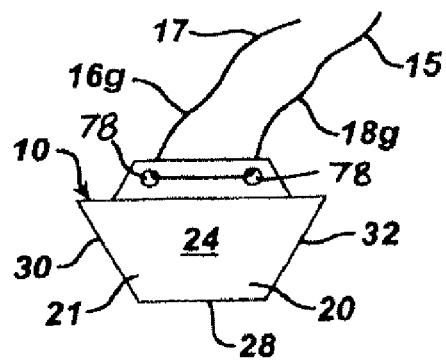
FIG. 18 is a top plan view of a seventh embodiment of a unitary surgical device incorporating the teachings of the present invention.
Figure 19:
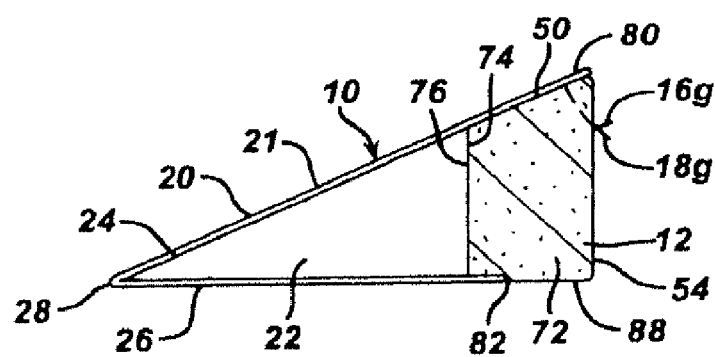
FIG. 19 is a cross-section of a meniscus, after a partial meniscectomy, showing the unitary surgical device of FIG. 18 fixated to the meniscus and at least partially filling the void left by the partial meniscectomy.

The anchoring sutures 16, 18 may also be along the top of the base 21, as shown in the embodiment of FIGS. 18-19, and the upper projection 80 may be greater than the lower projection 82. It should be understood that the lower projection could also be made to be greater than the upper projection 80.

Figure 20:
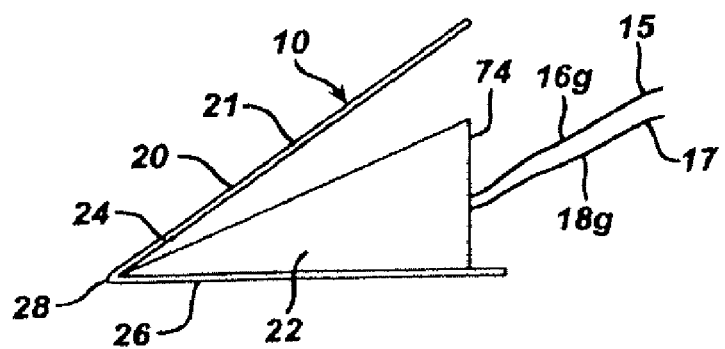
FIG. 20 is an elevation of an eighth embodiment of a unitary surgical device incorporating the teachings of the present invention.
Figure 21:
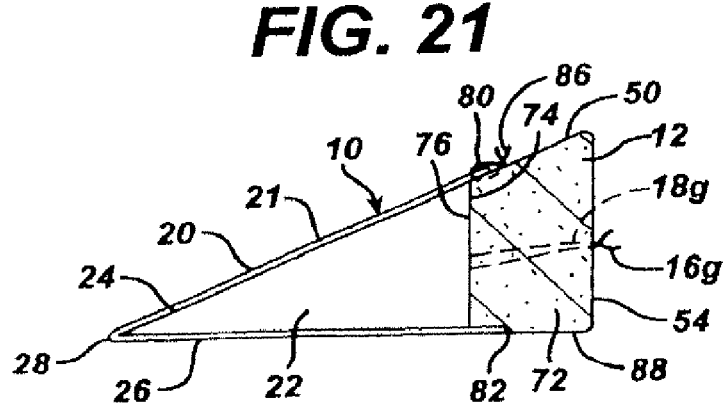
FIG. 21 is a cross-section of a meniscus, after a partial meniscectomy, showing the unitary surgical device of FIG. 20 fixated to the meniscus and at least partially filling the void left by the partial meniscectomy.

As shown in FIGS. 20-21, the anchoring sutures 16, 18 can also be connected directly to the back surface 74 of the mass of tissue regeneration material 22. To make such a unitary surgical device 10, these anchoring sutures 16, 18 could be positioned prior to final forming of the tissue regeneration material, adhered to the tissue regeneration material or mechanically attached to the tissue regeneration material, such as by sewing the suture to the tissue regeneration material; any of these methods of securing the anchors 16, 18 to the tissue regeneration material 22 would be performed prior to implantation of the unitary surgical device. Also as shown in FIG. 20, the top portion of the base 21 need not be secured to the mass of tissue regeneration material 22, the top portion of the base 21 could instead be sutured to the back vascularized portion 72 of the meniscus, as shown at 86 in FIG. 21.

Figure 25:
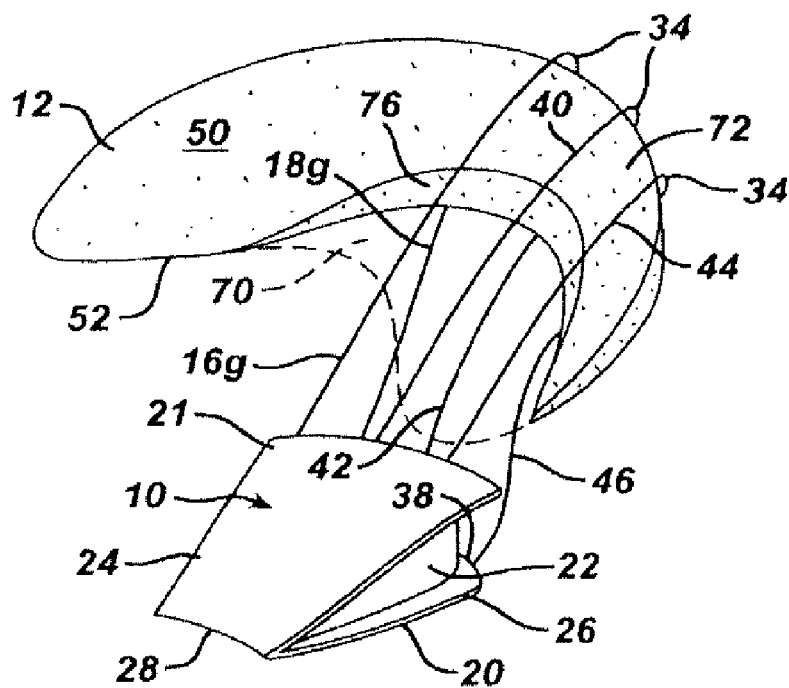
FIG. 25 is a perspective diagrammatic view of a meniscus, with a void left by a partial meniscectomy and with the unitary surgical device of FIGS. 22-23 in the process of being implanted.
Figure 26:
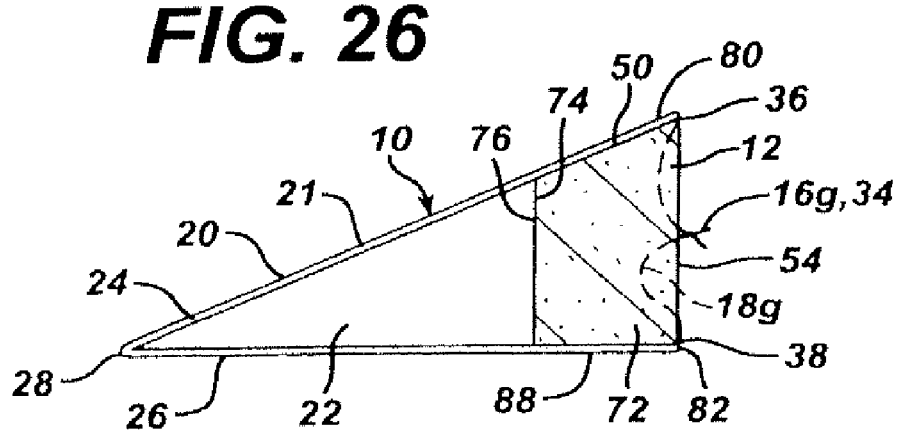
FIG. 26 is a cross-section of a meniscus, after a partial meniscectomy, showing the unitary surgical device of FIGS. 22-23 and 25 fixated to the meniscus and at least partially filling the void left by the partial meniscectomy.

As shown in the embodiment of FIGS. 22-23, 25 and 26, a plurality of anchors 16, 18, 40, 42, 44, 46 may be provided. As shown in FIGS. 25-26, the unitary surgical device 10 of FIGS. 22-23 may be implanted by extending one group of sutures 16, 40, 44 over the top of the vascularized portion 72 of the meniscus, one group of sutures 18, 42, 46 under the vascularized portion 72 of the meniscus, and moving the unitary surgical device toward the vascularized portion 72, so that the unitary surgical device 10 fills the void 70 in the meniscus. All of the sutures 16, 18, 40, 42, 44, 46 may than be anchored to the back surface 54 of the vascularized portion of the meniscus as shown in FIG. 26. As can be seen from FIG. 26, in this embodiment the upper projection 80 and under projection 82 both cover the portion of the upper surface 50 between the surfaces 76 and 54 and the portion of the lower surface 88 of the meniscus between the surfaces 76 and 54.

As shown in the embodiment of FIGS. 28-29, the unitary surgical device 10 need not be wedge shaped. The base 21 could comprise a flat sheet with a pillow or other mass of tissue regeneration material 22 shaped to fill the void 70 left by the meniscectomy. The unitary surgical device 10 may then be fixated to the meniscus 12 by using a needle to push the anchoring sutures 16, 18 through the top surface 50 of the meniscus, and then through the body of the meniscus and out through the back surface 54 of the meniscus, where the anchoring sutures 16, 18 may be tied, thereby fixating the unitary surgical device to the meniscus. The unitary surgical device 10 of the FIG. 42 embodiment may be fixated in a similar manner.

Figure 29A:
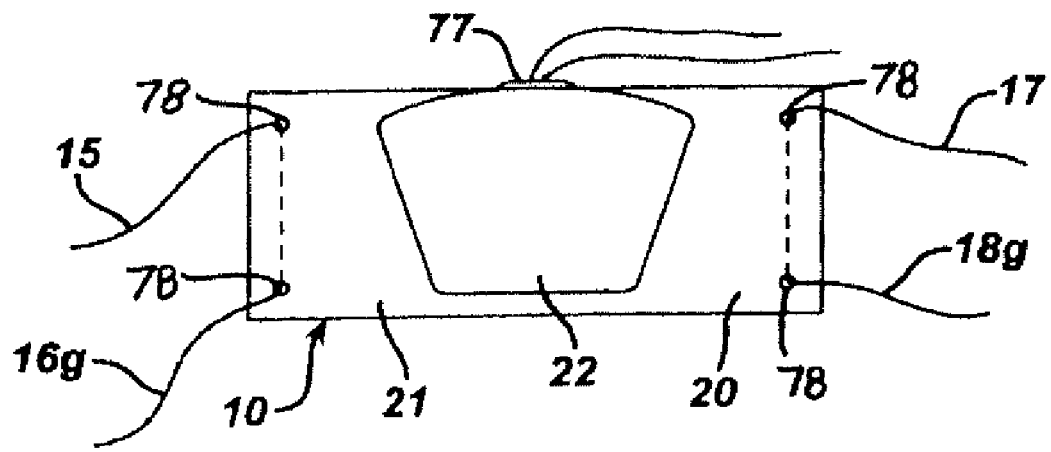
FIG. 29A is a bottom plan view of a twelfth embodiment of a unitary surgical device incorporating the teachings of the present invention.
Figure 29B:
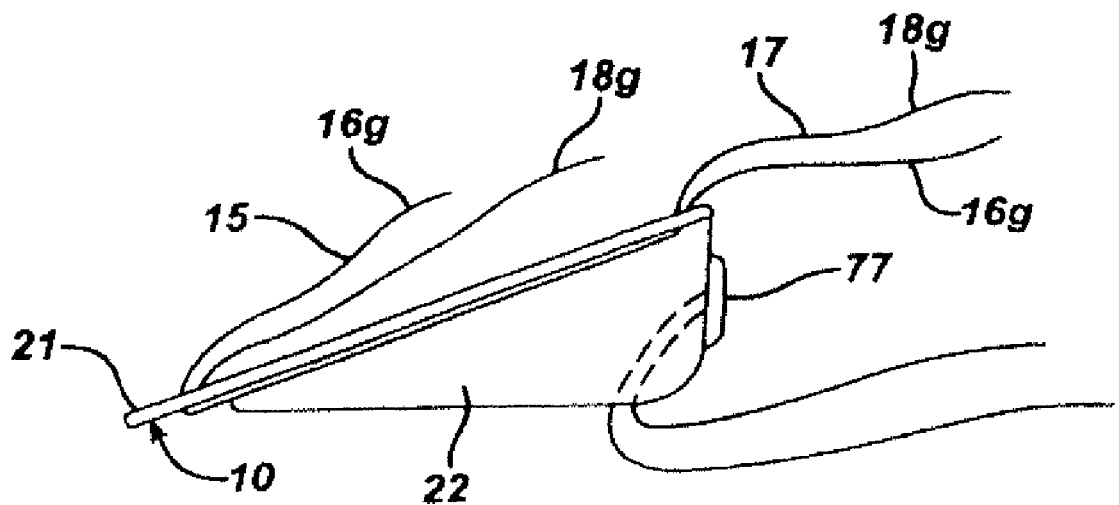
FIG. 29B is a side elevation of the embodiment of FIG. 29A.

In addition, as shown in the embodiment of FIGS. 29A-29B, a flat base 21 could be provided with a wedge or otherwise shaped mass of tissue regeneration material 22 fixed to the base. The base 21 could include two fixating members 15, 17 comprising, for example, two lengths of suture 16g, 18g. A third fixating member 77 could also be included in the unitary surgical device. In the embodiment of FIGS. 29A-29B, the third fixating member 77 comprises a backstop and a length of suture affixed to the mass of tissue regeneration material 22, with the length of suture extending through the mass of tissue regeneration material as in the embodiment of FIGS. 11-12.

As shown in FIG. 27, a unitary surgical device substantially like that shown in FIGS. 28-29 may be provided with barbed darts affixed to the ends of sutures to define the first and second anchors 16, 18. The unitary surgical device 10 of the FIG. 27 embodiment may be fixated to the meniscus 12 in a manner similar to that shown in FIG. 29, except instead of tying the ends of suture for fixation, the barbed darts 16, 18 may be pressed into the body of the meniscus to thereby fixate the device 10 to the meniscus.

The embodiment of FIGS. 30-31 is similar to the embodiment of FIGS. 22-23 and 25-26, except in the embodiment of FIGS. 30-31, each anchor 16, 18, 40, 42, 44, 46 includes a barbed dart at the end of a length of suture. To implant this embodiment, the anchors 16, 18, 40, 42, 44, 46 are moved over and under the portion of the meniscus behind the void 70 and the barbed darts are pushed into the body of the meniscus through the back 54 of the meniscus. The barbed darts are pushed in until the unitary surgical device is properly fixated. The barbs on the darts prevent the darts from being pulled out.

Figure 22:
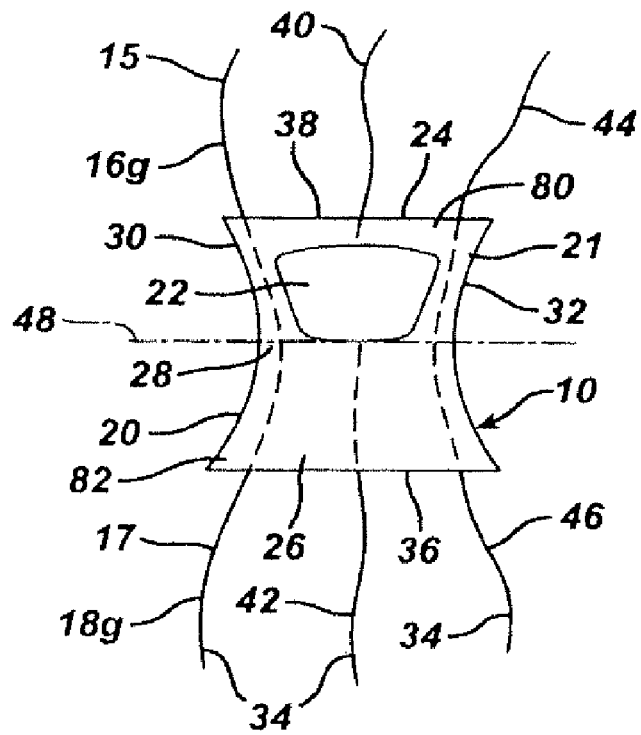
FIG. 22 is a top plan view of a ninth embodiment of a unitary surgical device incorporating the teachings of the present invention.
Figure 23:
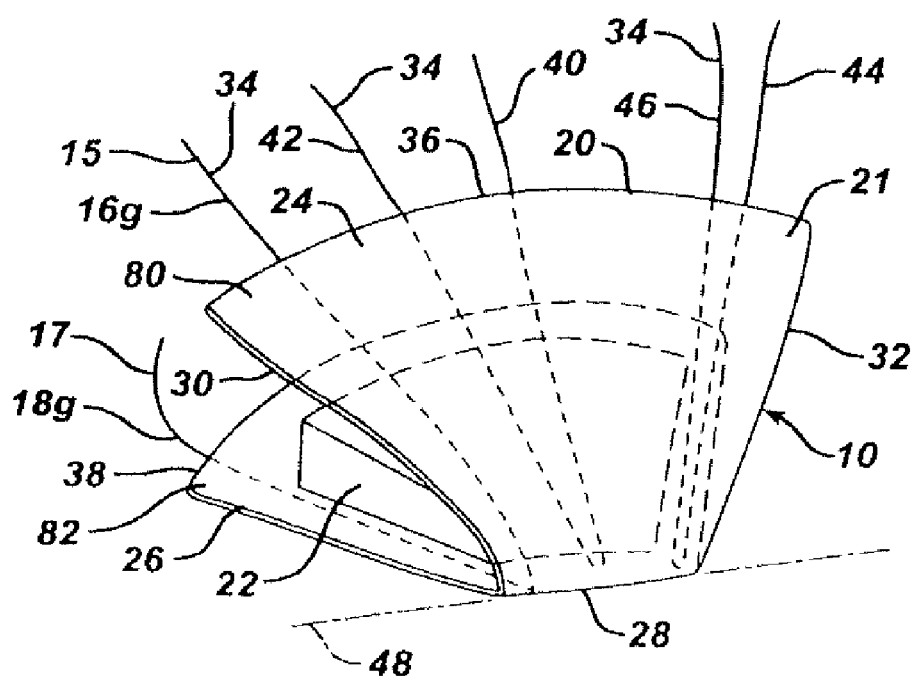
FIG. 23 is a perspective view of the unitary surgical device of FIG. 22, shown with the top panel of the base folded over the mass of tissue regeneration material.
Figure 32:
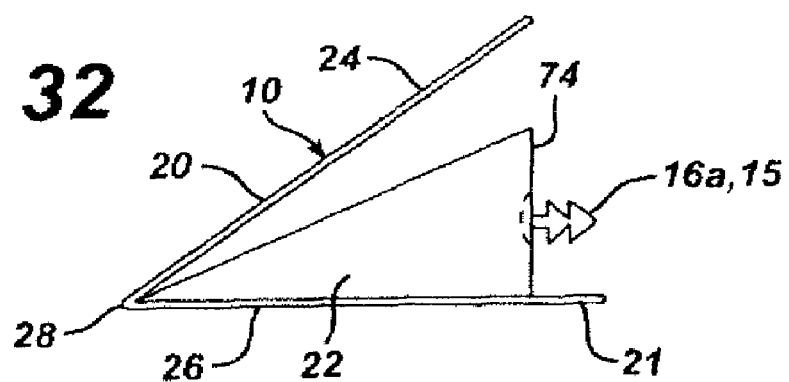
FIG. 32 is an elevation of a fourteenth embodiment of a unitary surgical device incorporating the teachings of the present invention.
Figure 33:
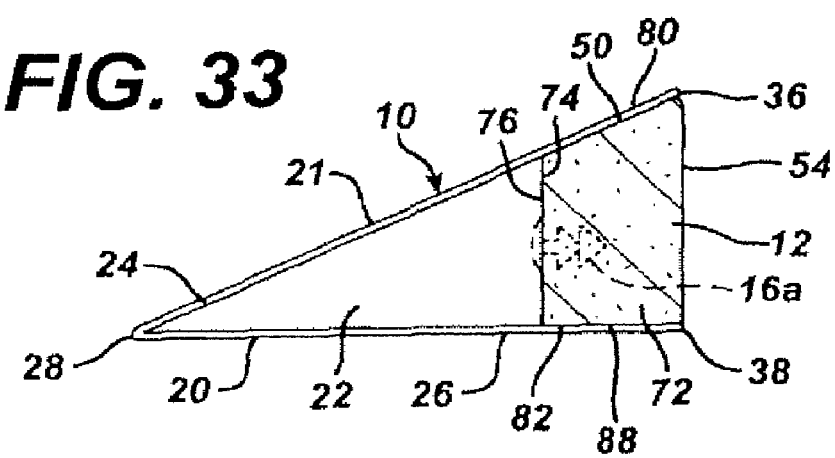
FIG. 33 is a cross-section of a meniscus, after a partial meniscectomy, showing the unitary surgical device of FIG. 32 fixated to the meniscus and at least partially filling the void left by the partial meniscectomy.

The embodiment of FIGS. 32-33 is similar to that of FIGS. 20-21, except that instead of using suture as the first and second anchors 16, 18, barbed darts are affixed to extend outward from the back 74 of the mass of tissue regeneration material 22. To implant this unitary surgical device, the upper and lower projections 80, 82 are moved over and under the surfaces 50, 88 of the vascularized portion 72 of the meniscus behind the void 70 until the barbed darts enter the face 76 of the meniscus at the back of the void 70 created during the meniscectomy. The barbs on the dart fixate the implant in place against the meniscus. It should be understood that although only one anchoring barbed dart 16 is illustrated in FIGS. 22-23, it is contemplated that more than a single anchoring device may be used in this embodiment. In addition, although the top panel 24 of the base 21 may be affixed to the mass of tissue regeneration material by adhesion, cross-linking, mechanical fixation or the like, the top panel 24 can also be free from such connection and can be surgically fixated to the body of the meniscus as described above with respect to the embodiment of FIGS. 20-21.

In the embodiment of FIG. 34, the first and second anchors comprise mating darts and holes. The darts extend upward from the bottom projection 82 and the mating holes are in the upper projection 80. The darts are long enough to extend through the body of part of the meniscus. The embodiment of FIG. 34 may be fixated by placing the device 10 in the void 70 in the meniscus, positioning the bottom projection 82 under part of the meniscus so that the darts extend upward through the meniscus and exit the top of the meniscus. The top panel 24 of the base 21 may then be pressed down so that the tops of the darts extend through the holes and lock the top and bottom portions of the base together and to the meniscus.

In the embodiment of FIGS. 35-36, the first and second anchors 16, 18 comprise tacks, and an additional pair of tacks are provided as third and fourth anchors 40, 42. In the embodiment of FIGS. 35-36, the mass of tissue regeneration material 22 is affixed to the top panel 24 of the base 21 by adhesive, cross-linking (chemical or physical) or through mechanical means. The tacks are provided on both the upper and lower projections 80, 82. When implanted, the mass of tissue regeneration material fits within the void 70 left after the meniscectomy, and the projections 80, 82 are positioned over and under the upper and lower surfaces 50, 88 of the meniscus 12, between the surfaces 76 and 54 of the meniscus. The tacks extend into the body of the meniscus between the surfaces 76 and 54, thereby fixating the unitary surgical device 10 to the meniscus.

In the embodiment of FIGS. 37-38, the unitary surgical device is implanted in a manner similar to the other embodiments. The device 10 is positioned so that the void 70 is substantially filled by the mass of tissue regeneration material 22. Then, the top panel 24 is moved to place the upper projection 80 over the top surface 50 of the portion of the meniscus behind the void 70 and the bottom panel is moved to place the lower projection 82 under the lower surface 88 of the meniscus behind the void 70. The female locking member 18 is pushed upward through the lower surface 88 and into the body of the meniscus, and the male locking member 16 is pushed downward through the upper surface 50 into the body of the meniscus until at least part of the male locking member 16 is received in the female locking member 18, thereby fixating the device 10 to the meniscus.

In the embodiment of FIGS. 39-40, the device 10 may be fixated by first implanting the female locking member 18 using a hollow needle delivery system, like that described above for implanting the device 10 of FIGS. 3 and 4. The female locking member 18 is pushed through the surface 76, through the body of the meniscus and out through the surface 54. The suture extends through this passageway and through part of the implant, such as through the mass of tissue regeneration material 22 and through the top panel 24 of the base. The device 10 may be moved into position with the mass of tissue regeneration material located in the void 70 and against the vascularized portion 72 of the meniscus. The male locking member 16 is then pushed into the female locking member, thereby fixating the unitary surgical device 10 to the meniscus 12.

Figure 50:
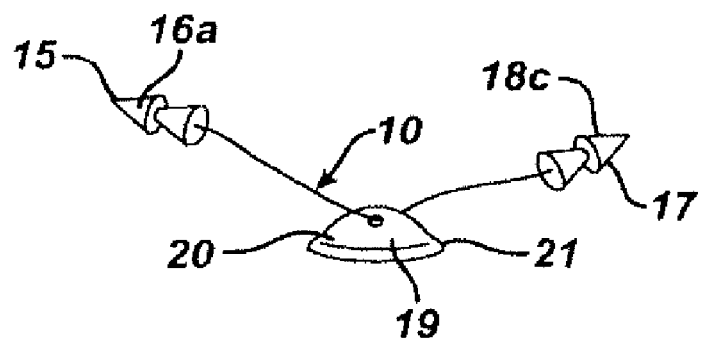
FIG. 50 is a perspective view of a twenty-second embodiment of the unitary surgical device of the present invention.
Figure 51:
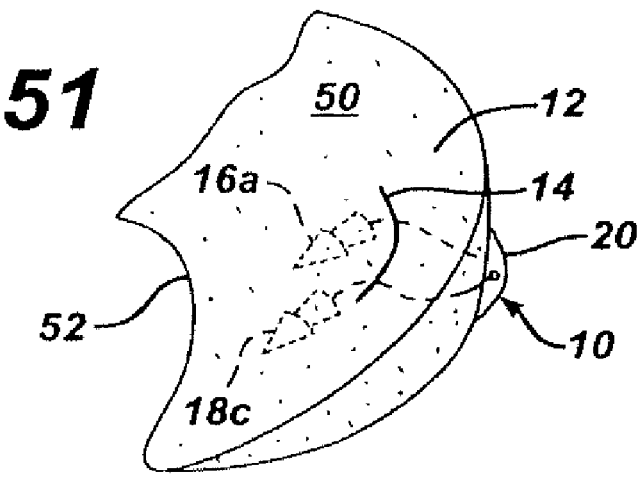
FIG. 51 is a perspective view of a portion of a meniscus, showing the unitary surgical device of FIG. 50 in use in repairing a tear in the meniscus.
Figure 52:
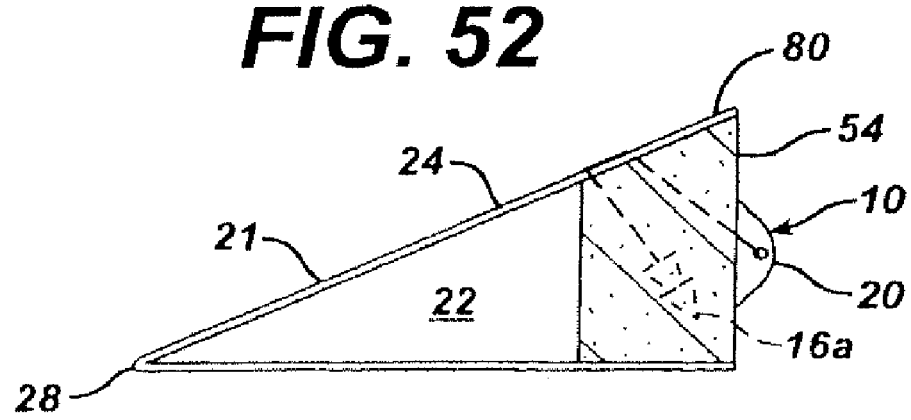
FIG. 52 is a cross-section of a meniscus, after a partial meniscectomy, showing the unitary surgical device of FIG. 37 fixated to the meniscus and at least partially filling the void left by the partial meniscectomy.

The embodiment of FIG. 50 may be used either as a means of approximating the inner surfaces of a meniscal tear, as shown in FIG. 51, or as a means of fixating a tissue regenerating implant after a partial meniscectomy, as shown in FIG. 52. To approximate the surfaces of a tear as shown in FIG. 51, the base 20 (backstop element 19 in FIG. 50) may be inserted using a commercially available device such as a Mitek Meniscal Applier, as described above. Additional standard equipment may then be used to move the first and second anchors 16a, 18c through the non-articulating outer surface 54 of the meniscus, up through the upper articulating surface 50 of the meniscus, across the tear 14, and back into the body of the meniscus until the anchors 16a, 18c are embedded in the meniscus. To fixate a separate tissue regenerating implant as illustrated in FIG. 52, the unitary surgical device 10 of FIG. 50 may be inserted as described above, or could be inserted from the outer, non-articulating side of the meniscus. The anchors 16a, 18c could be pushed through the outer non-articulating surface 54 of the meniscus, through the body of the meniscus, up through the upper articulating surface 50 of the meniscus and through the overlying upper portion 80 of the top panel 24 of the implant. The anchors 16a, 18c may then be moved across a portion of the upper surface of the top panel 24 of the implant and back into the body of the outer portion 72 of the meniscus to fixate the implant in place.

Figure 53:
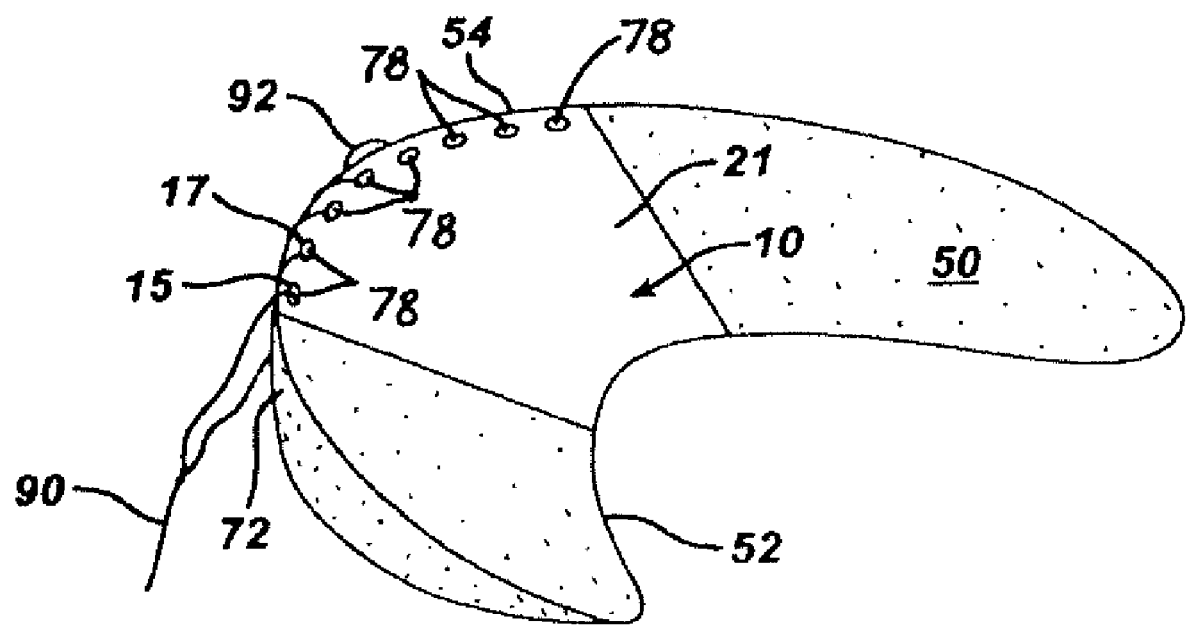
FIG. 53 is a perspective view of a twenty-third embodiment of the unitary surgical device of the present invention, in place on a meniscus.
Figure 54:
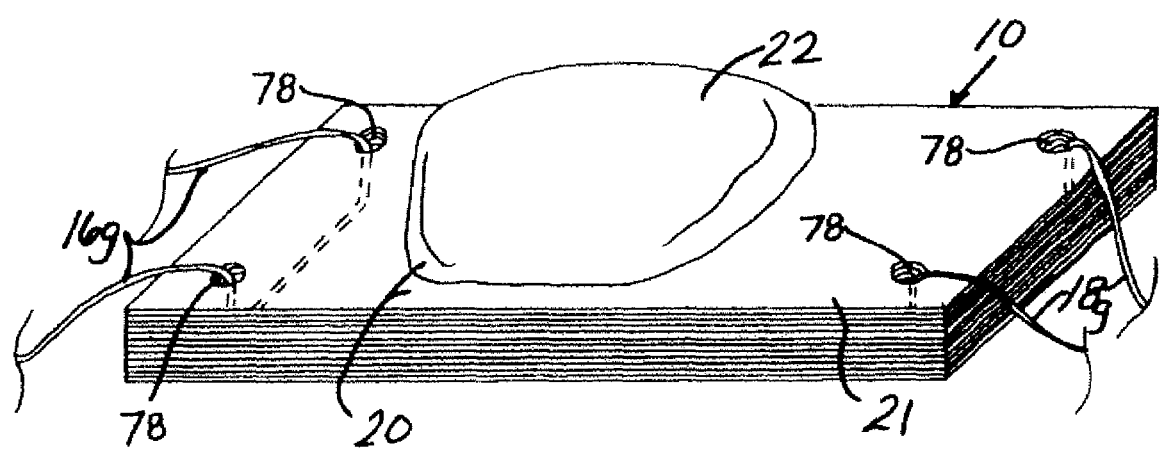
FIG. 54 is a perspective view of the unitary surgical device of FIGS. 28, 29, with the base shown diagrammatically.

An additional embodiment of a unitary surgical device is illustrated in FIG. 53. In this embodiment, the upper projection 80 has a plurality of pre-formed holes along the outer edge. Each hole could thereby comprise a fixating member, as shown at 15 and 17 FIG. 53. These holes could be pre-formed in the base 21 so that the surgeon may easily and quickly suture the unitary surgical implant 10 of FIG. 53 to the outer vascular area 72 of the meniscus through the holes 15, 17, as shown in FIG. 53. To implant such a device, the a length of suture, shown at 90 in FIG. 53, with a backstop, shown at 92 in FIG. 53, could be used. The backstop 92 could be positioned against the outer arcuate surface 54 of the meniscus, and then the suture 90 could be stitched to both the unitary surgical device 10 and the vascularized area 72 of the meniscus using, for example, a corkscrew needle (not shown). With such pre-formed holes in the unitary surgical device, there is little risk of damaging the device during implantation.

Additional surgical techniques can be employed in implanting surgical device of the type described in copending U.S. patent application Ser. No. 10/195,794 entitled "Meniscus Regeneration Device and Method" by Prasanna Malaviya, Herbert Schwartz, David Whalen, Mark Pelo, Phil Jenks, Pamela Plouhar and Jerry Lower.

While only specific embodiments of the invention have been described and shown, it is apparent that various alternatives and modifications can be made thereto. Moreover, those skilled in the art will also recognize that certain additions can be made to these embodiments. It is, therefore, the intention in the appended claims to cover all such alternatives, modifications and additions as may fall within the true scope of the invention.

We claim:

1. A unitary surgical device for surgical implantation in a patient for regenerating meniscal tissue in the patient, the unitary surgical device comprising a tissue repair element and a fixating member:
   the tissue repair element comprising a base and a mass of tissue regeneration material, the base comprising a panel with upper and lower surfaces; and
   the tissue regeneration material being generally wedge-shaped and fixed to at least one of the surfaces of the base;
   wherein the base comprises ECM laminate and the tissue regeneration material comprises non-laminar ECM;
   wherein the fixating member is associated with at least one of the base and the tissue regeneration material; and
   wherein the ECM of at least one of the base and the tissue regeneration material includes a material selected from the group consisting of:
   small intestine submucosa,
   stomach submucosa,
   bladder submucosa,
   alimentary submucosa,
   respiratory submucosa,
   genital submucosa, and
   liver basement membrane.

2. The unitary surgical device of claim 1 wherein the fixating member includes at least one of the following:
   a length of suture fixed to the base;
   at least one hole in the base;
   a biocompatible anchor fixed to the base;
   a biocompatible anchor fixed to the tissue regeneration material; and
   a length of suture fixed to the tissue regeneration material.

3. The unitary surgical device of claim 1 wherein the non-laminar ECM comprises an ECM foam.

4. A unitary surgical device for surgical implantation in a patient for regenerating meniscal tissue in the patient, the unitary surgical device comprising a tissue repair element and a fixating mechanism, the tissue repair element including a base and tissue regeneration material, wherein the base includes ECM laminate defining two panels having a V-shaped configuration in cross-section, the two panels meeting along an apex portion and having end portions spaced distally from the apex portion, the end portions being spaced from each other to provide a gap, wherein the tissue regeneration material comprises non-laminar ECM, wherein the tissue regeneration material is positioned between the two panels of the base and wherein the ECM of at least one of the base and the tissue regeneration material includes a material selected from the group consisting of: small intestine submucosa, stomach submucosa, bladder submucosa, alimentary submucosa, respiratory submucosa, genital submucosa, and liver basement membrane.

5. The unitary surgical device of claim 4 wherein the fixating mechanism includes at least one of the following:
   a length of suture fixed to the base;
   at least one hole in the base;
   a biocompatible anchor fixed to the base;
   a biocompatible anchor fixed to the tissue regeneration material; and
   a length of suture fixed to the tissue regeneration material.

6. The unitary surgical device of claim 4 wherein the unitary surgical device includes a plurality of fixating mechanisms comprising opposing anchors on the end portions of the base panels, the opposing anchors being suitable for fixation to the native meniscus.

7. The unitary surgical device of claim 4 wherein the tissue regeneration material comprises a wedge of ECM foam.

8. The unitary surgical device of claim 1 wherein the ECM laminate comprises a plurality of ECM sheets.

9. The unitary surgical device of claim 4 wherein the ECM laminate comprises a plurality of ECM sheets.

* * * * *